US006887466B2

(12) United States Patent
June et al.

(10) Patent No.: US 6,887,466 B2
(45) Date of Patent: *May 3, 2005

(54) METHODS FOR SELECTIVELY STIMULATING PROLIFERATION OF T CELLS

(75) Inventors: Carl H. June, Rockville, MD (US); Craig B. Thompson, Chicago, IL (US); Gary J. Nabel, Ann Arbor, MI (US); Gary S. Gray, Brookline, MA (US); Paul D. Rennert, Holliston, MA (US)

(73) Assignees: Genetics Institute, Inc., Cambridge, MA (US); Regents of the University of Michigan, Ann Arbor, MI (US); The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/350,202

(22) Filed: Jul. 8, 1999

(65) Prior Publication Data

US 2003/0099643 A1 May 29, 2003

Related U.S. Application Data

(63) Continuation of application No. 08/403,253, filed on Mar. 10, 1995, now Pat. No. 6,352,694, which is a continuation-in-part of application No. 08/253,964, filed on Jun. 3, 1994, now Pat. No. 5,635,697.

(51) Int. Cl.[7] .................. A61K 35/14; A61K 35/26; A61K 35/28
(52) U.S. Cl. .................. 424/93.71; 424/130.1; 424/141.1; 424/143.1; 424/144.1; 424/153.1; 424/154.1; 424/173.1; 424/93.7; 424/534; 424/577; 424/578; 435/2; 435/7.1; 435/7.21; 435/7.24; 435/375; 435/377; 530/387.1; 530/388.1; 530/388.2; 530/388.22; 530/388.7; 530/388.73; 530/388.75
(58) Field of Search ................... 414/130.1, 141.1, 414/153.1, 93.7, 534; 435/2, 2.1, 375; 530/387.1, 388.22, 388.75

(56) References Cited

U.S. PATENT DOCUMENTS

| 5,081,029 A | | 1/1992 | Zarling et al. |
|---|---|---|---|
| 5,500,348 A | | 3/1996 | Nishimura et al. |
| 5,858,358 A | | 1/1999 | June et al. |
| 5,872,222 A | | 2/1999 | Chang |
| 6,010,902 A | * | 1/2000 | Ledbetter et al. |
| 6,129,916 A | * | 10/2000 | Chang |
| 6,352,694 B1 | * | 3/2002 | June et al. |
| 6,534,055 B1 | * | 3/2003 | June et al. |

FOREIGN PATENT DOCUMENTS

EP 0 440 373 8/1991
WO WO 90/05541 5/1990
WO WO 92/00092 1/1992

OTHER PUBLICATIONS

Levine et al. J. Immunol. 159: 5921–5930 (1997).*
Levine et al. Science 272: 1939–1943 (1996).*
Ledbetter et al. PNAS 85: 8628–8632 (1988).*
Rennolt et al. Intl. Immunol. 9: 805–813 (1997).*
Ledbetter et al. PNAS 85: 8628–8632 (1988).*
Levine et al. Science 272 : 1939–1943 (1996).*
Levine et al. J. Immunol 159: 5921–5930 (1997).*
Hellstrom et al. PNAS 98: 6783–6788 (2001).*
Orchard et al. Hum Gene Ther. 13: 979–988 (2002).*
Pene et al. J. Immunol. Methods 283: 59–66 (2003).*
Boucheix, C. et al., "Molecular Cloning of the CD9 Antigen," The Journal of Biological Chemistry, vol. 266, No. 1, pp. 117–122 (1991).
Carroll et al., "Stimulus–response Coupling in Human Platelets Activated by Monoclonal Antibodies to the CD9 Antigen, a 24 kDa Surface Membrane Glycoprotein," Biochem. J., vol. 266, pp. 527–535 (1990).
Chow et al. Nature, vol. 361, pp. 650–654 (1993).
Fahey et al. Clin. Exp. Immunol. vol. 88, pp. 1–5 (1992).
Garbrecht, et al. J. Immunol. Methods. vol. 107, pp. 137–142 (1988).
Guinan et al. Blood, vol. 84,pp. 3261–3282 (1994).
Haynes, Ann. Med. vol. 28, pp. 39–41 (1996).
Hirsch, New England J. Med., vol. 328, pp. 1686–1695 (1993).
Kalinski et al., "Functional Maturation of Human Naïve T Helper Cells in the Absence of Accessory Cells," The Journal of Immunology, vol. 154, pp. 3753–3760 (1995).
Kmiec. American Scientist. vol. 87, pp. 240–247 (1999).
Lanza et al., "cDNA Cloning and Expression of Platelet p24/CD9" Journal of Biological Chemistry, vol. 266, No. 16, pp. 10638–10645 (1991).
Ledbetter et al., PNAS, vol. 85, pp. 8628–8632 (1988).
Lederman et al., Molecular Immunology, vol. 18, pp. 1171–1181 (1991).

(Continued)

*Primary Examiner*—Phillip Gambel
(74) *Attorney, Agent, or Firm*—Wilmer Cutler Pickering; Hale and Dorr LLP

(57) ABSTRACT

Methods for inducing a population of T cells to proliferate by activating the population of T cells and stimulating an accessory molecule on the surface of the T cells with a ligand which binds the accessory molecule are described. T cell proliferation occurs in the absence of exogenous growth factors or accessory cells. T cell activation is accomplished by stimulating the T cell receptor (TCR)/CD3 complex or the CD2 surface protein. To induce proliferation of an activated population T cells, an accessory molecule on the surface of the T cells, such as CD28, is stimulated with a ligand which binds the accessory molecule. The T cell population expanded by the method of the invention can be genetically transduced and used for immunotherapy or can be used in methods of diagnosis.

19 Claims, 33 Drawing Sheets

OTHER PUBLICATIONS

Li et al., PNAS, vol. 77, pp. 3211–3214 (1990).

Åsjö et al., "A Novel Mode of Human Immunodeficiency Virus Type 1 (HIV–1) Activation: Ligation of CD28 Alone Induces HIV–1 Replication in Naturally Infected Lymphocytes" *J. of Virology* vol. 67, No. 7, pp. 4395–4398, Jul. 1993.

Azuma et al., "Functional Expression of B7/BB1 on Activated T Lymphocytes" *J. of Exp. Med.* vol. 177, pp 845–850, Mar. 1993.

Baroja et al., "The Anti–T Cell Monoclonal Antibody 9.3 (Anti–CD28) Provides a Helper Signal and Bypasses the Need for Accessory Cells in T Cell Activation with Immobilized Anti–CD3 and Mitogens" Cellular Immunology vol. 120, pp. 205–217, 1989.

Baroja et al., "Cooperation Between an Anti–T Cell (Anti–CD28) Monoclonal Antibody and Monocyte–produced IL–6 in the Induction of T Cell Responsiveness to IL–2" *The Journal of Immunology* vol. 141, No. 5, pp. 1502–1507, Sep. 1, 1988.

Damle and Doyle, "Stimulation Via the CD3 and CD28 Molecules Induces Responsiveness to IL–4 in $CD4^+CD29^+CD45R^-$ Memory T Lymphocytes" *The Journal of Immunology* vol. 143, No. 6, pp. 1761–1767, Sep. 15, 1989.

Damle et al., "Differential Regulatory Signals Delivered by Antibody binding to the CD28 (Tp44) Molecule During the Activation of Human T Lymphocytes" *The Journal of Immunology* vol. 140, No. 6, pp. 1753–1761, Mar. 15, 1988.

Diegel et al., "Regulation of HIV Production by Blood Mononuclear Cells from HIV–Infected Donors: II. HIV–1 Production Depends on T Cell–Monocyte Interaction," *AIDS Research and Human Retroviruses*, vol. 9, No. 5, pp. 465–473, 1993.

Freedman et al., "Selective Induction of B7/BB–1 on Interferon–γ Stimulated Monocytes: A Potential Mechanism for Amplification of T Cell Activation through the CD28 Pathway" *Cellular Immunology* vol. 137, pp. 429–437, 1991.

Galvin et al., "Murine B7 Antigen Provides A Sufficient Costimulatory Signal For Antigen–Specific and MHC–Restricted T Cell Activation" *J. of Immunol.* vol. 149, No. 12, pp. 3802–3808, Dec. 15, 1992.

Geppert, and Lipsky, "Accessory Cell Independent Proliferation of Human T4 Cells Stimulated by Immobilized Monoclonal Antibodies to CD3," *The Journal of Immunology*, vol. 138, No. 6, pp. 1660–1666, Mar. 15, 1987.

Groux et al., "Activation–induced Death by Apoptosis in $CD4^+$ T Cells from Human Immunodeficiency Virus–infected Asymptomatic Individuals," *J. Exp. Med.*, vol. 175, pp. 331–340, Feb. 1992.

Hansen et al., "Monoclonal Antibodies Identifying a Novel T–Cell Antigen and Ia Antigens of Human Lymphocytes" *Immunogenetics* vol. 10, pp. 247–260, 1980.

Hara et al., "Human T cell activation" *J. Exp. Med.* vol. 161, pp. 1513–1524, Jun. 1985.

Harding et al., "CD28–mediated signalling co–stimulates murine T cells and prevents induction of anergy in T–cell clones" *Nature* vol. 356, pp 607–609, Apr. 1992.

Jong et al., "Regulation of T–Cell Differentiation by CD2 and CD28 Accessory Molecules" *Immunology* vol. 74, pp. 175–182, 1991.

June et al., "Evidence for the Involvement of Three Distinct Signals in the Induction of IL–2 Gene Expression in Human T Lymphocytes" *The Journal of Immunology* vol. 143, No. 1, pp. 153–161.

June et al., "Role of the CD28 Receptor in T–Cell Activation" *Immunology Today* vol. 11, No. 6, pp. 211–216, 1990.

June et al., "T–Cell Proliferation Involving the CD28 Pathway Is Associated with Cyclosporine–Resistant Interleukin 2 Gene Expression" *Molecular and Cellular Biology* vol. 7, No. 12, pp. 4472–4481, Dec. 1987.

King et al., "CD28 Activation Promotes Th2 Subset Differentiation by Human $CD4^+$ Cells," *Eur. J. Immunol.*, vol. 25, pp. 587–595, 1995.

Koulova et al., "Identification of the Anti–CD3–Unresponsive Subpopulation of $CD4^+$, $CD45RA^+$ Peripheral T Lymphocytes" *The Journal of Immunology* vol. 145, No. 7, pp. 2035–2043, Oct. 1, 1990.

Ledbetter et al., "Antibodies to Tp67 and Tp44 Augment and Sustain Proliferative Response of Activated T Cells" *The Journal of Immunology* vol. 135, No. 4, pp. 2331–2336, Oct. 1985.

Ledbetter et al., "Antibody Binding to CD5 (Tp67) and Tp44 T Cell Surface Molecules: Effects on Cyclic Nucleotides, Cytoplasmic Free Calcium, and cAMP–Mediated Suppression" *The Journal of Immunology* vol. 137, No. 10, pp. 3299–3305, Nov. 15, 1986.

Lyerly et al. AIDS Research and Human Retroviruses (Abstract only) vol. 3, pp. 87–94, 1987.

Malim et al. J. Exp. Med. vol. 176, pp. 1197–1201 (1997).

Ngo et al. "In the Protein Folding–Problem and Tertiary Structure Prediction," Merz et al. (ed.) (1994).

Perno et al. J. Exp. Med. vol. 168, pp. 1111–1116 (1988).

Roederer et al. J.Clin. Invest. vol. 99, pp. 1555–1564 (1997).

Scadden, J. Acquired Immune Deficiency Syndrome and Human Retrovirology vol. 16 (Suppl. 1) pp. S23–S29, 1997.

Skolnick. Trends in BioTech., vol. 18, pp. 34–39 (2000).

Van Noesel et al. J. Clin. Invest. vol. 86, pp. 293–299 (1990).

Verma, et al. Nature, vol. 389, pp. 239–242 (1997).

Zola, et al., "The p24 Leucocyte Membrane Antigen: Modulation Associate with Lymphocyte Activation and Differentiation," Immunol. Cell Biol., vol. 67, pp. 63–70 (1989).

Ledbetter et al., "CD28 Ligation in T–Cell Activation: Evidence for Two Signal Transduction Pathways" *Blood* vol. 75, No. 7, pp. 1531–1539, Apr. 1, 1990.

Ledbetter et al., "Crosslinking of Surface Antigens Causes Ionized Calcium in T Lymphocytes" *Proceedings of the National Academy of Sciences*, vol. 84, pp. 1384–1388, Mar. 1987.

Ledbetter et al., "Role of CD2 cross–linking in cytoplasmic calcium responses and T cell activation" *Eur. J. Immunol.* vol. 18, pp. 1601–1608, 1988.

Lee et al., "The Cd28 Signal Transduction Pathway in T Cell Activation" *Advances in Regulation of Cell Growth, vol. 2; Cell Activation: Genetic Approaches* vol. 2, Chapter 7, pp. 141–160, 1991.

Lesslauer et al., T90/44 (9.3 antigen). "A cell surface molecule with a function in human T cell activation" *Eur. J. Immounol* . vol. 16, pp. 1289–1296, 1986.

Linsley et al., "Binding of the B Cell Activation Antigen B7 to CD28 Costimulates T Cell Proliferation and Interleukin 2 mRNA Accumulation" *Journal of Experimental Medicine* vol. 173, pp. 721–730, Mar. 1991.

Martin et al., "A 44 Kilodalton Cell Surface Homodimer Regulates Interleukin 2 Production by Activated Human T Lymphocytes" *The Journal of Immunology* vol. 136, No. 9, pp. 3282–3287, May 1, 1986.

McArthur and Raulet, "CD28–induced Costimulation of T Helper Type 2 Cells Mediated by Induction of Responsiveness to Interleukin 4," *J. Exp. Med.*, vol. 178, pp. 1645–1653, Nov. 1993.

Moran et al., "Regulation of HIV Production by Blood Mononuclear Cells from HIV–Infected Donors: I. Lack of Correlation Between HIV–1 Production and T Cell Activation," *AIDS Research and Human Retroviruses*, vol. 9, No. 5, pp. 455–464, 1993.

Norton et al., "The CD28 Ligand, B7, Enhances IL–2 Production by Providing a Costimulatory Signal to T Cells" *The Journal of Immunology* vol. 149, No. 5, pp. 1556–1561, Sep. 1, 1992.

Perrin et al., "Administration of Anti–CD28–Specific Monoclonal Antibody 9.3: Preclinical Studies," *Blood Suppl.*, p. 439a, No. 1747, 1991.

Pierres et al., "CD3$^{low}$ Human Thymocyte Population can readily be Triggered Via the CD2 and/or CD28 Activation Pathways Whereas the CD3 Pathway Remains Nonfunctional" *The Journal of Immunology* vol. 144, No. 4, pp. 1202–1207, Feb. 15, 1990.

Pierrès et al., "Triggering CD 28 molecules synergize with CD 2 (T 11.1 and T 11.2)–mediated T cell activation" *Eur. J. Immunol.* vol. 18, pp 685–690, 1988.

Reiser et al., "Murine B7 antigen provides an efficient costimulatory signal for activation of murine T lymphocytes via the T–cell receptor/CD3 complex" *Proc. Natl. Acad. Sci.* vol. 89, pp. 271–275, Jan. 1992.

Riddell et al., "The Use of Anti–CD3 and Anti–CD28 Monoclonal Antibodies to Clone and Expand Human Antigen–Specific T Cells" *Journal of Immonolgical Methods* vol. 128, pp. 189–201, 1990.

Schwartz et al., "Costimulation of T Lymphocytes: The Role of CD28, CTLA–4, and B7/BB1 in Interleukin–2 Production and Immunotherapy" *Cell* vol. 71, pp. 1065–1068, Dec. 24, 1992.

Shanafelt et al.,"Costimulatory Signals can Selectively Modulate Cytokine Production by Subsets of CD4$^+$ T Cells," *The Journal of Immunology*, vol. 154, pp. 1684–1690, 1995.

Tan et al., "Induction of Alloantigen–specific Hyporesponsiveness in Human T Lymphocytes by Blocking Interaction of CD28 with Its Natural Ligand B7/BB1" *Journal of Experimental Medicine* vol. 177, No. 1, pp 165–173, Jan. 1993.

Thompson et al., "CD28 Activation Pathway Regulates the Production of Multiple T–cell–derived Lymphokines/cytokines" *Proceedings of the National Academy of Sciences* vol. 86, pp. 1333–1337, Feb. 1989.

Turka et al., "CD28 is an Inducible T Cell Surface Antigen that Transduces a Proliferative Signal in CD3$^+$Mature Thymocytes" *The Journal of Immunology* vol. 144, No. 5, pp. 1646–1653, Mar. 1, 1990.

Van der Pouw–Kraan et al., "Development of Human Th1 and Th2 Cytokine Responses: The Cytokine Production Profile of T Cells is Dedicated by the Primary in vitro Stimulus" *European Journal of Immunology* vol. 23, pp. 1–5, 1993.

Van der Pouw–Kraan et al., "Interleukin (IL)–4 Production by Human T Cells: Differential Regulation of IL–4 vs. IL–2 Production" *European Journal of Immunology* vol. 22, pp. 1237–1241, 1992.

Van Lier et al., "Signals involved in T cell activation. T cell proliferation induced through the synergistic action of anti–CD28 and anti–CD2 monoclonal antibodies" *Eur. J. Immunol.* vol. 18, pp. 167–172, 1988.

Von Fliedner et al., "Production of Tumor Necrosis Factor–α by Naive or Memory T Lymphocytes Activated via CD28" *Cellular Immunology* vol. 139, pp. 198–207, 1992.

Weiss et al., "Synergy Between the T3/Antigen Receptor Complex and Tp44 in the Activation of Human T Cells" *The Journal of Immunology* vol. 137, No. 3, pp. 819–825, Aug. 1, 1986.

Yang et al., "A novel activation pathway for mature thymocytes" *J. Exp. Med.* vol. 168, pp. 1457–1468, Oct. 1988.

Zocchi et al., "CD1+ Thymocytes Proliferate and Give Rise to Functional Cells after Stimulation with Monoclonal Antibodies Recognizing CD3, CD2 or CD28 Surface Molecules" *Cellular Immunology* vol. 129, pp. 394–403, 1990.

* cited by examiner

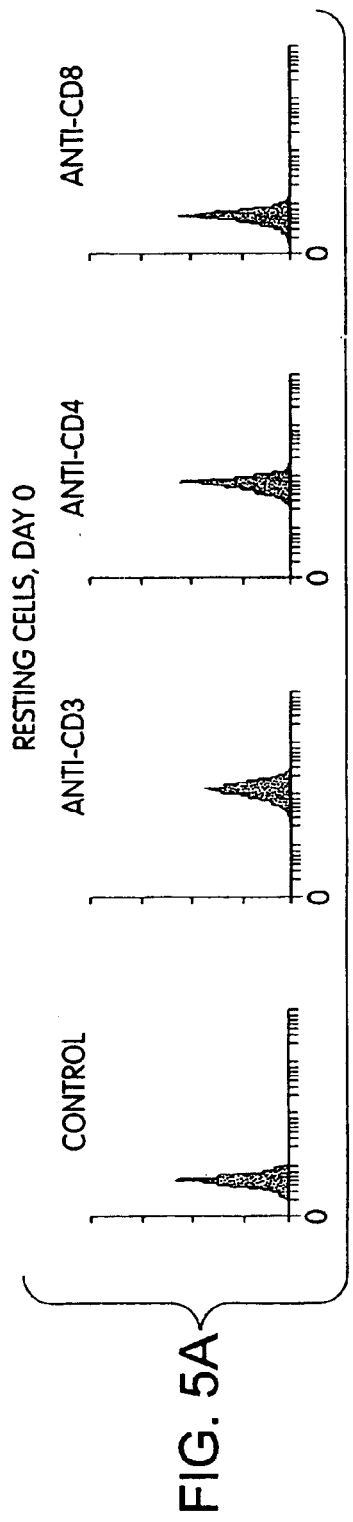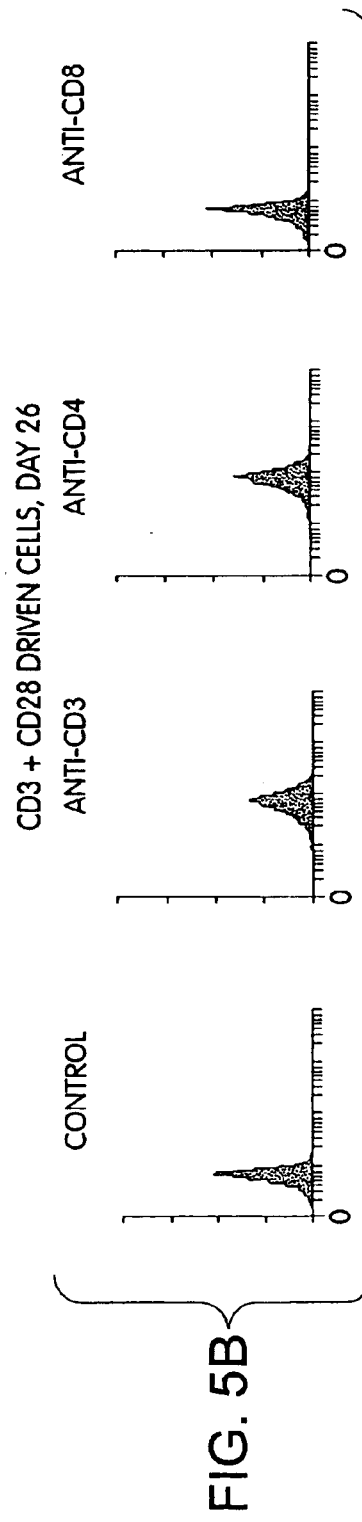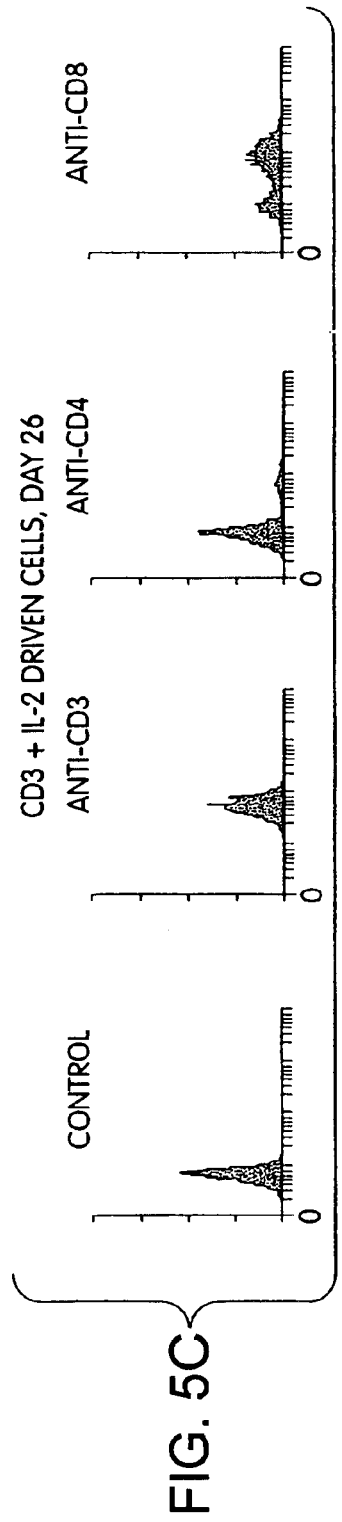
FIG. 5A
FIG. 5B
FIG. 5C

1: G19-4sp + IL-2
2: G19-4sp + 9.3
3: G19-4sp + EX5.3D10
4: G19-4sp + ES5.2D8
5: G19-4sp +7G11
6: G19-4sp + 9.3 + ES5.2D8
7: G19-4sp + 9.3 + 7G11
8: G19-4sp +ES5.2D8 + 7G11

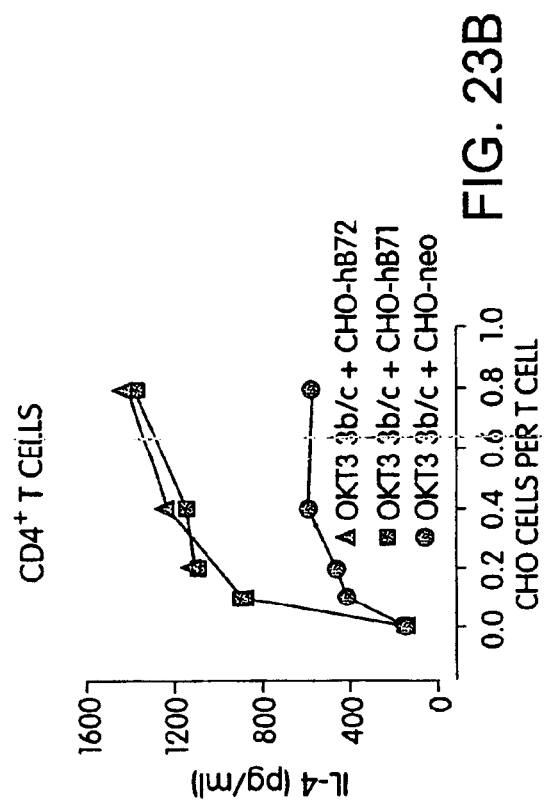
FIG. 23B
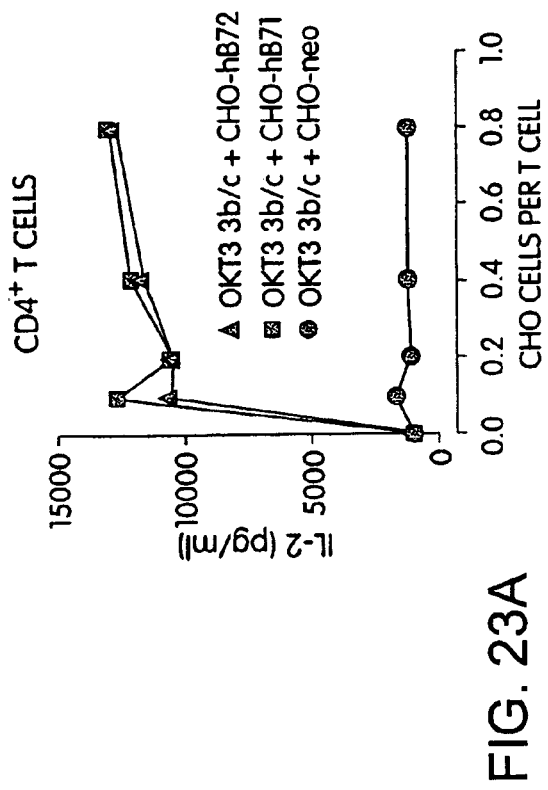
FIG. 23A
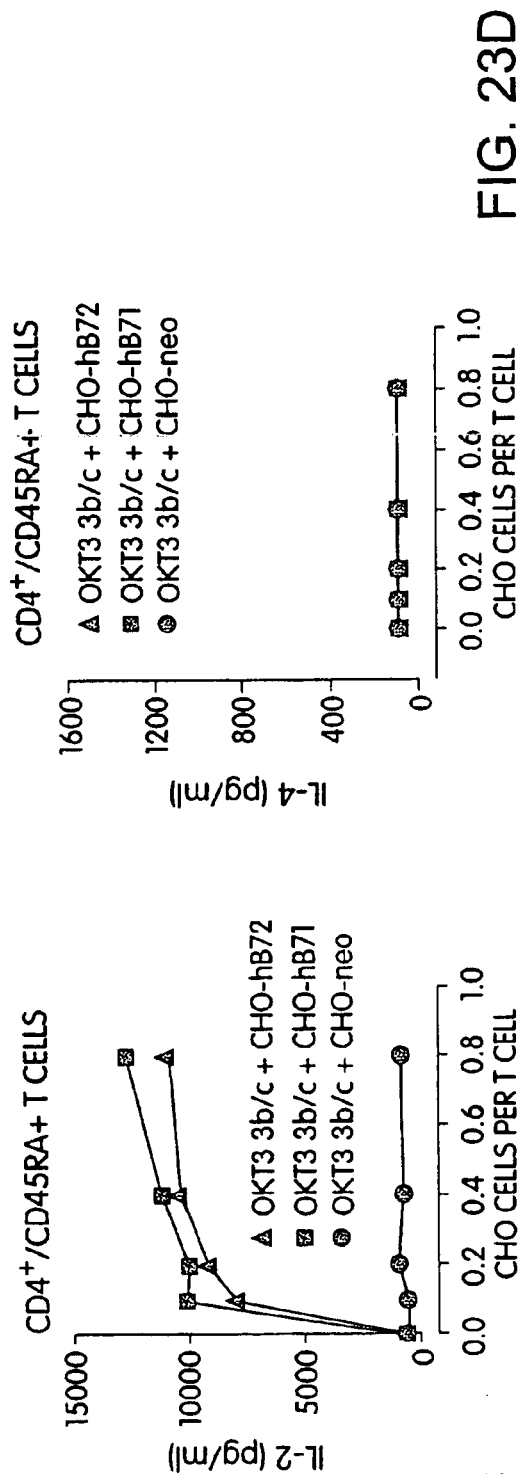
FIG. 23D
FIG. 23C

METHODS FOR SELECTIVELY STIMULATING PROLIFERATION OF T CELLS

RELATED APPLICATIONS

This application is a continuation of U.S. Ser. No. 08/403,253, filed Mar. 10, 1995, entitled "Methods for Selectively Stimulating Proliferation of T Cells" (now U.S. Pat. No. 6,352,694); which in turn is a continuation-in-part of U.S. Ser. No. 08/253,964, filed Jun. 3, 1994 now U.S. Pat. No. 5,635,697, entitled "Methods for Selectively Stimulating Proliferation of T Cells" (currently pending). The contents of the aforementioned applications are hereby incorporated by reference.

BACKGROUND OF THE INVENTION

The development of techniques for propagating T cell populations in vitro has been crucial to many of the recent advances in the understanding of T cell recognition of antigen and T cell activation. The development of culture methods for the generation of human antigen-specific T cell clones has been useful in defining antigens expressed by pathogens and tumors that are recognized by T cells to establish methods of immunotherapy to treat a variety of human diseases. Antigen-specific T cells can be expanded in vitro for use in adoptive cellular immunotherapy in which infusions of such T cells have been shown to have anti-tumor reactivity in a tumor-bearing host. Adoptive immunotherapy has also been used to treat viral infections in immunocompromised individuals.

Techniques for expanding human T cells in vitro have relied on the use of accessory cells and exogenous growth factors, such as IL-2. The use of IL-2 and, for example, an anti-CD3 antibody to stimulate T cell proliferation is known to expand the $CD8^+$ subpopulation of T cells. The requirement for MHC-matched antigen presenting cells as accessory cells presents a significant problem for long-term culture systems. Antigen presenting cells are relatively short lived. Thus, in a long-term culture system, antigen presenting cells must be continuously obtained from a source and replenished. The necessity for a renewable supply of accessory cells is problematic for treatment of immunodeficiencies in which accessory cells are affected. In addition, when treating viral infection, accessory cells which may carry the virus may result in contamination of the entire T cell population during long term culture. An alternative culture method to clone and expand human T cells in vitro in the absence of exogenous growth factor and accessory cells would be of significant benefit.

SUMMARY OF THE INVENTION

This invention pertains to methods for selectively inducing ex vivo expansion of a population of T cells in the absence of exogenous growth factors, such as lymphokines, and accessory cells. In addition, T cell proliferation can be induced without the need for antigen, thus providing an expanded T cell population which is polyclonal with respect to antigen reactivity. The method provides for sustained proliferation of a selected population of $CD4^+$ or $CD8^+$ T cells over an extended period of time to yield a multi-fold increase in the number of these cells relative to the original T cell population.

According to the method of the invention, a population of T cells is induced to proliferate by activating the T cells and stimulating an accessory molecule on the surface of the T cells with a ligand which binds the accessory molecule. Activation of a population of T cells is accomplished by contacting the T cells with a first agent which stimulates a TCR/CD3 complex-associated signal in the T cells. Stimulation of the TCR/CD3 complex-associated signal in a T cell is accomplished either by ligation of the T cell receptor (TCR)/CD3 complex or the CD2 surface protein, or by directly stimulating receptor-coupled signaling pathways. Thus, an anti-CD3 antibody, an anti-CD2 antibody, or a protein kinase C activator in conjunction with a calcium ionophore is used to activate a population of T cells.

To induce proliferation, an activated population of T cells is contacted with a second agent which stimulates an accessory molecule on the surface of the T cells. For example, a population of $CD4^+$ T cells can be stimulated to proliferate with an anti-CD28 antibody directed to the CD28 molecule on the surface of the T cells. Alternatively, $CD4^+$ T cells can be stimulated with a natural ligand for CD28, such as B7-1 and B7-2. The natural ligand can be soluble, on a cell membrane, or coupled to a solid phase surface. Proliferation of a population of $CD8^+$ T cells is accomplished by use of a monoclonal antibody ES5.2D8 which binds to CD9, an accessory molecule having a molecular weight of about 27 kD present on activated T cells. Alternatively, proliferation of an activated population of T cells can be induced by stimulation of one or more intracellular signals which result from ligation of an accessory molecule, such as CD28.

The agent providing the primary activation signal and the agent providing the costimulatory agent can be added either in soluble form or coupled to a solid phase surface. In a preferred embodiment, the two agents are coupled to the same solid phase surface.

Following activation and stimulation of an accessory molecule on the surface of the T cells, the progress of proliferation of the T cells in response to continuing exposure to the ligand or other agent which acts intracellularly to simulate a pathway mediated by the accessory molecule is monitored. When the rate of T cell proliferation decreases, the T cells are reactivated and restimulated, such as with additional anti-CD3 antibody and a co-stimulatory ligand, to induce further proliferation. In one embodiment, the rate of T cell proliferation is monitored by examining cell size. Alternatively, T cell proliferation is monitored by assaying for expression of cell surface molecules in response to exposure to the ligand or other agent, such as B7-1 or B7-2. The monitoring and restimulation of the T cells can be repeated for sustained proliferation to produce a population of T cells increased in number from about 100- to about 100,000-fold over the original T cell population.

The method of the invention can be used to expand selected T cell populations for use in treating an infectious disease or cancer. The resulting T cell population can be genetically transduced and used for immunotherapy or can be used for in vitro analysis of infectious agents such as HIV. Proliferation of a population of $CD4^+$ cells obtained from an individual infected with HIV can be achieved and the cells rendered resistant to HIV infection. Following expansion of the T cell population to sufficient numbers, the expanded T cells are restored to the individual. Similarly, a population of tumor-infiltrating lymphocytes can be obtained from an individual afflicted with cancer and the T cells stimulated to proliferate to sufficient numbers and restored to the individual. In addition, supernatants from cultures of T cells expanded in accordance with the method of the invention are a rich source of cytokines and can be used to sustain T cells in vivo or ex vivo.

The invention also pertains to compositions comprising an agent that provides a costimulatory signal to a T cell for T cell expansion (e.g., an anti-CD28 antibody, B7-1 or B7-2 ligand), coupled to a solid phase surface which may additionally include an agent that provides a primary activation signal to the T cell (e.g., an anti-CD3 antibody) coupled to the same solid phase surface. These agents are preferably attached to beads. Compositions comprising each agent coupled to different solid phase surfaces (i.e., an agent that provides a primary T cell activation signal coupled to a first solid phase surface and an agent that provides a costimulatory signal coupled to a second solid phase surface) are also within the scope of this invention. Furthermore, the invention provides kits comprising the compositions, including instructions for use.

BRIEF DESCRIPTION OF THE DRAWINGS

FIG. 5 depicts fluorescent activated cell sorter analysis (FACS) in which cells were stained after isolation (day 0, panel A), or after 26 days in culture with either CD28 stimulation (panel B) or IL-2 culture (panel C), with phycoerythrin conjugated anti-CD3, CD4, CD8 or with an IgG2a control monoclonal antibody and fluorescence quantified with a flow cytometer.

DETAILED DESCRIPTION OF THE INVENTION

Figure 1:
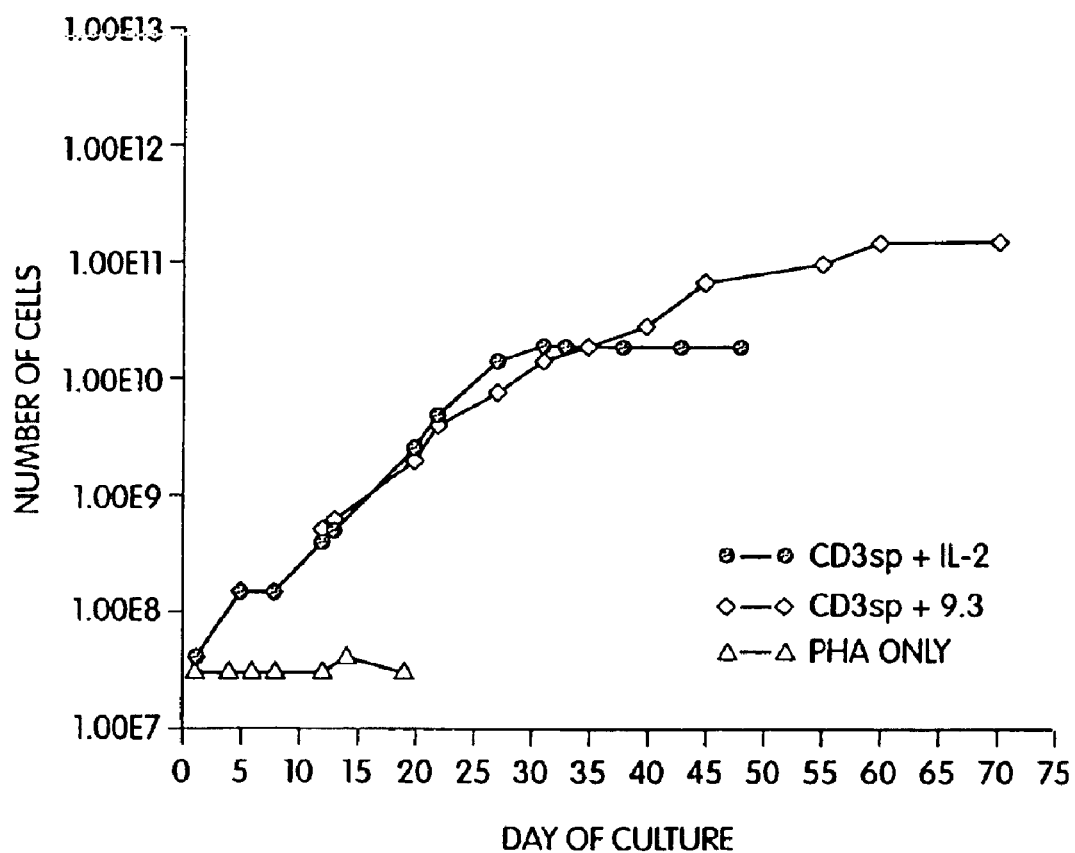
FIG. 1 depicts in vitro growth curves of $CD4^+$ peripheral blood T cells in response to culture with either an anti-CD3 antibody and interleukin-2 (IL-2) (●—●), an anti-CD3 antibody and an anti-CD28 antibody mAb 9.3 (◊—◊) or PHA only (Δ—Δ).

The methods of this invention enable the selective stimulation of a T cell population to proliferate and expand to significant numbers in vitro in the absence of exogenous growth factors or accessory cells. Interaction between the T cell receptor (TCR)/CD3 complex and antigen presented in conjunction with either major histocompatibility complex (MHC) class I or class II molecules on an antigen-presenting cell initiates a series of biochemical events termed antigen-specific T cell activation. The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell.

T cell activation can be accomplished by stimulating the T cell TCR/CD3 complex or via stimulation of the CD2 surface protein. An anti-CD3 monoclonal antibody can be used to activate a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897–906) and the 9.6 antibody (which recognizes the same epitope as T11.1) in combination with the 9-1 antibody (Yang, S. Y. et al. (1986) *J. Immunol.* 137:1097–1100). Other antibodies which bind to the same epitopes as any of the above described antibodies can also be used. Additional antibodies, or combinations of antibodies, can be prepared and identified by standard techniques.

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

Although stimulation of the TCR/CD3 complex or CD2 molecule is required for delivery of a primary activation signal in a T cell, a number of molecules on the surface of T cells, termed accessory or costimulatory molecules have been implicated in regulating the transition of a resting T cell to blast transformation, and subsequent proliferation and differentiation. Thus, in addition to the primary activation signal provided through the TCR/CD3 complex, induction of T cell responses requires a second, costimulatory signal. One such costimulatory or accessory molecule, CD28, is believed to initiate or regulate a signal transduction pathway that is distinct from those stimulated by the TCR complex.

Accordingly, to induce an activated population of T cells to proliferate (i.e., a population of T cells that has received a primary activation signal) in the absence of exogenous growth factors or accessory cells, an accessory molecule on the surface of the T cell, such as CD28, is stimulated with a ligand which binds the accessory molecule or with an agent which acts intracellularly to stimulate a signal in the T cell mediated by binding of the accessory molecule. In one embodiment, stimulation of the accessory molecule CD28 is accomplished by contacting an activated population of T cells with a ligand which binds CD28. Activation of the T cells with, for example, an anti-CD3 antibody and stimulation of the CD28 accessory molecule results in selective proliferation of CD4+ T cells. An anti-CD28 monoclonal antibody or fragment thereof capable of crosslinking the CD28 molecule, or a natural ligand for CD28 (e.g., a member of the B7 family of proteins, such as B7-1 (CD80) and B7-2 (CD86) (Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 262:909–911; Azuma, M. et al. (1993) *Nature* 366:76–79; Freeman, G. J. et al. (1993) *J. Exp. Med* 178:2185–2192)) can be used to induce stimulation of the CD28 molecule. In addition, binding homologues of a natural ligand, whether native or synthesized by chemical or recombinant technique, can also be used in accordance with the invention. Ligands useful for stimulating an accessory molecule can be used in soluble form, attached to the surface of a cell, or immobilized on a solid phase surface as described herein. Anti-CD28 antibodies of fragments thereof useful in stimulating proliferation of CD4+ T cells include monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody. In one specific embodiment, the molecule providing the primary activation signal, for example a molecule which provides stimulation through the TCR/CD3 complex or CD2, and the costimulatory molecule are coupled to the same solid phase support. In particular, T cell activation and costimulation can be provided by a solid phase surface containing anti-CD3 and anti-CD28 antibodies.

A preferred anti-CD28 antibody is monoclonal antibody 9.3 or EX5.3D10. The EX5.3D10 monoclonal antibody was derived from immunizing a Balb/c mouse with CHO (Chinese hamster ovary) cells transfected with the human CD28 gene (designated CHO-hh). Hybridomas from the fusion were selected by whole cell ELISA screening against Jurkat (human T leukemia) CD28 tranfectants designated Jurkat #7. Reactivity of the EX5.3D10 with CD28 was further confirmed by fluorescent activated cell sorter analysis (FACS) analysis in which it was tested side by side with the monoclonal 9.3 (FIG. 6). Neither antibody bound to untransfected CHO-DG44 cells and their binding profiles were nearly identical for the two CD28 transfectant lines, CHO-hh and Jurkat #7, as well as normal human peripheral blood lymphocytes. A hybridoma which produces the monoclonal antibody EX5.3D10 has been deposited with the American Type Culture Collection on Jun. 4, 1993, at ATCC Deposit No. HB11373.

In a specific embodiment of the invention, activated T cells are contacted with a stimulatory form of a natural ligand for CD28 for costimulation. The natural ligands of CD28 include the members of the B7 family of proteins, such as B7-1 (CD80) (SEQ ID NO:1 and 2) and B7-2 (CD86) (SEQ ID NO:3 and 4). B7-1 and B7-2 are collectively referred herein as "B7 molecules". A "stimulatory form of a natural ligand for CD28" is a form of a natural ligand that is able to bind to CD28 and costimulate the T cell. Costimulation can be evidenced by proliferation and/or cytokine production by T cells that have received a primary activation signal, such as stimulation through the CD3/TCR complex or through CD2.

Expression or Coupling of B7 Molecules on the Surface of Cells

In a preferred embodiment of the invention, a B7 molecule is localized on the surface of a cell. This can be accomplished by transfecting a cell with a nucleic acid encoding the B7 molecule (e.g. B7-1, B7-2) in a form suitable for its expression on the cell surface or alternatively by coupling a B7 molecule to the cell surface.

The B7 molecules are preferably expressed on the surface of a cell by transfection of the cell with a nucleic acid encoding the B7 molecule in a form suitable for expression of the molecule on the surface of the cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al. (*Molecular Cloning: A Laboratory Manual, 2nd Edition*, Cold Spring Harbor Laboratory press (1989)) and other laboratory textbooks. The nucleic acid to be introduced may be, for example, DNA encompassing the gene(s) encoding B7-1 and/or B7-2, sense strand RNA encoding B7-1 and/or B7-2 or a recombinant expression vector containing a cDNA encoding B7-1 and/or B7-2. The nucleotide sequence of a cDNA encoding human B7-1 is shown in SEQ ID NO: 1, and the amino acid sequence of a human B7-1 protein is shown in SEQ ID NO:2. The nucleotide sequence of a cDNA encoding human B7-2 is shown in SEQ ID NO: 3, and the amino acid sequence of a human B7-2 protein is shown in SEQ ID NO:4. The nucleic acids encoding B7-1 and B7-2 are further described in Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 262:909–911; Azuma, M. et al. (1993) *Nature* 366:76–79 and; Freeman, G. J. et al. (1993) *J. Exp. Med.* 178:2185–2192.

The nucleic acid is in a form suitable for expression of the B7 molecule in which the nucleic acid contains all of the coding and regulatory sequences required for transcription and translation of a gene, which may include promoters, enhancers and polyadenylation signals, and sequences necessary for transport of the molecule to the surface of the tumor cell, including N-terminal signal sequences. When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs. Regulatory sequences linked to the cDNA can be selected to provide constitutive or inducible transcription, by, for example, use of an inducible promoter, such as the metallothionin promoter or a glucocorticoid-responsive promoter. Expression of B7-1 or B7-2 on the surface of a cell can be accomplished, for example, by including the native transmembrane coding sequence of the molecule in the nucleic acid sequence, or by including signals which lead to modification of the protein, such as a C-terminal inositol-phosphate linkage, that allows for association of the molecule with the outer surface of the cell membrane.

The B7 molecule can be expressed on a cell using a plasmid expression vector which contains nucleic acid, e.g., a cDNA, encoding the B7 molecule. Suitable plasmid expression vectors include CDM8 (Seed, B., *Nature* 329, 840 (1987)) and pMT2PC (Kaufman, et al., *EMBO J.* 6, 187–195 (1987)). Since only a small fraction of cells (about 1 out of $10^5$) typically integrate transfected plasmid DNA into their genomes, it is advantageous to transfect a nucleic acid encoding a selectable marker into the tumor cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid. Following selection of transfected cells using the appropriate selectable marker(s), expression of the costimulatory molecule on the surface of the cell can be confirmed by immunofluorescent staining of the cells. For example, cells may be stained with a fluorescently labeled monoclonal antibody reactive against the costimulatory molecule or with a fluorescently labeled soluble receptor which binds the costimulatory molecule such as CTLA4Ig. Expression of the B7 costimulatory molecule can be determined using a monoclonal antibody, such as BB1 or 133, which recognizes B7-1 or the monoclonal antibody IT2 which recognizes B7-2. Alternatively, a labeled soluble CD28 or CTLA4 protein or fusion protein (e.g., CTLA4Ig) which binds to the B7 molecules can be used to detect expression of B7 on the cell surface.

The cell to be transfected can be any eukaryotic cell, preferably cells that allow high level expression of the transfected gene, such as chinese hamster ovary (CHO) cells or COS cells. The cell is most preferably a CHO cell and a specific protocol for transfection of these cells is provided in Example 11.

In another embodiment, B7 molecules (e.g., B7-1, B7-2) are coupled to the cell surface by any of a variety of different methods. In this embodiment, the B7 molecule to be coupled to the cell surface can be obtained using standard recombinant DNA technology and expression systems which allow for production and isolation of the costimulatory molecule (s) or obtained from a cell expressing the costimulatory molecule, as described below for the preparation of a soluble form of the B7 molecules. The isolated costimulatory molecule is then coupled to the cell. The terms "coupled" or "coupling" refer to a chemical, enzymatic or other means (e.g., antibody) by which the B7 molecule is linked to a cell such that the costimulatory molecule is present on the surface of the cell and is capable of triggering a costimulatory signal in T cells. For example, the B7 molecule can be chemically crosslinked to the cell surface using commercially available crosslinking reagents (Pierce, Rockford Ill.). Another approach to coupling a B7 molecule to a cell is to use a bispecific antibody which binds both the costimulatory molecule and a cell-surface molecule on the cell. Fragments, mutants or variants of a B7 molecule which retain the ability to trigger a costimulatory signal in T cells when coupled to the surface of a cell can also be used.

The level of B7 molecules expressed on or coupled to the cell surface can be determined by FACS analysis, as described in Example 11.

For T cell costimulation, the B7-expressing cells can be cultured to a high density, mitomycin C treated (e.g., at 25 µg/ml for an hour), extensively washed, and incubated with the T cells to be costimulated. The ratio of T cells to B7-expressing cells can be anywhere between 10:1 to 1:1, preferably 2.5:1 T cells to B7-expressing cells.

Soluble Forms of B7 Molecules as Costimulator

The natural ligands of CD28 can also be presented to T cells in a soluble form. Soluble forms of B7 molecules include natural B7 molecules (e.g., B7-1, B7-2), a fragment thereof, or modified form of the full length or fragment of the B7 molecule that is able to bind to CD28 and costimulate the T cell. Costimulation can be evidenced by proliferation and/or cyotkine production by T cells that have received a primary activation signal. Modifications of B7 molecules include modifications that preferably enhance the affinity of binding of B7 molecules to CD28 molecules, but also modifications that diminish or do not affect the affinity of binding of B7 molecules to CD28 molecules. Modifications of B7 molecules also include those that increase the stability of a soluble form of a B7 molecule. The modifications of B7 molecules are usually produced by amino acid substitutions, but can also be produced by linkage to another molecule.

In one specific embodiment, the soluble form of a B7 molecule is a fusion protein containing a first peptide consisting of a B7 molecule (e.g., B7-1, B7-2), or fragment thereof and a second peptide corresponding to a moiety that alters the solubility, binding, affinity, stability, or valency (i.e., the number of binding sites available per molecule) of the first peptide. Preferably, the first peptide includes an extracellular domain portion of a B7 molecule (e.g., about amino acid residues 24–245 of the B7-2 molecule having an amino acid sequence shown in SEQ ID NO: 4) that interacts with CD28 and is able to provide a costimulatory signal as evidenced by stimulation of proliferation of T cells or secretion of cytokines from the T cells upon exposure to the B7Ig fusion protein and a primary T cell activation signal. Thus, a B7-1Ig fusion protein will comprise at least about amino acids 1-208 (SEQ ID NO:2) of B7-1 and a B7-2Ig fusion protein will comprise at least about amino acids 24–245 (SEQ ID NO:4) of B7-2.

The second peptide is a fragment of an Ig molecule, such as an Fc fragment that comprises the hinge, CH2 and CH3 regions of human IgG1 or IgG4. Several Ig fusion proteins have been previously described (see e.g., Capon, D. J. et al. (1989) *Nature* 337:525–531 and Capon U.S. Pat. No. 5,116, 964 [CD4-IgG1 constructs]; Linsley, P. S. et al. (1991) *J. Exp. Med.* 173:721–730 [a CD28-IgG1 construct and a B7-1-IgG1 construct]; and Linsley, P. S. et al. (1991) *J. Exp. Med.* 174:561–569 [a CTLA4-IgG1]). A resulting B7Ig fusion protein (e.g., B7-1Ig, B7-2Ig) may have altered B7-2 solubility, binding affinity, stability, or valency and may increase the efficiency of protein purification. In particular fusion of a B7 molecule or portion thereof to the Fc region of an immunoglobulin molecule generally provides an increased stability to the protein, in particular in the plasma.

Fusion proteins within the scope of the invention can be prepared by expression of a nucleic acid encoding the fusion protein in a variety of different systems. Typically, the nucleic acid encoding a B7 fusion protein comprises a first nucleotide sequence encoding a first peptide consisting of a B7 molecule or a fragment thereof and a second nucleotide sequence encoding a second peptide corresponding to a moiety that alters the solubility, binding, stability, or valency of the first peptide, such as an immunoglobulin constant region. Nucleic acid encoding a peptide comprising an immunoglobulin constant region can be obtained from human immunoglobulin mRNA present in B lymphocytes. It is also possible to obtain nucleic acid encoding an immunoglobulin constant region from B cell genomic DNA. For example, DNA encoding Cγ1 or Cγ4 can be cloned from either a cDNA or a genomic library or by polymerase chain reaction (PCR) amplification in accordance standard protocols. A preferred nucleic acid encoding an immunoglobulin constant region comprises all or a portion of the following: the DNA encoding human Cγ1 (Takahashi, N. S. et al. (1982) *Cell* 29:671–679), the DNA encoding human Cγ2; the DNA encoding human Cγ3 (Huck, S., et al. (1986) *Nucl. Acid Res.* 14:1779); and the DNA encoding human Cγ4. When an immunoglobulin constant region is used in the B7 fusion protein, the constant region can be modified to reduce at least one constant region mediated biological effector function. For example, DNA encoding a Cγ1 or Cγ4 constant region can be modified by PCR mutagenesis or site directed mutagenesis. Protocols and reagents for site directed mutagenesis systems can be obtained commercially from Amersham International PLC, Amersham, UK.

In a particularly prefered embodiment of the invention, B7-1Ig and B7-2Ig fusion proteins comprise about amino acids 1–208 of B7-1 (SEQ ID NO: 2) and about amino acids 24–245 of B7-2 (SEQ ID NO: 4), respectively, fused to the heavy chain of IgG1.

In one embodiment the first and second nucleotide sequences are linked (i.e., in a 5' to 3' orientation by phosphodiester bonds) such that the translational frame of the B7 protein or fragment thereof and the IgC (i.e., Fc fragment that comprises the hinge, CH2, and CH3 regions of human IgG) coding segments are maintained (i.e., the nucleotide sequences are joined together in-frame). Thus, expression (i.e., transcription and translation) of the nucleotide sequence produces a functional B7Ig fusion protein. The nucleic acids of the invention can be prepared by standard recombinant DNA techniques. For example, a B7Ig fusion protein can be constructed using separate template DNAs encoding B7 and an immunoglobulin constant region. The appropriate segments of each template DNA can be amplified by polymerase chain reaction (PCR) and ligated in frame using standard techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The nucleic acids encoding B7 molecules or B7Ig fusion proteins (e.g., B7-1, B7-2) can be inserted into various expression vectors, which in turn direct the synthesis of the corresponding protein in a variety of hosts, particularly eucaryotic cells, such as mammalian or insect cell culture and procaryotic cells, such as E. coli. Expression vectors within the scope of the invention comprise a nucleic acid as described herein and a promotor operably linked to the nucleic acid. Such expression vectors can be used to transfect host cells to thereby produce fusion proteins encoded by nucleic acids as described herein. An expression vector of the invention, as described herein, typically includes nucleotide sequences encoding a B7 molecule or B7Ig fusion protein operably linked to at least one regulatory sequence. "Operably linked" is intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

An expression vector of the invention can be used to transfect cells, either procaryotic or eucaryotic (e.g., mammalian, insect or yeast cells) to thereby produce fusion proteins encoded by nucleotide sequences of the vector. Expression in procaryotes is most often carried out in *E. coli* with vectors containing constitutive or inducible promoters. Certain *E. coli* expression vectors (so called fusion-vectors) are designed to add a number of amino acid residues to the expressed recombinant protein, usually to the amino terminus of the expressed protein. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Examples of fusion expression vectors include pGEX (Amrad Corp., Melbourne, Australia) and pMAL (New England Biolabs, Beverly, Mass.) which fuse glutathione S-tranferase and maltose E binding protein, respectively, to the target recombinant protein. Accordingly, a B7 molecule or B7Ig fusion gene may be linked to additional coding sequences in a procaryotic fusion vector to aid in the expression, solubility or purification of the fusion protein. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector4 relies on host RNA polymerase transcription from the hybrid trp-lac fusion promoter. Target gene expression from the pET 11d vector relies on transcription from the T7 gn10-lacO fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize expression of at B7 molecule or B7Ig fusion protein in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleotide sequence of the B7 molecule or B7Ig fusion protein construct to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences are encompassed by the invention and can be carried out by standard DNA synthesis techniques.

Alternatively, a B7 molecule or B7Ig fusion protein can be expressed in a eucaryotic host cell, such as mammalian cells (e.g., Chinese hamster ovary cells (CHO) or NS0 cells), insect cells (e.g., using a baculovirus vector) or yeast cells. Other suitable host cells may be found in Goeddel, (1990) supra or are known to those skilled in the art. Eucaryotic, rather than procaryotic, expression of a B7 molecule or B7Ig may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material. For example, commonly used promoters are derived from polyoma, Adenovirus 2, cytomegalovirus and Simian Virus 40. To express a B7 molecule or B7Ig fusion protein in mammalian cells, generally COS cells (Gluzman, Y., (1981) *Cell* 23:175–182) are used in conjunction with such vectors as pCDM8 (Seed, B., (1987) *Nature* 329:840) for transient amplification/expression, while CHO (dhfr-Chinese Hamster Ovary) cells are used with vectors such as pMT2PC (Kaufman et al. (1987), *EMBO J.* 6:187–195) for stable amplification/expression in mammalian cells. A preferred cell line for production of recombinant protein is the NS0 myeloma cell line available from the ECACC (catalog #85110503) and described in Galfre, G. and Milstein, C. ((1981) *Methods in Enzymology* 73(13):3–46; and *Preparation of Monoclonal Antibodies: Strategies and Procedures*, Academic Press, New York, N.Y.). Examples of vectors suitable for expression of recombinant proteins in yeast (e.g., *S. cerivisae*) include pYepSec1 (Baldari. et al., (1987) *Embo J.* 6:229–234), pMFa (Kurjan and Herskowitz, (1982) *Cell* 30:933–943), pJRY88 (Schultz et al. (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Vector DNA can be introduced into procaryotic or eucaryotic cells via conventional transformation or transfection techniques such as calcium phosphate or calcium choloride co-precipitation, DEAE-dextran-mediated transfection, lipofection, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of B7 molecules or B7Ig fusion proteins by, for example, immunoprecipitation from cell supernatant with an anti-B7 monoclonal antibody.

B7 molecules or B7 Ig fusion proteins produced by recombinant technique may be secreted and isolated from a mixture of cells and medium containing the protein. Alternatively, the protein may be retained cytoplasmically and the cells harvested, lysed and the protein isolated. A cell culture typically includes host cells, media and other byproducts. Suitable mediums for cell culture are well known in the art. Protein can be isolated from cell culture medium, host cells, or both using techniques known in the art for purifying proteins.

For T cell costimulation, the soluble forms of the natural ligands for CD28 are added to the T cell culture in an amount sufficient to result in costimulation of activated T cells. The appropriate amount of soluble ligand to be added will vary with the specific ligand, but can be determined by assaying different amounts of the soluble ligand in T cell cultures and measuring the extent of costimulation by proliferation assays or production of cytokines, as described in the Examples.

Coupling of the Natural Ligands to a Solid Phase Surface

In another embodiment of the invention, a natural ligand of CD28 (B7-1, B7-2) can be presented to T cells in a form attached to a solid phase surface, such as beads. The B7 molecules, fragments thereof or modified forms thereof capable of binding to CD28 and costimulating the T cells (e.g., B7 fusion proteins) can be prepared as described for the soluble B7 forms. These molecules can then be attached to the solid phase surface via several methods. For example the B7 molecules can be crosslinked to the beads via covalent modification using tosyl linkage. In this method, B7 molecules or B7 fusion proteins are in 0.,05M borate buffer, pH 9.5 and added to tosyl activated magnetic immunobeads (Dynal Inc., Great Neck, N.Y.) according to manufacturer's instructions. After a 24 hr incubation at 22° C., the beads are collected and washed extensively. It is not mandatory that immunmagnetic beads be used, as other methods are also satisfactory. For example, the B7 molecules may also be immobilized on polystyrene beads or culture vessel surfaces. Covalent binding of the B7 molecules or B7Ig fusion proteins to the solid phase surface is preferable to adsorption or capture by a secondary monoclonal antibody. B7Ig fusion proteins can be attached to the solid phase surface through anti-human IgG molecules bound to the solid phase surface. In particular, beads to which anti-human IgG molecules are bound can be obtained from Advanced Magnetics, Inc. These beads can then be incubated with the B7Ig fusion proteins in an appropriate buffer such as PBS for about an hour at 5° C., and the uncoupled B7Ig proteins removed by washing the beads in a buffer, such as PBS.

It is also possible to attach the B7 molecules to the solid phase surface through an avidin- or streptavidin-biotin complex. In this particular embodiment, the soluble B7 molecule is first crosslinked to biotin and then reacted with the solid phase surface to which avidin or streptavidin molecules are bound. It is also possible to crosslink the B7 molecules with avidin or streptavidin and to react these with a solid phase surface that is covered with biotin molecules.

The amount of B7 molecules attached to the solid phase surface can be determined by FACS analysis if the solid phase surface is that of beads or by ELISA if the solid phase surface is that of a tissue culture dish. Antibodies reactive with the B7 molecules, such as mAb BB1, mAb IT2, and mAb 133 can be used in these assays.

In a specific embodiment, the stimulatory form of a B7 molecule is attached to the same solid phase surface as the agent that stimulates the TCR/CD3 complex, such as an anti-CD3 antibody. In addition to anti-CD3, other antibodies that bind to receptors that mimic antigen signals may be used, for example, the beads or other solid phase surface may be coated with combinations of anti-CD2 and a B7 molecule.

In a typical experiment, B7-coated beads or beads coated with B7 molecules and an agent that stimulates the TCR/CD3 complex will be added at a ratio of 3 beads per T cell.

Agents Which Act Intracellularly to Stimulate a Signal Associated With CD28 Ligation In another embodiment of the invention, an activated population of CD4$^+$ T cells is stimulated to proliferate by contacting the T cells with an agent which acts intracellularly to stimulate a signal in the T cell mediated by ligation of an accessory molecule, such as CD28. The term "agent", as used herein, is intended to encompass chemicals and other pharmaceutical compounds which stimulate a costimulatory or other signal in a T cell without the requirement for an interaction between a T cell surface receptor and a costimulatory molecule or other ligand. For example, the agent may act intracellularly to stimulate a signal associated with CD28 ligation. In one embodiment, the agent is a non-proteinaceous compound. As the agent used in the method is intended to bypass the natural receptor:ligand stimulatory mechanism, the term agent is not intended to include a cell expressing a natural ligand. Natural ligands for CD28 include members of the B7 family of proteins, such as B7-1(CD80) and B7-2 (CD86).

It is known that CD28 receptor stimulation leads to the production of D-3 phosphoinositides in T cells and that inhibition of the activity of phosphatidylinositol 3-kinase (PI3K) in a T cell can inhibit T cell responses, such as lymphokine production and cellular proliferation. Protein tyrosine phosphorylation has also been shown to occur in T cells upon CD28 ligation and it has been demonstrated that a protein tyrosine kinase inhibitor, herbimycin A, can inhibit CD28-induced IL-2 production (Vandenberghe, P. et al. (1992) *J. Exp. Med.* 175:951–960; Lu, Y. et al. (1992) *J. Immunol.* 149:24–29). Thus, to selectively expand a population of CD4$^+$ T cells, the CD28 receptor mediated pathway can be stimulated by contacting T cells with an activator of PI3K or an agent which stimulates protein tyrosine phosphorylation in the T cell, or both. An activator of PI3K can be identified based upon its ability to stimulate production of at least one D-3 phosphoinositide in a T cell. The term "D-3 phosphoinositide" is intended to include derivatives of phosphatidylinositol that are phosphorylated at the D-3 position of the inositol ring and encompasses the compounds phosphatidylinositol(3)-monophosphate (PtdIns(3)P), phosphatidylinositol(3,4)-bisphosphate (PtdIns(3,4)P$_2$), and phosphatidylinositol(3,4,5)-trisphosphate (PtdIns(3,4,5)P$_3$). Thus, in the presence of a PI3K activator, the amount of a D-3 phosphoinositide in the T cell is increased relative to the amount of the D-3 phosphoinositide in the T cell in the absence of the substance. Production of D-3 phosphoinositides (e.g., PtdIns(3)P, PtdIns(3,4)P$_2$ and/or PtdIns(3,4,5)P$_3$) in a T cell can be assessed by standard methods, such as high pressure liquid chromatography or thin layer chromatography, as discussed above. Similarly, protein tyrosine phosphorylation can be stimulated in a T cell, for example, by contacting the T cell with an activator of protein tyrosine kinases, such as pervanadate (see O'Shea, J. J. et al. (1992) *Proc. Natl. Acad. Sci. USA* 89:10306–103101; and Secrist, J. P. (1993) *J. Biol. Chem.* 268:5886–5893). Alternatively, the T cell can be contacted with an agent which inhibits the activity of a cellular protein tyrosine phosphatase, such as CD45, to increase the net amount of protein tyrosine phosphorylation in the T cell. Any of these agents can be used to expand an activated population of CD4$^+$ T cells in accordance with the methods described herein.

Techniques for Expansion of CD8$^+$ T Cells

Figure 8:
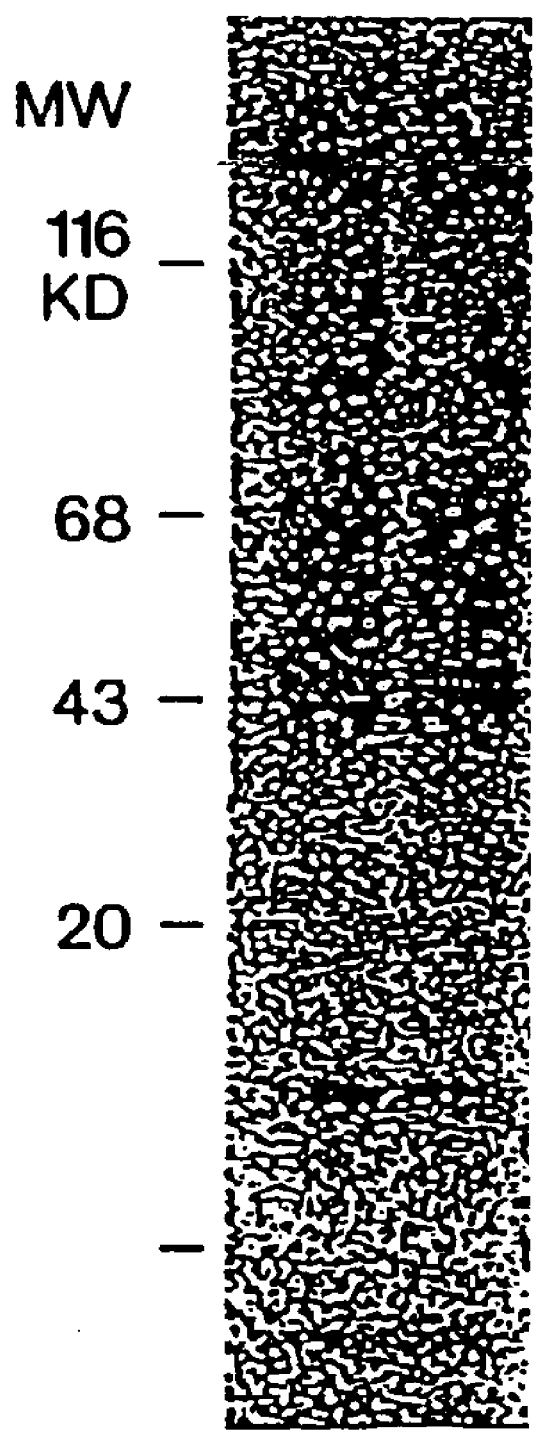
FIG. 8 is a photograph depicting immunoprecipitation analysis of detergent lysates of surface labeled human activated T cells indicating that monoclonal antibody ES5.2D8 reacts with a 27 kD cell surface protein.

In order to induce proliferation and expand a population of CD8$^+$ T cells, an activated population of T cells is stimulated through a 27 kD accessory molecule found on activated T cells and recognized by the monoclonal antibody ES5.2D8. As described in Example 9, a population of CD8$^+$ T cells was preferentially expanded by stimulation with an anti-CD3 monoclonal antibody and the ES5.2D8 monoclonal antibody. The monoclonal antibody ES5.2D8 was produced by immunization of mice with activated human blood lymphocytes and boosted with recombinant human CTLA4 protein produced in *E. coli*. The ES5.2D8 monoclonal antibody is of the IgG2b isotype and specifically binds to cells transfected with human CTLA4. Hybridomas producing CTLA4-specific antibody were identified by screening by ELISA against human CTLA4 protein as well as by differential FACS against wild type CHO-DG44 cells vs. CHO-105A cells, which are transfected with the human CTLA4 gene. As shown in FIG. 7, the ES5.2D8 clone reacts strongly with both activated human T cells and CHO-105A cells but not with CHO-DCA4 cells, indicating that it does indeed bind to CTLA4. Immunoprecipitation of detergent lysates of surface labeled activated human T cells revealed that ES5.2D8 also reacts with a 27 kD cell surface protein (FIG. 8). A hybridoma which produces the monoclonal antibody ES5.2D8 was deposited on Jun. 4, 1993 with the American Type Culture Collection at ATCC Deposit No. HB 11374.

Accordingly, to expand a population of CD8$^+$ T cells, an antibody, such as monoclonal antibody ES5.2D8, or other antibody which recognizes the same 27 kD ligand as ES5.2D8 can be used. As described in Example 10, the epitope recognized by the monoclonal antibody ES5.2D8 was identified by screening a phage display library (PDL). Antibodies which bind to the same epitope as the monoclonal antibody ES5.2D8 are within the scope of the invention. Such antibodies can be produced by immunization with a peptide fragment including the epitope or with the native 27 kD antigen. The term "epitope", as used herein, refers to the actual structural portion of the antigen that is immunologically bound by an antibody combining site. The term is also used interchangeably with "antigenic determinant". A preferred epitope which is bound by an antibody or other ligand which is to be used to stimulate a CD8$^+$ T cell population includes or encompasses, an amino acid sequence:

(Xaa$_1$)$_n$-Gly-Xaa$_2$-Trp-Leu-Xaa$_3$-Xaa$_4$-Asp(Glu)-(Xaa$_5$)$_n$ (SEQ ID NO: 9), wherein Xaa$_4$ may or may not be present, Xaa$_1$, Xaa$_2$, Xaa$_3$, Xaa$_4$ and Xaa$_5$ are any amino acid residue and n=0–20, more preferably 0–10, even more preferably 0–5, and most preferably 0–3. In a preferred embodiment, Xaa$_2$ is Cys, Ile or Leu, Xaa$_3$ is Leu or Arg and Xaa$_4$, if present, is Arg, Pro or Phe. As described in Example 10, the monoclonal antibody ES5.2D8, which specifically binds a 27 kD antigen on activated T cells was used to screen a cDNA library from activated T cells to isolate a clone encoding the antigen. Amino acid sequence analysis identified the antigen as CD9(SEQ ID NO: 10). In the native human CD9 molecule, epitope defined by phage display library screening is located at amino acid residues 31–37 (i.e., G L W L R F D (SEQ ID NO: 13)). Accordingly, Xaa$_1$ and Xaa$_4$ are typically additional amino acid residues found at either the amino or carboxy side, or both the amino and carboxy sides, of the core epitope in the human CD9 (the full-length amino acid sequence of which is shown in SEQ ID NO: 10). It will be appreciated by those skilled in the art that in the native protein, additional non-contiguous amino acid residues may also contribute to the conformational epitope recognized by the antibody. Synthetic peptides encompassing the epitope can be created which includes other amino acid residues flanking the core six amino acid residues (i.e., Xaa can alternatively be other amino acid residues than those found in the native CD9 protein). These flanking amino acid residues can function to alter the properties of the resulting peptide, for example to increase the solubility, enhance the immunogenicity or promote dimerization of the resultant peptide. When the peptide is to be used as an immunogen, one or more charged amino acids (e.g., lysine, arginine) can be included to increase the solubility of the peptide and/or enhance the immunogenicity of the peptide. Alternatively, cysteine residues can be included to increase the dimerization of the resulting peptide.

Other embodiments of the invention pertain to expansion of a population of CD8$^+$ T cells by use of an agent which acts intracellularly to stimulate a signal in the T cell mediated by ligation of CD9 or other CD9-associated molecule. It is known that CD9 belongs to the TM4 superfamily of cell surface proteins which span the membrane four times (Boucheix, C. et al. (1990) *J. Biol. Chem.* 266, 117–122 and Lanza, F. et al. (1990) *J. Biol. Chem.* 266, 10638–10645). Other members of the TM4 superfamily include CD37, CD53, CD63 and TAPA-1. A role for CD9 in interacting with GTP binding proteins has been suggested (Sechafer, J. G. and Shaw, A. R. E. (1991) *Biochem. Biophys. Res. Commun.* 179, 401–406). As used herein the term "agent" encompasses chemicals and other pharmaceutical compounds which stimulate a signal in a T cell without the requirement for an interaction between a T cell surface receptor and a ligand. Thus, this agent does not bind to the extracellular portion of CD9, but rather mimics or induces an intracellular signal (e.g., second messenger) associated with ligation of CD9 or a CD9-associated molecule by an appropriate ligand. The ligands described herein (e.g., monoclonal antibody ES5.2D8) can be used to identify an intracellular signal(s) associated with T cell expansion mediated by contact of the CD9 antigen or CD9-associated molecule with an appropriate ligand (as described in the Examples) and examining the resultant intracellular signalling that occurs (e.g., protein tyrosine phosphorylation, calcium influx, activation of serine/threonine and/or tyrosine kinases, phosphatidyl inositol metabolism, etc.). An agent which enhances an intracellular signal associated with CD9 or a CD9-associated molecule can then be used to expand $CD8^+$ T cells. Alternatively, agents (e.g., small molecules, drugs, etc.) can be screened for their ability to inhibit or enhance T cell expansion using a system such as that described in the Examples.

Techniques for Expansion of Antigen Specific T Cells

In yet another aspect of the invention, methods for expanding a population of antigen specific T cells are provided. To produce a population of antigen specific T cells, T cells are contacted with an antigen in a form suitable to trigger a primary activation signal in the T cell, i.e., the antigen is presented to the T cell such that a signal is triggered in the T cell through the TCR/CD3 complex. For example, the antigen can be presented to the T cell by an antigen presenting cell in conjuction with an MHC molecule. An antigen presenting cell, such as a B cell, macrophage, monocyte, dendritic cell, Langerhan cell, or other cell which can present antigen to a T cell, can be incubated with the T cell in the presence of the antigen (e.g., a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, e.g., a virus, which presents antigens of the pathogen can be incubated with a T cell. Following antigen specific activation of a population of T cells, the cells can be expanded in accordance with the methods of the invention. For example, after antigen specificity has been established, T cells can be expanded by culture with an anti-CD3 antibody and an anti-CD28 antibody according to the methods described herein.

Production of Antibodies and Coupling of Antibodies to Solid Phase Surfaces

The term "antibody" as used herein refers to immunoglobulin molecules and immunologically active portions of immunoglobulin molecules, i.e., molecules that contain an antigen binding site which specifically binds (immunoreacts with) an antigen, such as CD3, CD28. Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544–546) which consists of a VH domain; (v) an isolated complimentarity determining region (CDR); and (vi) an $F(ab')_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) Science 242:423–426; and Huston et al. (1988) PNAS 85:5879–5883) by recombinant methods. Such single chain antibodies are also encompassed within the term "antibody". Preferred antibody fragments for use in T cell expansion are those which are capable of crosslinking their target antigen, e.g., bivalent fragments such as $F(ab')_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques as described herein and the fragments screened for utility in the same manner as described for whole antibodies. An antibody of the invention is further intended to include bispecific and chimeric molecules having a desired binding portion (e.g., CD28).

The language "a desired binding specificity for an epitope", as well as the more general language "an antigen binding site which specifically binds (immunoreacts with)", refers to the ability of individual antibodies to specifically immunoreact with a T cell surface molecule, e.g., CD28. That is, it refers to a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody which binds specifically to a particular epitope is referred to as a "specific antibody".

"Antibody combining site", as used herein, refers to that structural portion of an antibody molecule comprised of a heavy and light chain variable and hypervariable regions that specifically binds (immunoreacts with) antigen. The term "immunoreact" or "reactive with" in its various forms is used herein to refer to binding between an antigenic determinant-containing molecule and a molecule containing an antibody combining site such as a whole antibody molecule or a portion thereof.

Although soluble forms of antibodies may be used to activate T cells, it is preferred that the anti-CD3 antibody be immobilized on a solid phase surface (e.g., beads). An antibody can be immobilized directly or indirectly by, for example, by a secondary antibody, to a solid surface, such as a tissue culture flask or bead. As an illustrative embodiment, the following is a protocol for immobilizing an anti-CD3 antibody on beads. It should be appreciated that the same protocol can be used to immobilize other antibodies or fragments thereof (e.g., an anti-CD28 antibody), and Ig fusion proteins, such as B7Ig fusion proteins, to beads.

Protocols

I. Pre-absorbing Goat anti-mouse IgG with OKT-3
   A) BioMag Goat anti-Mouse IgG (Advanced Magnetics, Inc., catalog number 8–4340D) is incubated with at least 200 $\mu$g of OKT-3 per $5 \times 10^8$ magnetic particles in PBS for 1 hour at 5° C.
   B) Particles are washed three time in PBS with the aid of a magnetic separation unit.
   Note: Advanced Magnetics also has an anti-Human CD3 directly conjugated (Catalog number 8-4703N) which will induce T-cell stimulation.

II. Pre-labeling Lymphocytes with OKT-3
  A) 1×10$^6$ cells (PBMC) are incubated in PBS with 10 μg/ml of OKT-3 for 15 minutes at room temperature.
  B) Cells are washed twice with PBS.
III. Binding Magnetic Particles to PBMC for Stimulation
  A) PBMC surface labeled with OKT-3 are cultured with Goat anti-Mouse IgG (see above) at one bead per cell following a 30 minute incubation at 20° C. with gentle agitation.
  B) Goat anti-Mouse IgG beads which were previously absorbed to OKT-3 are incubated with PBMC (1:1) for 30 minutes at 20° C. with gentle agitation and cultured.
IV. Binding Magnetic Particles to PBMC for Separation
  Same as above (Part III) except the bead to cell ratio is increased to 20:1 rather than 1:1.

Alternatively, antibodies can be coupled to a solid phase surface, e.g., beads by crosslinking via covalent modification using tosyl linkage. In one method, an antibody such as OKT3 is in 0.05M borate buffer, pH 9.5 and added to tosyl activated magnetic immunobeads (Dynal Inc., Great Neck, N.Y.) according to the manufacturer's instructions. After a 24 hr incubation at 22° C., the beads are collected and washed extensively. It is not mandatory that immunomagnetic beads be used, as other methods are also satisfactory.

To practice the method of the invention, a source of T cells is obtained from a subject. The term subject is intended to include living organisms in which an immune response can be elicited, e.g., mammals. Examples of subjects include humans, dogs, cats, mice, rats, and transgenic species thereof. T cells can be obtained from a number of sources, including peripheral blood leukocytes, bone marrow, lymph node tissue, spleen tissue, and tumors. Preferably, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through a PERCOLL™ gradient. A specific subpopulation of T cells, such as CD28$^+$, CD4$^+$, CD8$^+$, CD28RA$^+$, and CD28RO$^+$ T cells, can be further isolated by positive or negative selection techniques. For example, negative selection of a T cell population can be accomplished with a combination of antibodies directed to surface markers unique to the cells negatively selected. A preferred method is cell sorting via negative magnetic immunoadherence which utilizes a cocktail of monoclonal antibodies directed to cell surface markers present on the cells negatively selected. For example, to isolate CD4$^+$ cells, a monoclonal antibody cocktail typically includes antibodies to CD14, CD20, CD11b, CD16, HLA-DR, and CD8. Additional monoclonal antibody cocktails are provided in Table 1.

The process of negative selection results in an essentially homogenous population of CD28$^+$, CD4$^+$ or CD8$^+$ T cells. The T cells can be activated as described herein, such as by contact with a anti-CD3 antibody immobilized on a solid phase surface or an anti-CD2 antibody, or by contact with a protein kinase C activator (e.g., bryostatin) in conjunction with a calcium ionophore. To stimulate an accessory molecule on the surface of the T cells, a ligand which binds the accessory molecule is employed. For example, a population of CD4$^+$ cells can be contacted with an anti-CD3 antibody and an anti-CD28 antibody, under conditions appropriate for stimulating proliferation of the T cells. Similarly, to stimulate proliferation of CD8$^+$ T cells, an anti-CD3 antibody and the monoclonal antibody ES5.2D8 can be used. Conditions appropriate for T cell culture include an appropriate media (e.g., Minimal Essential Media or RPMI Media 1640) which may contain factors necessary for proliferation and viability, including animal serum (e.g., fetal bovine serum) and antibiotics (e.g., penicillin streptomycin). The T cells are maintained under conditions necessary to support growth, for example an appropriate temperature (e.g., 37° C.) and atmosphere (e.g., air plus 5% $CO_2$).

The primary activation signal and the costimulatory signal for the T cell can be provided by different protocols. For example, the agents providing each signal can be in solution or coupled to a solid phase surface. When coupled to a solid phase surface, the agents can be coupled to the same solid phase surface (i.e., in "cis" formation) or to separate surfaces (i.e., in "trans" formation). Alternatively, one agent can be coupled to a solid phase surface and the other agent in solution. In one embodiment, the agent providing the costimulatory signal is bound to a cell surface and the agent providing the primary activation signal is in solution or coupled to a solid phase surface. In a preferred embodiment, the two agents are coupled to beads, either to the same bead, i.e., in "cis", or to separate beads, i.e., in "trans". Alternatively, the agent providing the primary activation signal is an anti-CD3 antibody and the agent providing the costimulatory signal is an anti-CD28 antibody; both agents are coupled to the same beads. In this embodiment, it has been determined that the optimal ratio of each antibody bound to the beads for CD4$^+$ T cell expansion and T cell growth for up to at least 50 days is a 1:1 ratio. However, ratios from 1:9 to 9:1 can also be used to stimulate CD2$^+$ T cell expansion. The ratio of anti-CD3 and anti-CD28 coated (with a ratio of 1:1 of each antibody) beads to T cells that yield T cell expansion can vary from 1:3 to 3:1, with the optimal ratio being 3:1 beads per T cell. Moreover, it has been determined that when T cells are expanded under these conditions, they remain polyclonal.

To maintain long term stimulation of a population of T cells following the initial activation and stimulation, it is necessary to separate the T cells from the activating stimulus (e.g., the anti-CD3 antibody) after a period of exposure. The T cells are maintained in contact with the co-stimulatory ligand throughout the culture term. The rate of T cell proliferation is monitored periodically (e.g., daily) by, for example, examining the size or measuring the volume of the T cells, such as with a Coulter Counter. A resting T cell has a mean diameter of about 6.8 microns. Following the initial activation and stimulation and in the presence of the stimulating ligand, the T cell mean diameter will increase to over 12 microns by day 4 and begin to decrease by about day 6. When the mean T cell diameter decreases to approximately 8 microns, the T cells are reactivated and restimulated to induce further proliferation of the T cells. Alternatively, the rate of T cell proliferation and time for T cell restimulation can be monitored by assaying for the presence of cell surface molecules, such as B7-1, B7-2, which are induced on activated T cells. As described in Example 5, it was determined that CD4$^+$ T cells do not initially express the B7-1 receptor, and that with culture, expression is induced. Further, the B7-1 expression was found to be transient, and could be re-induced with repeated anti-CD3 restimulation. Accordingly, cyclic changes in B7-1 expression can be used as a means of monitoring T cell proliferation; where decreases in the level of B7-1 expression, relative to the level of expression following an initial or previous stimulation or the level of expression in an unstimulated cell, indicates the time for restimulation.

For inducing long term stimulation of a population of CD4$^+$ or CD8$^+$ T cells, it may be necessary to reactivate and restimulate the T cells with a anti-CD3 antibody and an anti-CD28 antibody or monoclonal antibody ES5.2D8 several times to produce a population of $CD4^+$ or $CD8^+$ cells increased in number from about 10- to about 1,000-fold the original T cell population. Using this methodology, it is possible to get increases in a T cell population of from about 100- to about 100,000-fold an original resting T cell population. Moreover, as described in Example 6, T cells expanded by the method of the invention secrete high levels of cytokines (e.g., IL-2, IFNγ, IL-4, GM-CSF and TNFα) into the culture supernatants. For example, as compared to stimulation with IL-2, $CD4^+$ T cells expanded by use of anti-CD3 and anti-CD28 costimulation secrete high levels of GM-CSF and TNFα into the culture medium. These cytokines can be purified from the culture supernatants or the supernatants can be used directly for maintaining cells in culture. Similarly, the T cells expanded by the method of the invention together with the culture supernatant and cytokines can be administered to support the growth of cells in vivo. For example, in patients with tumors, T cells can be obtained from the individual, expanded in vitro and the resulting T cell population and supernatant, including cytokines such as TNFα, can be readministered to the patient to augment T cell growth in vivo.

Although the antibodies used in the methods described herein can be readily obtained from public sources, such as the ATCC, antibodies to T cell surface accessory molecules, the CD3 complex, or CD2 can be produced by standard techniques. Methodologies for generating antibodies for use in the methods of the invention are described in further detail below.

Specific Methodology for Antibody Production

A. The Immunogen. The term "immunogen" is used herein to describe a composition containing a peptide or protein as an active ingredient used for the preparation of antibodies against an antigen (e.g., CD3, CD28). When a peptide or protein is used to induce antibodies it is to be understood that the peptide can be used alone, or linked to a carrier as a conjugate, or as a peptide polymer.

To generate suitable antibodies, the immunogen should contain an effective, immunogenic amount of a peptide or protein, optionally as a conjugate linked to a carrier. The effective amount of peptide per unit dose depends, among other things, on the species of animal inoculated, the body weight of the animal and the chosen immunization regimen as is well known in the art. The immunogen preparation will typically contain peptide concentrations of about 10 micrograms to about 500 milligrams per immunization dose, preferably about 50 micrograms to about 50 milligrams per dose. An immunization preparation can also include an adjuvant as part of the diluent. Adjuvants such as complete Freund's adjuvant (CFA), incomplete Freund's adjuvant (IFA) and alum are materials well known in the art, and are available commercially from several sources.

Those skilled in the art will appreciate that, instead of using natural occurring forms of the antigen (e.g., CD3, CD28) for immunization, synthetic peptides can alternatively be employed towards which antibodies can be raised for use in this invention. Both soluble and membrane bound forms of the protein or peptide fragments are suitable for use as an immunogen and can also be isolated by immunoaffinity purification as well. A purified form of protein, such as may be isolated as described above or as known in the art, can itself be directly used as an immunogen, or alternatively, can be linked to a suitable carrier protein by conventional techniques, including by chemical coupling means as well as by genetic engineering using a cloned gene of the protein.

The purified protein can also be covalently or noncovalently modified with non-proteinaceous materials such as lipids or carbohydrates to enhance immunogenecity or solubility. Alternatively, a purified protein can be coupled with or incorporated into a viral particle, a replicating virus, or other microorganism in order to enhance immunogenicity. The protein may be, for example, chemically attached to the viral particle or microorganism or an immunogenic portion thereof.

In an illustrative embodiment, a purified CD28 protein, or a peptide fragment thereof (e.g., produced by limited proteolysis or recombinant DNA techniques) is conjugated to a carrier which is immunogenic in animals. Preferred carriers include proteins such as albumins, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulins. Synthetic polyamino acids such as polylysine or polyarginine are also useful carriers. With respect to the covalent attachment of CD28 protein or peptide fragments to a suitable immunogenic carrier, there are a number of chemical cross-linking agents that are known to those skilled in the art. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyl-oxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP).

It may also be desirable to simply immunize an animal with whole cells which express a protein of interest (e.g., CD28) on their surface. Various cell lines can be used as immunogens to generate monoclonal antibodies to an antigen, including, but not limited to T cells. For example, peripheral blood T cells can be obtained from a subject which constituitively express CD28, but can be activated in vitro with anti-CD3 antibodies, PHA or PMA. Alternatively, an antigen specific (e.g., alloreactive) T cell clone can be activated to express CD28 by presentation of antigen, together with a costimulatory signal, to the T cell. Whole cells that can be used as immunogens to produce CD28 specific antibodies also include recombinant transfectants. For example, COS and CHO cells can be reconstituted by transfection with a CD28 cDNA to produce cells expressing CD28 on their surface. These transfectant cells can then be used as immunogens to produce anti-CD28 antibodies. Other examples of transfectant cells are known, particularly eukaryotic cells able to glycosylate the CD28 protein, but any procedure that works to express transfected CD28 genes on the cell surface could be used to produce the whole cell immunogen.

Alternative to a CD28-expressing cell or an isolated CD28 protein, peptide fragments of CD28 or other surface antigen such as CD9 can be used as immunogens to generate antibodies. For example, the CD9 epitope bound by the ES5.2D8 monoclonal antibody comprises an amino acid sequence: $(Xaa_1)_n$-Gly-$Xaa_2$-Trp-Leu-$Xaa_3$-$Xaa_4$-Asp (Glu)-$(Xaa_5)_n$ (SEQ ID NO: 9), wherein $Xaa_4$ may or may not be present, $Xaa_1$, $Xaa_2$, $Xaa_3$, $Xaa_4$ and $Xaa_5$ are any amino acid residue and n=0–20, more preferably 0–10, even more preferably 0–5, and most preferably 0–3. In a preferred embodiment, Xaa$_2$ is Cys, Ile or Leu, Xaa$_3$ is Leu or Arg and Xaa$_4$, if present, is Arg, Pro or Phe. Thus, a peptide having the amino acid sequence of SEQ ID NO: 5 can be used as an immunogen. Accordingly, the invention further encompasses an isolated CD9 peptide comprising an amino acid sequence: (Xaa$_1$)$_n$-Gly-Xaa$_2$-Trp-Leu-Xaa$_3$-Xaa$_4$-Asp (Glu)-(Xaa$_5$)$_n$(SEQ ID NO: 9), wherein Xaa$_4$ may or may not be present, Xaa$_1$, Xaa$_2$, Xaa$_3$, Xaa$_4$ and Xaa$_5$ are any amino acid residue and n=0–20, more preferably 0–10, even more preferably 0–5, and most preferably 0–3. In a preferred embodiment, Xaa$_2$ is Cys, Ile or Leu, Xaa$_3$ is Leu or Arg and Xaa$_4$, if present, is Arg, Pro or Phe. Alternatively, it has been found that the ES5.2D8 monoclonal antibody cross-reacts with a number of other peptide sequences (determined by phage display technology as described in Example 3). Examples of these other peptide sequences are shown below:

```
                          2D8#2   (SEQ ID NO:5)
    H Q F C D H W G C W L L R E T H I F T P

2D8#4   (SEQ ID NO:6)
    H Q F C D H W G C W L L R E T H I F T P

2D8#10  (SEQ ID NO:7)
    H Q F C D H W G C W L L R E T H I F T P

2D8#6   (SEQ ID NO:8)
    L R L V L E D P G I W L R P D Y F F P A (phage 2D8#2, 4, 10; SEQ ID NO:11)
    G C W L L R E (phage 2D8#6; SEQ ID NO:12)
    G I W L R P D (CD9 sequence; SEQ ID NO:13)
    G L W L R F D
```

Any of these peptides, or other peptides containing a stretch of seven amino acids bracketed in bold type (representing the epitope bound by the antibody) possibly flanked by alternative amino acid residues, can also be used as immunogens to produce an antibody for use in the methods of the invention and are encompassed by the invention. For use as immunogens, peptides can be modified to increase solubility and/or enhance immunogenicity as described above.

B. Polyclonal Antibodies. Polycolonal antibodies to a purified protein or peptide fragment thereof can generally be raised in animals by multiple subcutaneous (sc) or intraperitoneal (ip) injections of an appropriate immunogen, such as the extracellular domain of the protein, and an adjuvant. A polyclonal antisera can be produced, for example, as described in Lindsten, T. et al. (1993) *J. Immunol.* 151:3489–3499. In an illustrative embodiment, animals are typically immunized against the immunogenic protein, peptide or derivative by combining about 1 µg to 1 mg of protein with Freund's complete adjuvant and injecting the solution intradermally at multiple sites. One month later the animals are boosted with ⅕ to ¹⁄₁₀ the original amount of immunogen in Freund's complete adjuvant (or other suitable adjuvant) by subcutaneous injection at multiple sites. Seven to 14 days later, the animals are bled and the serum is assayed for anti-protein or peptide titer (e.g., by ELISA). Animals are boosted until the titer plateaus. Also, aggregating agents such as alum can be used to enhance the immune response.

Such mammalian-produced populations of antibody molecules are referred to as "polyclonal" because the population comprises antibodies with differing immunospecificities and affinities for the antigen. The antibody molecules are then collected from the mammal (e.g., from the blood) and isolated by well known techniques, such as protein A chromatography, to obtain the IgG fraction. To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

C. Monoclonal Antibodies. The term "monoclonal antibody" or "monoclonal antibody composition", as used herein, refers to a population of antibody molecules that contain only one species of an antigen binding site capable of immunoreacting with a particular epitope of an antigen. A monoclonal antibody composition thus typically displays a single binding affinity for a particular protein with which it immunoreacts. Preferably, the monoclonal antibody used in the subject method is further characterized as immunoreacting with a protein derived from humans.

Monoclonal antibodies useful in the methods of the invention are directed to an epitope of an antigen(s) on T cells, such that complex formation between the antibody and the antigen (also referred to herein as ligation) induces stimulation and T cell expansion. A monoclonal antibody to an epitope of an antigen (e.g., CD3, CD28) can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. (1983) *Immunol Today* 4:72), EBV-hybridoma technique (Cole et al. (1985), *Monoclonal Antibodies and Cancer Therapy*, Alan R. Liss, Inc., pp. 77–96), and trioma techniques. Other methods which can effectively yield monoclonal antibodies useful in the present invention include phage display techniques (Marks et al. (1992) *J Biol Chem* 16007–16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495–97; Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75). Thus, the monoclonal antibody compositions of the present invention can be produced by the following method, which comprises the steps of:

(a) Immunizing an animal with a protein (e.g., CD28) or peptide thereof. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of the antigen (e.g., CD28).

These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications*, Hurell (ed.) pp. 51–52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) Virol. 8:396) supplemented with 4.5 gm/l glucose, 20 mM glutamine, and 20% fetal caf serum. An exemplary inbred mouse strain is the Balb/c.

D. Combinatorial Antibodies. Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with an appropriate immunogen (e.g., CD3, CD28) as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281. ) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combinantion, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no.

240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370–1372; Hay et al. (1992) Hum Antibod Hybridomas 3:81–85; Huse et al. (1989) Science 246:1275–1281; Griffths et al. (1993) EMBO J 12:725–734; Hawkins et al. (1992) J Mol Biol 226:889–896; Clackson et al. (1991) Nature 352:624–628; Gram et al. (1992) PNAS 89:3576–3580; Garrad et al. (1991) Bio/Technology 9:1373–1377; Hoogenboom et al. (1991) Nuc Acid Res 19:4133–4137; and Barbas et al. (1991) PNAS 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552–554, complete $V_H$ and $V_L$ domains of an antibody, joined by a flexible (Gly4-Ser)$_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the protein, or peptide fragment thereof, to identify and isolate packages that express an antibody having specificity for the protein. Nucleic acid encoding the selected antibody can be recovered from the display package (e.g., from the phage genome) and subcloned into other expression vectors by standard recombinant DNA techniques.

E. Hybridomas and Methods of Preparation. Hybridomas useful in the present invention are those characterized as having the capacity to produce a monoclonal antibody which will specifically immunoreact with an antigen of interest (e.g., CD3, CD28). Methods for generating hybridomas that produce, e.g., secrete, antibody molecules having a desired immunospecificity, e.g., having the ability to immunoreact with the CD28 antigen, and/or an identifiable epitope of CD28 are well known in the art. Particularly applicable is the hybridoma technology described by Niman et al. (1983) PNAS 80:4949–4953; and by Galfre et al. (1981) Meth. Enzymol. 73:3–46.

Uses of the Methods of the Invention

The method of this invention can be used to selectively expand a population of $CD28^+$, $CD4^+$, $CD8^+$, $CD28RA^+$, or $CD28RO^+$ T cells for use in the treatment of infectious disease, cancer and immunotherapy. As a result of the method described herein, a population of T cells which is polyclonal with respect to antigen reactivity, but essentially homogeneous with respect to either $CD4^+$ or $CD8^+$ can be produced. In addition, the method allows for the expansion of a population of T cells in numbers sufficient to reconstitute an individual's total $CD4^+$ or $CD8^+$ T cell population (the population of lymphocytes in an individual is approximately $10^{11}$). The resulting T cell population can be genetically transduced and used for immunotherapy or can be used in methods of in vitro analyses of infectious agents. For example, a population of tumor-infiltrating lymphocytes can be obtained from an individual afflicted with cancer and the T cells stimulated to proliferate to sufficient numbers. The resulting T cell population can be genetically transduced to express tumor necrosis factor (TNF) or other factor and restored to the individual.

One particular use for the $CD4^+$ T cells expanded by the method of the invention is in the treatment of HIV infection in an individual. Prolonged infection with HIV eventually results in a marked decline in the number of $CD4^+$ T lymphocytes. This decline, in turn, causes a profound state of immunodeficiency, rendering the patient susceptible to an array of life threatening opportunistic infections. Replenishing the number of $CD4^+$ T cells to normal levels may be expected to restore immune function to a significant degree. Thus, the method described herein provides a means for selectively expanding $CD4^+$ T cells to sufficient numbers to reconstitute this population in an HIV infected patient. It may also be necessary to avoid infecting the T cells during long-term stimulation or it may desirable to render the T cells permanently resistant to HIV infection. There are a number of techniques by which T cells may be rendered either resistant to HIV infection or incapable of producing virus prior to restoring the T cells to the infected individual. For example, one or more anti-retroviral agents can be cultured with $CD4^+$ T cells prior to expansion to inhibit HIV replication or viral production (e.g., drugs that target reverse transcriptase and/or other components of the viral machinery, see e.g., Chow et al. (1993) Nature 361, 650–653).

Several methods can be used to genetically transduce T cells to produce molecules which inhibit HIV infection or replication. For example, in one embodiment, T cells can be genetically transduced to produce transdominant inhibitors, which are mutated, nonfunctional forms of normal HIV gene products. Transdominant inhibitors function to oligomerize or compete for binding with the wild type HIV proteins. Several transdominant inhibitors have been derived from HIV proteins including tat, rev, and gag. The function of tat is to enhance the transcription of viral genes by binding to the trans activation response element (tar) found in the promoter region of most HIV genes. Rev, through binding to the rev response element (RRE) found at the 5' end of unspliced HIV transcripts, facilitates the transport of unprocessed mRNA from the nucleus to the cytoplasm for packaging into virions. Gag is first synthesized as a single polypeptide and subsequently cleaved by a virus-encoded protease to yield three structural proteins, p15, p17, and p24. Transdominant inhibitors derived from these gene products have been demonstrated to inhibit infection of cells cultured with lab pet HIV isolates. One example of a transdominant inhibitor which appears to act by forming nonfunctional multimers with wild-type Rev is RevM10. RevM10 construct has blocked infection of CEM cells by HTLV-IIIB for up to 28 days (Malim et al. JEM 176:1197, Bevec et al. PNAS 89:9870). In these studies, RevM10 failed to demonstrate adverse effect on normal T cell function as judged by the criteria of growth rate and IL-2 secretion.

In another approach T cells can be transduced to produce molecules known as "molecular decoys" which are binding elements for viral proteins critical to replication or assembly, such as TAR. High level retrovirus-mediated expression of TAR in CEM SS cells has been found to effectively block the ARV-2 HIV isolate, as measured by RT assay (Sullenger et al. Cell 63:601). Importantly, it also blocked SIV (SIVmac251) infection, suggesting that inhibition of HIV infection with molecular decoys may be generally applicable to various isolates and thereby alleviate the problem of hypervariability. Further, it has been demonstrated that TAR expression has no discernible effects on cell viability (Sullenger et al. *J. Virol.* 65:6811). Another "molecular decoy" which T cells can be transduced to produce is a soluble CD4 tagged at the carboxy terminus with a KDEL (lysine-aspartic acid-glutamic acid-leucine) sequence, a signal for ER retention (Buonocore and Rose, *PNAS* 90:2695) (*Nature* 345:625). The sCD4-KDEL gene expression is driven by the HIV LTR. H9 cells transduced with the sCD4-KDEL construct show up regulation of expression of intracellular CD4 upon HIV infection. This strategy effectively blocked production of HIV MN for up to 60 days post infection. The proposed advantage of this inhibitor is that the virus should not be able to escape it's effect by mutating because CD4 binding is essential for HIV infectivity.

T cells can also be transduced to express antisense molecules and ribozyme which block viral replication or infection. Viral replication can be inhibited with a variety of antisense strategies. One particular ribozyme which cleaves HIV integrase (Sioud and Drlica. *PNAS* 88:7303), has been developed and may offer an approach to blocking infection as opposed to merely viral production.

Another approach to block HIV infection involves transducing T cells with HIV-regulated toxins. Two examples of this type of approach are the diphtheria toxin A gene (Harrison et al. *AIDS Res. Hum. Retro.* 8:39) and the herpes simplex virus type 1 thymidine kinase gene (HSV TK) (Caruso and Klatzmann, *PNAS* 89:182). In both cases, transcription was under the control of HIV regulatory sequences. While the diphtheria toxin is itself toxic, the HSV TK requires the addition of acyclovir to kill infected cells. For example the use of HSV TK followed by the addition of 10 µm acyclovir for 17 days totally blocks HIV infection of HUT 78 cells for up to 55 days of culture.

It has been demonstrated that when $CD4^+$ T cells from an HIV infected individual are stimulated with anti-CD3 and anti-CD28 antibodies attached to a solid phase support, such as beads, the cell culture proliferates exponentially and the amount of HIV particles produced is significantly reduced as compared to conventional methods for stimulating T cells, such as with PHA and IL-2 (see Example 16). Thus, when $CD4^+$ T cells from an HIV infected individual are expanded ex vivo with anti-CD3 and anti-CD28 on a solid phase surface, the presence of anti-retroviral agents may not be required in the culture to limit replication of HIV. Since anti-retroviral drugs have toxic effects on cells, no anti-retroviral agent or reduced amounts of these agents to the T cell culture will result in expansion to higher cell numbers. Thus, in a preferred embodiment of the invention, $CD4^+$ T cells from an HIV infected individual are isolated, expanded ex vivo with anti-CD3 and anti-CD28 antibody coated beads (preferably, at a ratio of 3 beads per T cell) in the absence of or in the presence of reduced amounts of anti-retroviral agents and readministered to the individual.

The invention also provides for in vivo expansion of $CD4^+$ T cells in an individual, particularly in an HIV infected individual. It has been shown that when $CD4^+$ T cells infected with HIV are cultured in vitro with anti-CD3 and anti-CD28 attached to a solid phase surface, expansion of the T cell population is obtained and the amount of HIV produced is significantly reduced compared to the amount of virus produced when the cells are stimulated with PHA and IL-2 (Example 15). Thus, in one embodiment of the invention, expansion of the population of $CD4^+$ T cells in an HIV infected individual is achieved by administration to the individual of anti-CD3 and anti-CD28 antibodies attached to a solid phase surface. This particular embodiment should be useful as a therapeutic method for increasing the number of $CD4^+$ T cells in an individual, since the expansion of the T cells will occur with limited reduced HIV replication.

The methods for stimulating and expanding a population of antigen specific T cells are useful in therapeutic situations where it is desirable to upregulate an immune response (e.g., induce a response or enhance an existing response) upon administration of the T cells to a subject. For example, the method can be used to enhance a T cell response against tumor-associated antigens. Tumor cells from a subject typically express tumor-associated antigens but may be unable to stimulate a costimulatory signal in T cells (e.g., because they lacks expression of costimulatory molecules). Thus, tumor cells can be contacted with T cells from the subject in vitro and antigen specific T cells expanded according to the method of the invention and the T cells returned to the subject. Alternatively, T cells can be stimulated and expanded as described herein to induce or enhance responsiveness to pathogenic agents, such as viruses (e.g., human immunodeficiency virus), bacteria, parasites and fungi.

The invention further provides methods to selectively expand a specific subpopulation of T cells from a mixed population of T cells. In particular, the invention provides a method to specifically enrich a population of $CD28^+$ T cells in $CD4^+$ T cells. Indeed, stimulation of a population of $CD28^+$ T cells with anti-CD3 and anti-CD28 antibodies or a natural ligand of CD28, such as B7-1 or B7-2 present on the surface of CHO cells results in expansion of the population of $CD4^+$ T cells at the expense of the $CD8^+$ T cells, which progressively die by apoptosis (see Example 15). Thus, expansion of $CD28^+$ T cells under these conditions results in a selective enrichment in $CD4^+$ T cells in long term cultures.

Another embodiment of the invention, provides a method for selectively expanding a population of either TH1 or TH2 cells or from a population of $CD4^+$ T cells. A population of $CD4^+$ T cells can be enriched in either TH1 or TH2 cells by stimulation of the T cells with a first agent which provides a primary activation signal and a second agent which provides a CD28 costimulatory signal i.e., an anti-CD28 antibody or a natural ligand for CD28, such as B7-1 or B7. For example, to selectively expand TH2 cells from a population of $CD4^+$ cells, $CD4^+$ T cells are costimulated with a natural ligand of CD28, such as B7-1 or B7-2, present on the surface of cells, such as CHO cells, to induce secretion of TH2 specific cytokines, such as IL-4 and IL-5, resulting in selective enrichment of the T cell population in TH2 cells. On the contrary, to expand TH1 cells from a population of $CD4^+$ T cells, $CD4^+$ T cells are costimulated with an anti-CD28 antibody, such as the monoclonal antibody 9.3, inducing secretion of TH1-specific cytokines, including IFN-$\gamma$, resulting in enrichment of TH1 cells over TH2 cells (Example 14).

Compositions and Kits

This invention also provides compositions and kits comprising an agent which stimulates an accessory molecule on the surface of T cells (e.g., an anti-CD28 antibody) coupled to a solid phase surface and, optionally, including an agent which stimulates a TCR/CD3 complex-associated signal in T cells (e.g., an anti-CD3 antibody) coupled to the same solid phase surface. For example, the composition can comprise an anti-CD28 antibody and an anti-CD3 antibody coupled to the same solid phase surface (e.g. bead). Alternatively, the composition can include an agent which stimulates an accessory molecule on the surface of T cells coupled to a first solid phase surface and an agent which stimulates a TCR/CD3 complex-associated signal in T cells coupled to a second solid phase surface. For example, the composition can include an anti-CD28 antibody coupled to a first bead and an anti-CD3 antibody coupled to a second bead. Kits comprising such compositions and instructions for use are also within the scope of this invention.

This invention is further illustrated by the following examples which should not be construed as limiting. The contents of all references and published patent applications cited throughout this application are hereby incorporated by reference. The following methodology described in the Materials and Methods section was used throughout the examples set forth below.

Methods and Materials

Preparation of Immobilized Anti-CD3 Antibody

Tissue culture flasks were coated with anti-CD3 monoclonal antibody. Although a number of anti-human CD3 monoclonal antibodies are available, OKT3 prepared from hybridoma cells obtained from the American Type Culture Collection was used in this procedure. For any anti-CD3 antibody the optimal concentration to be coated on tissue cultured flasks must be determined experimentally. With OKT3, the optimal concentration was determined to be typically in the range of 0.1 to 10 micrograms per milliliter. To make coating solution, the antibody was suspended in 0.05 M tris-HCl, pH 9.0 (Sigma Chemical Co., St. Louis, Mo.). Coating solution sufficient to cover the bottom of a tissue culture flask was added (Falcon, Nunc or Costar) and incubated overnight at 4° C. The flasks were washed three times with phosphate buffered saline without calcium or magnesium (PBS w/o Ca or Mg) and blocking buffer (PBS w/o Ca or Mg plus 5% bovine serum albumin) added to cover the bottom of the flask and were incubated two hours at room temperature. After this incubation, flasks were used directly or frozen for storage, leaving the blocking solution on the flask.

Isolation of Peripheral Blood Leukocytes (PBLs)

Samples were obtained by leukopheresis of healthy donors. Using sterile conditions, the leukocytes were transferred to a T800 culture flask. The bag was washed with Hanks balanced salt solution w/o calcium or magnesium (HBSS w/o) (Whittaker Bioproducts, Inc., Walkersville, Md.). The cells were diluted with HBSS w/o and mixed well. The cells were then split equally between two 200 milliliter conical-bottom sterile plastic tissue culture tubes. Each tube was brought up to 200 ml with HBSS w/o and spun at 1800 RPM for 12 minutes in a Beckman TJ-6 centrifuge. The supernatant was aspirated and each pellet resuspended in 50 ml HBSS w/o. The cells were transferred to two 50 ml conical bottom tubes and spun at 1500 RPM for eight minutes. Again the supernatant was aspirated.

To lyse the red blood cells, the cell pellets were resuspended in 50 ml of ACK lysing buffer (Biofluids, Inc., Rockville Md., Catalog #304) at room temperature with gentle mixing for three minutes. The cells were again pelleted by spinning at 1500 RPM for 8 minutes. After aspirating the supernatant, the pellets were combined into one 50 ml tube in 32 ml HBSS w/o.

Separation of the PBLs from monocytes was accomplished by centrifugation through a PERCOLL™ gradient. To prepare 1 liter of PERCOLL™ solution (PERCOLL™), 716 ml of PERCOLL™ (Pharmacia, Piscataway, N.J., Catalog #17–0891–01) was combined with 100 ml 1.5 M sodium chloride, 20 ml 1M sodium-HEPES, and 164 ml water. All reagents must be tissue culture grade and sterile filtered.

After mixing, this solution was filtered through a sterile 0.2 $\mu m^3$ filter and stored at 4° C. 24 ml of PERCOLL™ was added to each of two 50 ml conical bottom tubes. To each tube 16 ml of the cell suspension was added. The solution was mixed well by gently inverting the tubes. The tubes were spun at 2800 RPM for 30 minutes without a brake. The tubes were removed from the centrifuge, being careful not to mix the layers. The PBLs were at the bottoms of the tubes. Then, the supernatant was aspirated and the PBLs were washed in HBSS w/o by centrifuging for 8 minutes at 1500 RPM.

Cell Sorting Via Negative Magnetic Immunoadherence

The cell sorting via negative magnetic immunoadherence must be performed at 4° C. The washed cell pellets obtained from the PERCOLL™ gradients described above were resuspended in coating medium (RPMI-1640 (Bio Whittaker, Walkersville, Md., Catalog #12-167Y), 3% fetal calf serum (FCS) (or 1% human AB⁻ serum or 0.5% bovine serum albumin) 5 mM EDTA (Quality Biological, Inc., Gaithersburg, Md., Catalog #14-117-1), 2 mM L-glutamine (Bio Whittaker, Walkersville, Md., Catalog #17-905C), 20 mM HEPES (Bio Whittaker, Walkersville, Md., Catalog #17-757A), 50 $\mu$g/ml gentamicin (Bio Whittaker, Walkersville, Md., Catalog #17–905C)) to a cell density of $20 \times 10^6$ per ml. A cocktail of monoclonal antibodies directed to cell surface markers was added to a final concentration of 1 $\mu$g/ml for each antibody. The composition of this cocktail is designed to enrich for either $CD4^+$ or $CD28^+$ T cells. Thus, the cocktail will typically include antibodies to CD14, CD20, CD11b, CD16, HLA-DR, and (for $CD4^+$ cells only) CD8. (See Table 1 for a list of sorting monoclonal antibody cocktails.) The tube containing cells and antibodies was rotated at 4° for 30–45 minutes. At the end of this incubation, the cells were washed three times with coating medium to remove unbound antibody. Magnetic beads coated with goat anti-mouse IgG (Dynabeads M-450, Catalog #11006, P&S Biochemicals, Gaithersburg, Md.) and prewashed with coating medium were added at a ratio of three beads per cell. The cells and beads were then rotated for 1–1.5 hours at 4° C. The antibody-coated cells were removed using a magnetic particle concentrator according to the manufacturer's directions (MPC-1, Catalog #12001, P&S Biochemicals, Gaithersburg, Md.). The nonadherent cells were washed out of the coating medium and resuspended in an appropriate culture medium.

TABLE 1

Sorting Monoclonal Antibody Cocktails:
(Italicized mAbs are available from the ATCC)

| Cocktail | Targets | Representative mAbs |
|---|---|---|
| rt-A | CD14 | 63D3 (IgG1), 20.3 (IgM) |
|  | CD20 | 1F5 (IgG2$_a$), Leu-16 (IgG1) |
|  | CD16 | FC-2.2 (IgG2$_b$), 3G8 (IgG1) |
|  | HLA-DR | 2.06 (IgG1), HB10a (IgG) |
| rT-B | CD14 | 63D3 (IgG1), 20.3 (IgM) |
|  | CD21 | HB5 (IgG2$_a$) |
|  | CD16 | FC-2.2 (IgG2$_a$), 3G8 (IgG1) |
|  | HLA-DR | 2.06 (IgG1), HB10a (IgG) |
| r9.3-A | CD14 | 63D3 (IgG1), 20.3 (IgM) |
|  | CD20 | 1F5 (IgG2$_a$), Leu-16 (IgG1) |
|  | CD11b | OKMI (IgG2$_b$), 60.1 (IgG2$_b$) |
|  | CD16 | FC-2.2 (IgG2$_b$), 3G8 (IgG1) |
|  | HLA-DR | 2.06 (IgG1), HB10a (IgG) |
| r9.3-B | CD14 | 63D3 (IgG1), 20.3 (IgM) |
|  | CD21 | HB5 (IgG2$_a$) |
|  | CD11b | OKMI (IgG2$_b$), 60.1 (IgG2$_b$) |

TABLE 1-continued

Sorting Monoclonal Antibody Cocktails:
(Italicized mAbs are available from the ATCC)

| Cocktail | Targets | Representative mAbs |
|---|---|---|
| | CD16 | FC-2.2 (IgG2$_b$), 3G8 (IgG1) |
| | HLA-DR | 2.06 (IgG1), HB10a (IgG) |
| rCD4-A | CD14 | 63D3 (IgG1), 20.3 (IGM) |
| | CD20 | IF5 (IgG2$_a$), Leu-16 (IGg1) |
| | CD11b | OKMI (IgG2$_b$), 60.1 (IgG2$_b$) |
| | CD16 | FC-2.2 (IgG$_b$), 3G8 (IgG1) |
| | HLA-DR | 2.06 (IgG1), HB10a (IgG) |
| | CD8 | 51.1 (IgG2), G10-1.1 (IgG2$_a$), OKT8, (IgG2$_a$) |
| rCD8-B | CD14 | 63D3 (IgG1), 20.3 (IgM) |
| | CD20 | IF5 (IgG2$_a$), Leu-16 (IGg1) |
| | CD11b | OKMI (IgG2$_b$), 60.1 (IgG2$_b$) |
| | CD16 | FC-2.2 (IgG2$_b$), 3G8 (IgG1) |
| | HLA-DR | 2.06 (IgG1), HB10a (IgG) |
| | CD4 | G17-2.8 (IgG1) |
| rM0 | CD2 | 35.1 (IgG2$_a$), 9.6 (IgG2$_a$) |
| | CD20 | IF5 (IgG2$_a$), Leu-16 (IGg1) |
| rB | CD2 | 35.1 (IgG2$_a$), 9.6 (IgG2$_a$) |
| | CD14 | 63D3 (IgG1), 20.3 (IgM) |
| | CD11b | OKMI (IgG2$_b$), 60.1 (IgG2$_b$) |
| | CD16 | FC-2.2 (IgG2$_b$), 3G8 (IgG1) |

Long Term Stimulation:

Tissue culture flasks precoated with anti-CD3 monoclonal antibody were thawed and washed three times with PBS. The purified T cells were added at a density of $2\times10^6$/ml. Anti-CD28 monoclonal antibody mAb 9.3 (Dr. Jeffery Ledbetter, Bristol Myers Squibb Corporation, Seattle, Wash.) or EX5.3D10, ATCC Deposit No. HB 11373 (Repligen Corporation, Cambridge, Mass.) was added at a concentration of 1 μg/ml and cells were cultured at 37° C. overnight. The cells were then detached from the flask by forceful pipetting and transferred to a fresh untreated flask at a density of $0.5\times10^6$/ml. Thereafter, the cells were resuspended every other day by forceful pipetting and diluted to $0.5\times10^6$/ml. The mean diameter of the cells was monitored daily with a Coulter Counter 2M interfaced to a Coulter Channelyzer. Resting T cells have a mean diameter of 6.8 microns. With this stimulation protocol, the mean diameter increased to over 12 microns by day 4 and then began to decrease by about day 6. When the mean diameter decreased to about 8 microns, the cells were again stimulated overnight with anti-CD3 and anti-CD28 as above. It was important that the cells not be allowed to return to resting diameter. This cycle was repeated for as long as three months. It can be expected that the time between restimulations will progressively decrease.

EXAMPLE 1

Long Term Growth of CD4$^+$ T Cells with Anti-CD3 and Anti-CD28 Antibodies

Previous known methods to culture T cells in vitro require the addition of exogenous feeder cells or cellular growth factors (such as interleukin 2 or 4) and a source of antigen or mitogenic plant lectin. Peripheral blood CD28$^+$ T cells were isolated by negative selection using magnetic immunobeads and monoclonal antibodies as described in the Methods and Materials section above. CD4$^+$ cells were further isolated from the T cell population by treating the cells with anti-CD8 monoclonal antibody and removing the CD8$^+$ cells with magnetic immunobeads. Briefly, T cells were obtained from leukopheresis of a normal donor, and purified with FICOLL™ density gradient centrifugation, followed by magnetic immunobead sorting. The resulting CD28$^+$, CD4$^+$ T cells were cultured in defined medium (X-Vivo10 containing gentamicin and L-glutamine (Whittaker Bioproducts) at an initial density of $2.0\times10^6$/ml by adding cells to culture dishes containing plastic-adsorbed Goat anti-mouse IgG (Kirkegaard and Perry Laboratories, Gaithersburg, Md.) and anti-CD3 mAb G19–4. After 48 hours, the cells were removed and placed in flasks containing either hIL-2 (5%, CalBiochem) or anti-CD28 mAb (500 ng/ml). The cells cultured with IL-2 were fed with fresh IL-2 at 2-day intervals. Fresh medium was added to all cultures as required to maintain a cell density of $0.5\times10^6$/ml. Cells were restimulated at approximately weekly intervals by culture on plastic-adsorbed anti-CD3 mAb for 24 hours, the cells removed and placed at $1.0\times10^6$/ml in fresh medium in flasks containing either IL-2 or anti-CD28 mAb.

In the example shown in FIG. 1, the culture vessel initially contained $50\times10^6$ cells, and the cells were cultured in an optimal amount of mitogenic lectin PHA, or cultured with cyclic stimulation of plastic immobilized anti-CD3 mAb in the presence of interleukin 2 or anti-CD28 mAb 9.3. The cells cultured in PHA alone did not proliferate, with all cells dying by about day 20 of culture, demonstrating the functional absence of accessory cells. In contrast, the cells grown in anti-CD3 with IL-2 or anti-CD28 entered a logarithmic growth phase, with equal rates of growth for the first three weeks of culture. However, the anti-CD3 cultures began to diverge in growth rates during the fourth week of culture, with the IL-2 fed cells entering a plateau phase after a ~2.8 $\log_{10}$ expansion. In contrast, the cultures grown in the presence of anti-CD28 remained in logarithmic growth until the sixth week of culture, at which time there had been a ~3.8 $\log_{10}$ expansion. Thus, CD28 receptor stimulation, perhaps by anti-CD28 crosslinking, is able to stimulate the growth of CD4$^+$ T cells in the absence of fetal calf serum or accessory cells, and furthermore, about 10-fold more cells can be obtained using anti-CD28 as opposed to addition of exogenous IL-2. In repeated experiments, CD4$^+$ T cell expansion using anti-CD28 antibody consistently yielded more CD4$^+$ T cells than expansion using IL-2 (e.g., up to 1000-fold more cells). This system has the added advantage of not requiring the presence of accessory cells which may be advantageous in clinical situations where accessory cells are limiting or defective.

EXAMPLE 2

Long Term Growth of Anti-CD28-Treated T Cells In Medium Containing Fetal Calf Serum Another series of experiments tested whether the growth advantage of CD28 receptor stimulation was due to replacement of factors normally present in fetal calf serum. T cells were obtained from leukopheresis of a normal donor, and purified with FICOLL™ density gradient centrifugations, followed by magnetic immunobead sorting. The resulting CD28$^+$, CD4$^+$ T cells were cultured at an initial density of $2.0\times10^6$/ml in medium (RPMI-1640 containing 10% heat-inactivated fetal calf serum [Hyclone, Logan, Utah] and gentamicin and L-glutamine) by adding cells to culture dishes containing plastic-adsorbed OKT3. After 48 hours, the cells were removed and placed in flasks containing either hIL-2 (10% final concentration, CalBiochem) or anti-CD28 mAb 9.3 (800 ng/ml). The cells were fed with fresh medium as required to maintain a cell density of $0.5\times10^6$/ml, and restimulated at approximately weekly intervals by culture on plastic adsorbed anti-CD3 mAb for 24 hours.

Figure 2:
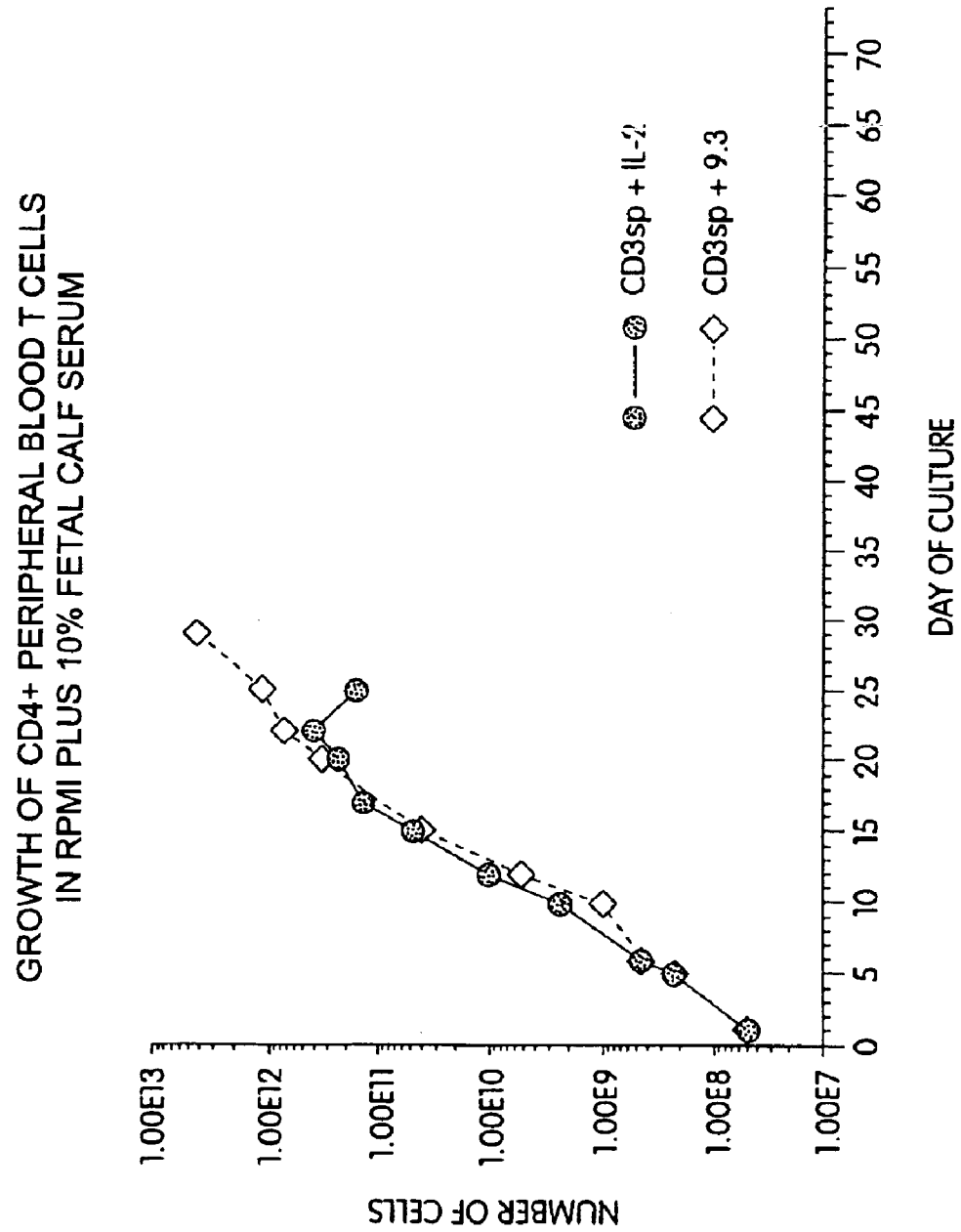
FIG. 2 depicts the growth curve of $CD4^+$ peripheral blood T cells cultured in fetal calf serum and either anti-CD3 antibodies and IL-2 (●—●) or an anti-CD3 antibody and an anti-CD28 antibody, mAb 9.3 (◊—◊).

As shown in FIG. 2, the cells entered logarithmic growth phase, with equal rates of growth for the first three weeks of culture. However, the anti-CD3 cultures began to diverge in growth rates during the fourth week of culture, with the IL-2 fed cells entering a plateau phase after a ~4.0 $\log_{10}$ expansion. In contrast, the cultures grown in the presence of anti-CD28 remained in logarithmic growth until the fifth week of culture, at which time there had been a ~5.1 $\log_{10}$ expansion. Thus, CD28 stimulation resulted in a ~125,000-fold expansion of the initial culture while IL-2 feeding resulted in a 10,000-fold expansion of cells.

EXAMPLE 3
Long Term Growth of T Cells in Phorbol Ester, Ionomycin and Anti-CD28-Stimulated T Cells Further experiments tested whether alternative methods of activating T cells would also permit CD28 stimulated growth. Pharmacologic activation of T cells with PMA and ionomycin is thought to mimic antigen receptor triggering of T cells via the TCR/CD3 complex. T cells were obtained from leukopheresis of a normal donor, and purified with sequential FICOLL™ and PERCOLL™ density gradient centrifugations, followed by magnetic immunobead sorting. The resulting $CD28^+$, $CD4^+$ T cells were cultured at an initial density of $2.0\times10^6$/ml by adding cells to culture dishes containing phorbol myristic acid (PMA 3 ng/ml, Sigma) and ionomycin (120 ng/ml, Calbiochem, lot #3710232). After 24 hours, the cells were diluted to $0.5\times10^6$/ml and placed in flasks containing either rIL-2 (50 IU/ml, Boerhinger Mannheim, lot #11844900)) or anti-CD28 mAb (1 ug/ml). The cells were fed with fresh medium as required to maintain a cell density of $0.5\times10^6$/ml, and restimulated cyclically at approximately weekly intervals by readdition of PMA and ionomycin. Fresh IL-2 was added to the IL-2 containing culture at daily intervals.

Figure 3:
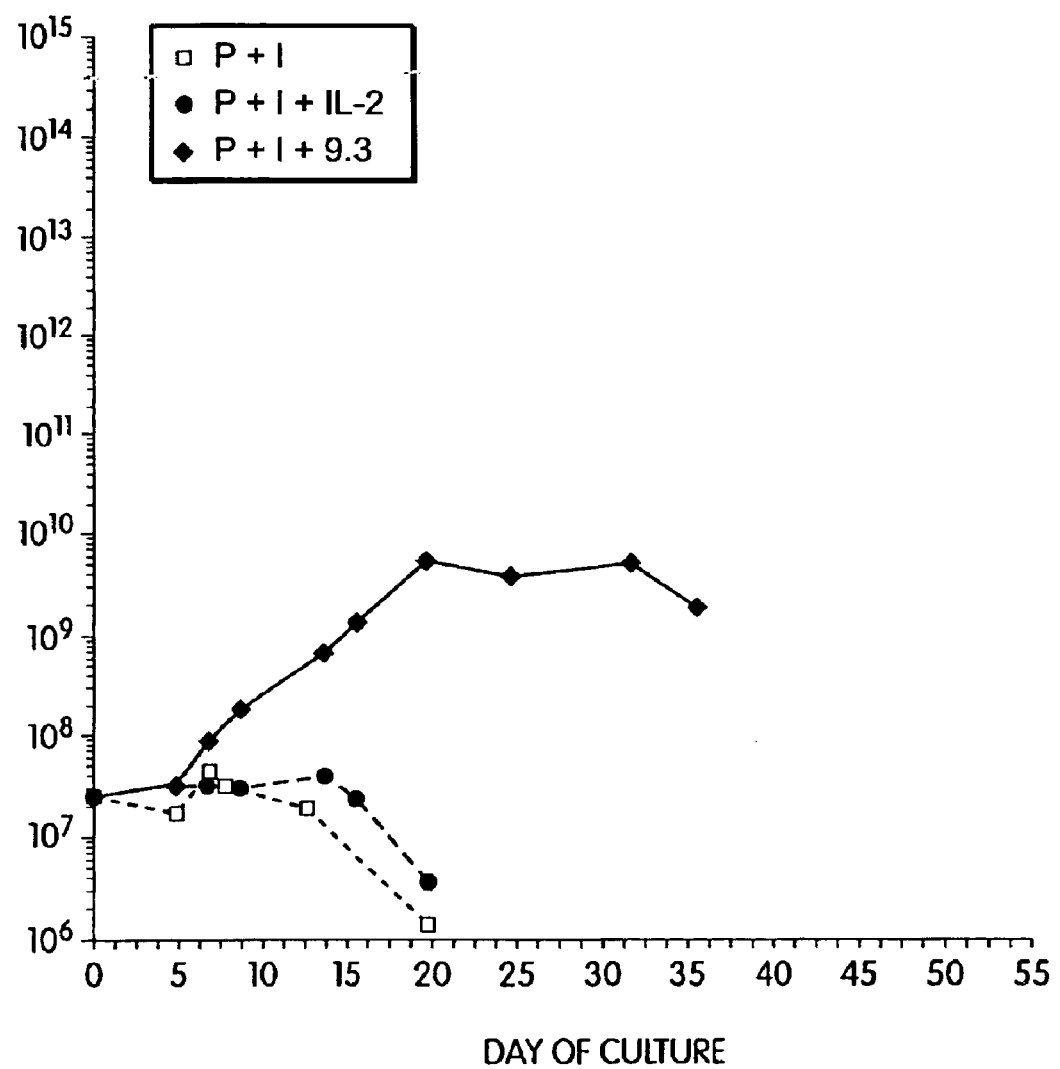
FIG. 3 depicts the growth curves of $CD4^+$ peripheral blood T cells cultured in the presence of phorbol myristic acid (PMA) and ionomycin with or without IL-2, or with an anti-CD28 antibody, mAb 9.3. The symbols are as follows: PMA and ionomycin ($P^+I$) is represented by (□); PMA, ionomycin and IL-2 ($P^+I^+IL-2$) is represented by (●); and PMA, ionomycin and anti-CD28 antibody ($P^+I^+9.3$) is represented by (♦).

The results of this experiment are shown in FIG. 3. T cells that were purified of accessory cells did not grow in cell numbers in the presence of PMA ("P" in the Figure) and ionomycin ("I" in the Figure), with or without IL-2. The cells clumped and enlarged, as indicated by size analysis, indicating the cells had been induced to enter the GI phase of the cell cycle but did not progress to DNA synthesis and cell division. In contrast, addition of CD28 mAb to PMA plus ionomycin treated cells resulted in logarithmic cell growth. Thus, anti-CD3 mAb is not required to provide T cell activation. It should be appreciated that other activators of protein kinase C, such as bryostatin or diacylglycerol can be used in place of PMA.

Figure 4:
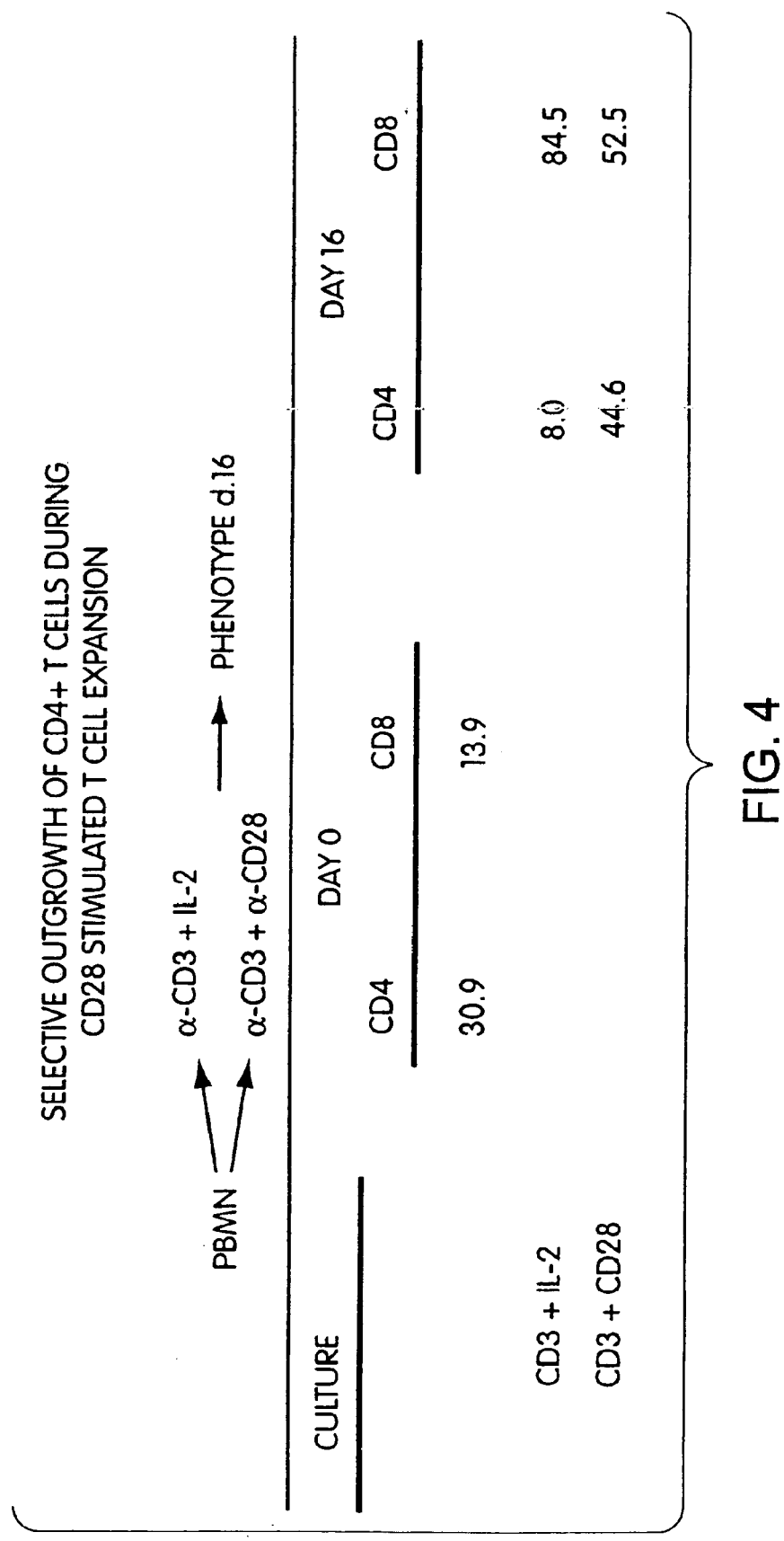
FIG. 4 is a schematic representation of the selective expansion of $CD4^+$ T cells following CD28 stimulation in comparision to T cell stimulation with IL-2.
Figure 6A:
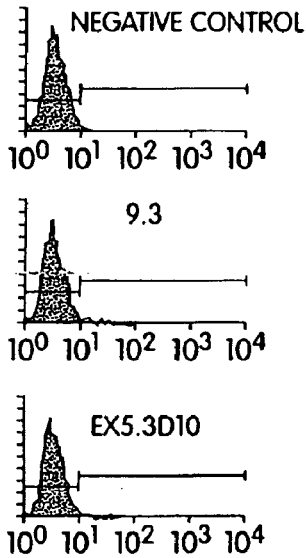
FIG. 6 shows FACS analysis of the EX5.3D10 monoclonal antibody depicting reactivity with CD28 in comparison to an anti-CD28 monoclonal antibody 9.3. The following cell lines were tested: Panel A, untransfected CHO-DG44 cells; Panel B, CHO-HH cells; Panel C, unactivated peripheral blood lymphocytes; and Panel D, Jurkat No. 7 cells.
Figure 6B:
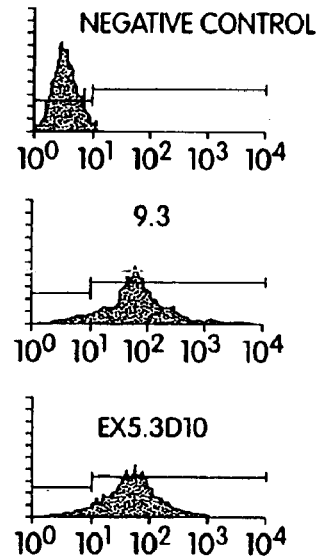
Figure 6C:
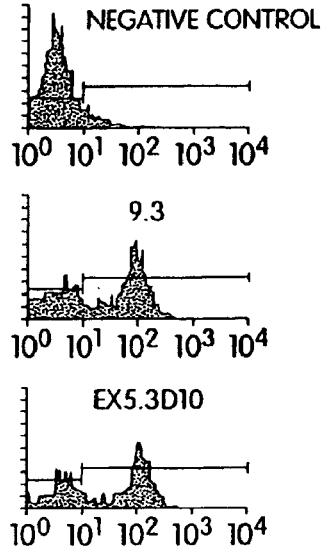
Figure 6D:
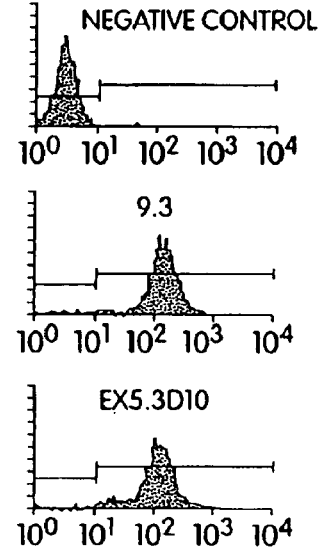
Figure 7A:
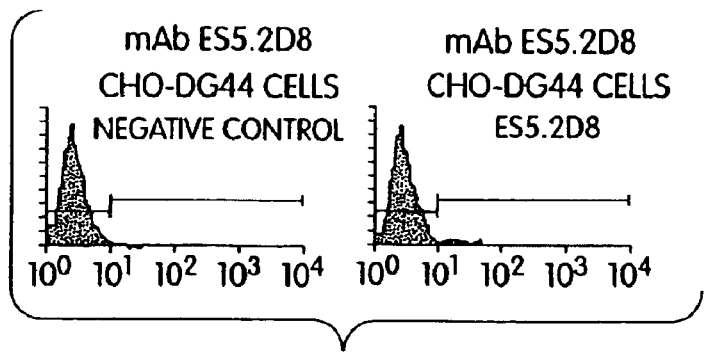
FIG. 7 shows FACS analysis of the ES5.2D8 monoclonal antibody depicting the binding reactivity with the following cell lines: Panel A, CHO-DG44 cells; Panel B, CHO-105A cells; Panel C, unactivated human peripheral blood lymphocytes; and Panel D, PMA activated peripheral blood lymphocytes.
Figure 7B:
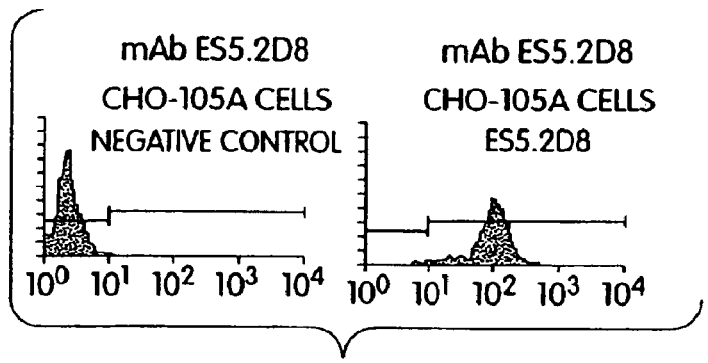
Figure 7C:
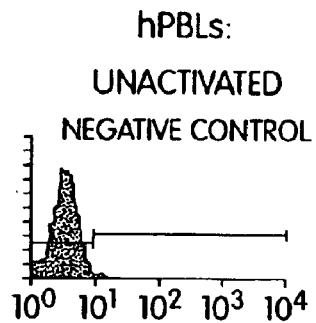
Figure 7D:
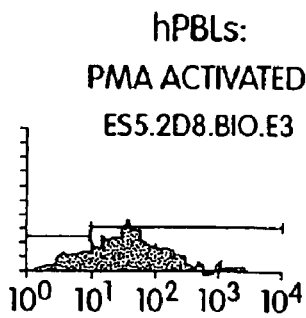

EXAMPLE 4
Immunophenotype of Cells Cultured with Anti-CD3 Stimulation and Addition of IL-2 or Anti-CD28 mAb To examine the subsets of T cells that are expanded, PBL were propagated for 16 days using either anti-CD3 and IL-2 or anti-CD3 and anti-CD28. FIG. 4 demonstrates the selective enrichment of CD4 cells from peripheral blood lymphocytes. Mononuclear cells were isolated from blood by ficoll hypaque density gradient centrifugation. The cells were stained with CD4 and CD8 monoclonal antibodies, and analyzed for the percent positive cells on day 0. The cells were then cultured on plastic immobilized anti-CD3 monoclonal antibody G19-4 plus IL-2 or plastic immobilized anti-CD3 monoclonal antibody G19-4 plus anti-CD28 monoclonal antibody 9.3 (0.5 µg/ml). The cells were isolated from culture on day 16, and repeat staining for CD4 and CD8 antigens was done by flow cytometry. Data was gated on the lymphocyte population by forward angle light scatter and side scatter. By this analysis, the % CD4 and CD8 cells were 8.0% and 84.5% in the cells grown in IL-2, and 44.6% and 52.5% in the cells grown in CD28. These results suggest that CD28 expansion favors the $CD4^+$ cell, in contrast to the well-established observation that $CD8^+$ cells predominate in cells grown in IL-2 (for example, see D. A. Cantrell and K. A. Smith, (1983), *J. Exp. Med.* 158:1895 and Gullberg, M. and K. A. Smith (1986) *J. Exp. Med.* 163, 270).

To further test this possibility, $CD4^+$ T cells were enriched to 98% purity using negative selection with monoclonal antibodies and magnetic immunobeads as described above. Fluorescent Activated Cell Sorter (FACS) Analysis was used to examine the phenotype of the T cells cultured with anti-CD3 and anti-CD28. Cells were pelleted by centrifugation and resuspended in PBS/1% BSA. The cells were then washed by repeating this procedure twice. The cells were pelleted and resuspended in 100 µl of primary antibody solution, vortexed, and kept on ice for one hour. After washing twice in PBS/1% BSA, the cells were resuspended in 100 µl of fluorescein-labeled goat-anti-mouse IgG and incubated for 30 minutes on ice. At the end of this incubation, the cells were washed twice in PBS and resuspended in 500 µl 1% paraformaldehyde in PBS. The labeled cells were analyzed on an Ortho Cytofluorograph. Cells were stained after isolation, or after 26 days in culture, with phycoerythrin conjugated anti-CD3 (Leu-4), CD4 (Leu-3A), CD8 (OKT8) or with IgG2a control monoclonal antibodies and fluorescence quantified with a flow cytometer. The cells were cultured for one month using anti-CD3 and either IL-2 or anti-CD28 to propagate the cells. There was equal expansion of the cells for the first 26 days of the culture (not shown), however, as can be seen in FIG. 5, the phenotype of the cells diverged progressively with increasing time in culture so that at day 26 of culture, the predominant cell in anti-CD28 culture was $CD4^+$ while the cells in the IL-2 culture were predominantly $CD8^+$. Thus, CD28 receptor stimulation, perhaps by crosslinking, is able to selectively expand T cells of the CD4 phenotype while the conventional method of in vitro T cell culture yields cells of the CD8 phenotype. Additional experiments have been conducted with similar results, indicating that CD28 stimulation of initially mixed populations of cells is able to yield cultures containing predominately or exclusively CD4 T cells, and thus one can expand and "rescue" the CD4 cells that were initially present in limiting amounts.

Figure 9:
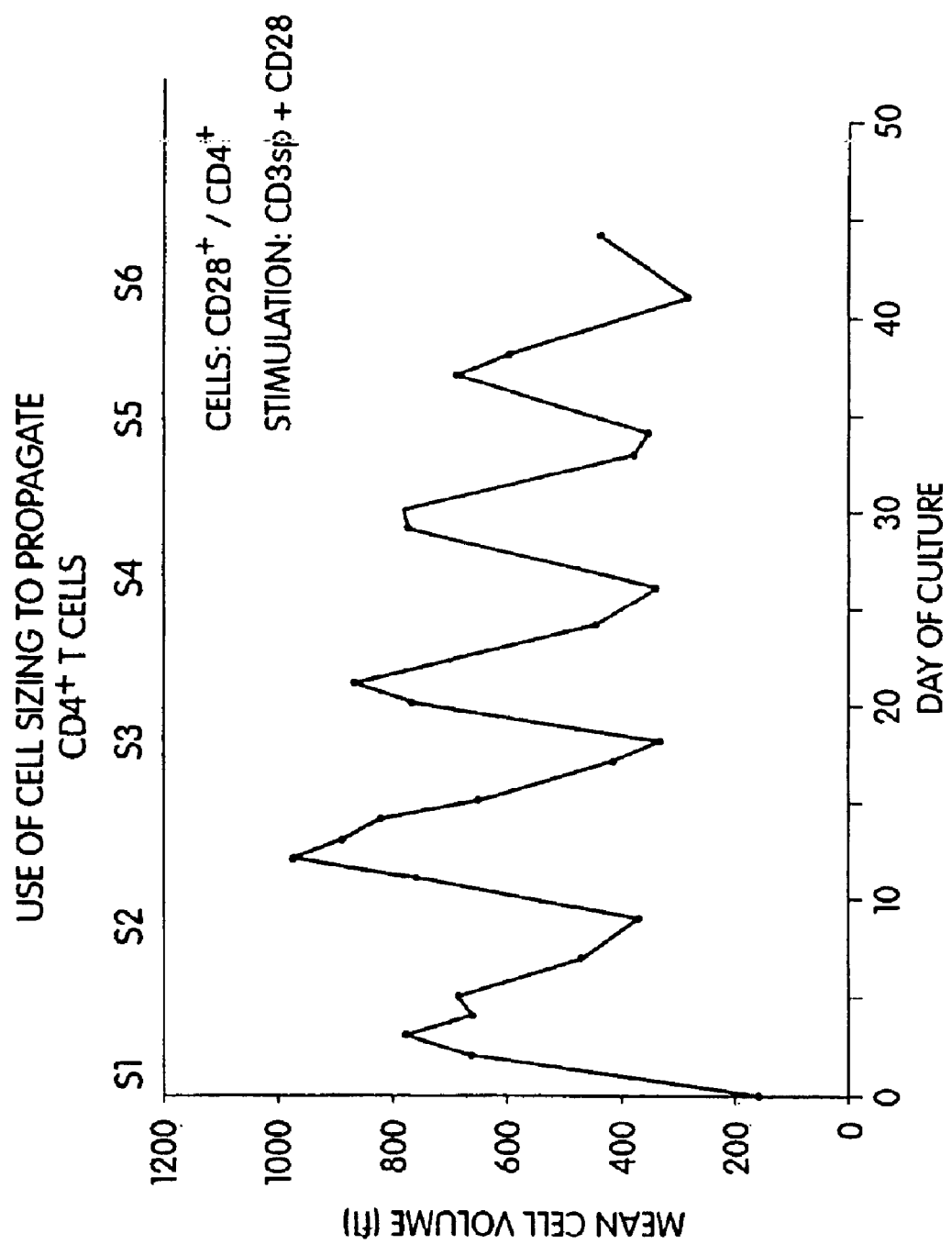
FIG. 9 depicts the increases in mean cell volume of $CD4^+$ T cells following stimulation (S1, S2, S3, S4, S5 and S6) with an anti-CD3 monoclonal antibody and an anti-CD28 monoclonal antibody over days in culture.

EXAMPLE 5
Use of Cell Sizing or Cyclic Expression of B7 on $CD4^+$ T Cells to Monitor T Cell Expansion To determine the time of T cell restimulation, changes in cell volume were monitored using a Coulter Counter ZM interfaced with a Coulter. $CD28^+$, $CD4^+$ T cells were isolated as described by magnetic immunoselection, and cultured in the presence of anti-CD28 mAb 9.3 (0.5 µg/ml) and restimulated with plastic immobilized anti-CD3 monoclonal antibody G19-4 as indicted. FIG. 9 demonstrates the cyclic changes in cell volume during six consecutive restimulations ("S1" to "S6") performed essentially as described in Example 1. Briefly, cells were expanded with anti-CD3 and anti-CD28 over three weeks in culture. Cells were changed to fresh medium at each restimulation with anti-CD3 antibody. Stimulations were spaced at ten day intervals. The cells were restimulated whenever cell volume decreased to <400 fl.

Figure 10:
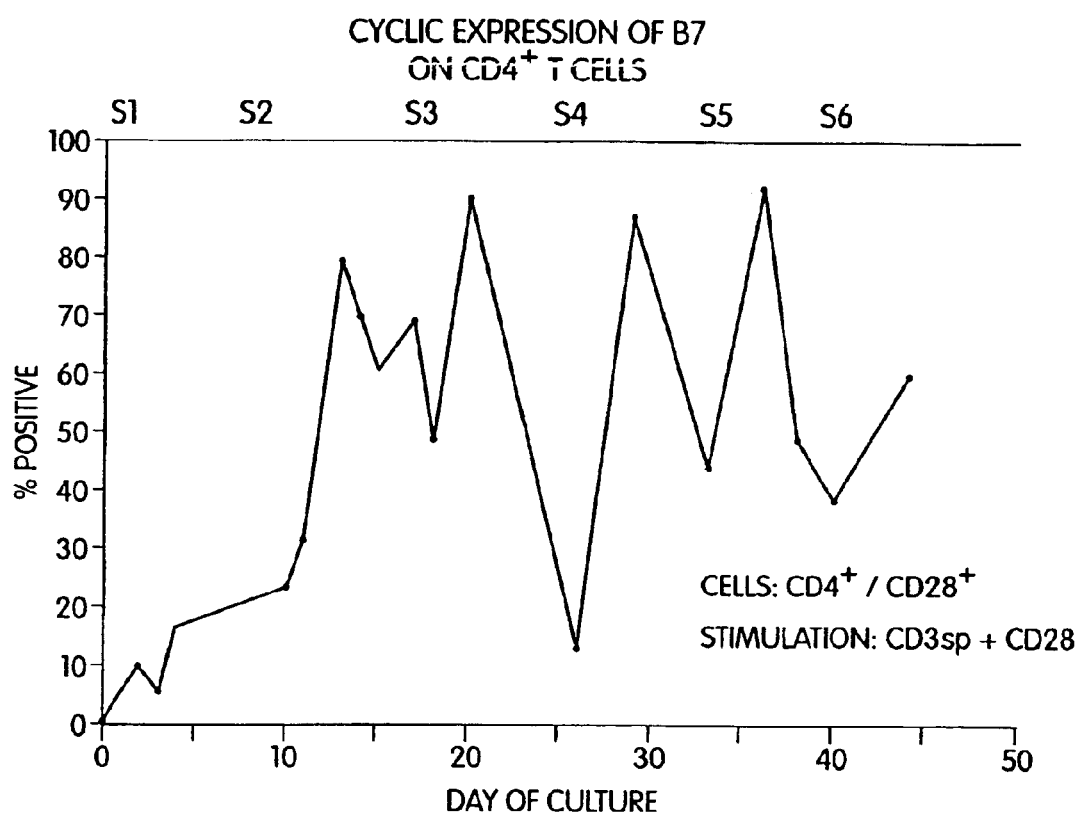
FIG. 10 depicts the cyclic expression of B7-1 on $CD4^+$ T cells following stimulation (S1, S2, S3, S4, S5 and S6) with an anti-CD3 monoclonal antibody and an anti-CD28 monoclonal antibody over days in culture.

In another experiment, cyclic expression of the B7-1 antigen was used to determine the time for T cell restimulation. The cells obtained from the experiment shown in FIG. 10 were stained with a CTLA-4Ig fusion protein (obtained from Repligen Corporation; see also Linsley P. S. et al. (1991) *J. Exp. Med.* 174, 561–569) and analyzed by flow cytometry to measure B7-1 receptor expression. It was determined that $CD4^+$ T cells do not initially express the B7-1 receptor, and that with culture, expression is induced. Further, the B7-1 expression was found to be transient, and to be re-induced with repeated anti-CD3 restimulation.

Figure 11:
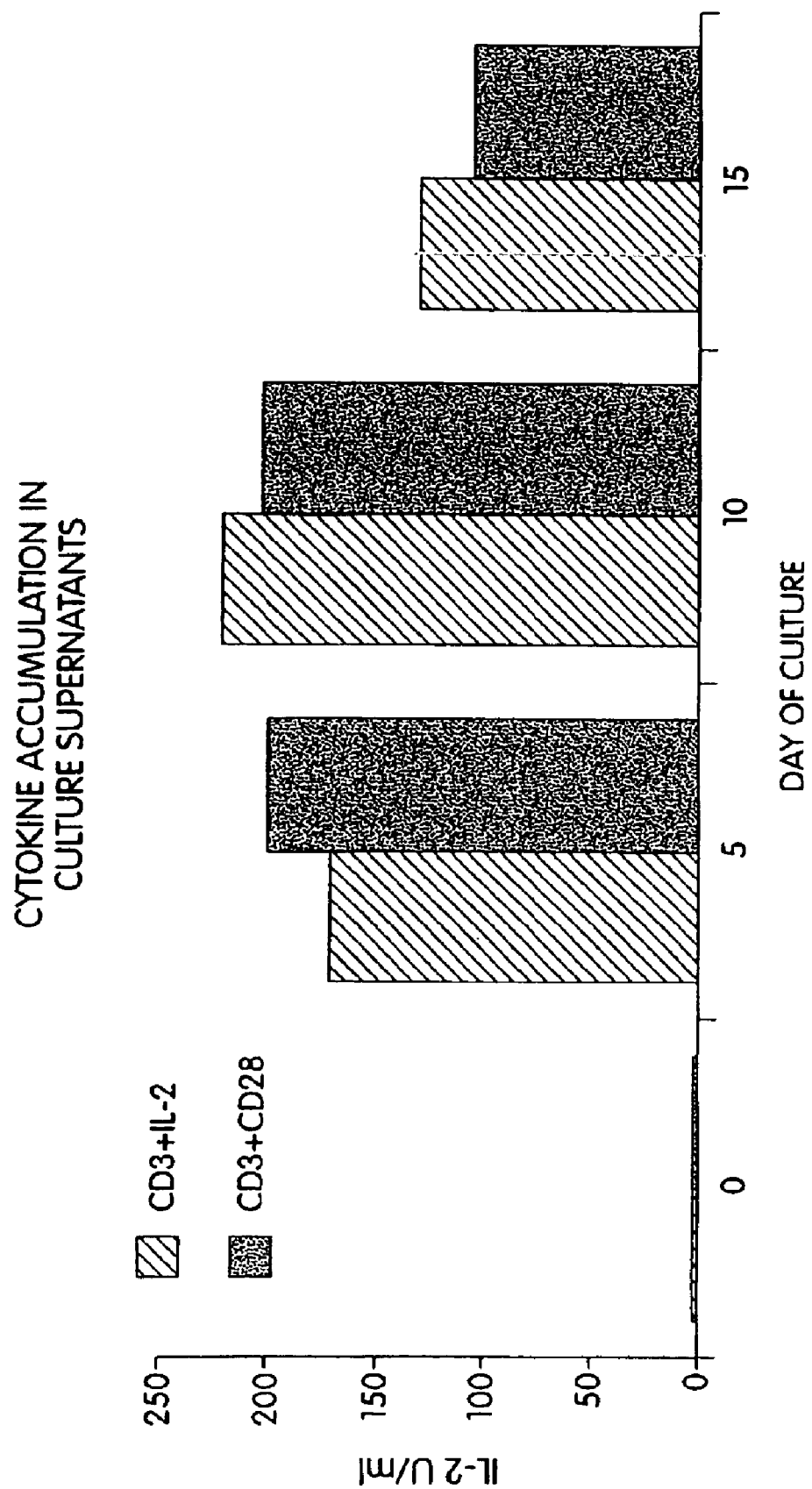
FIG. 11 is a bar graph depicting the amount of IL-2 produced by $CD4^+$ T cells following stimulation with an anti-CD3 monoclonal antibody and an anti-CD28 monoclonal antibody or IL-2 over days in culture.
Figure 12:
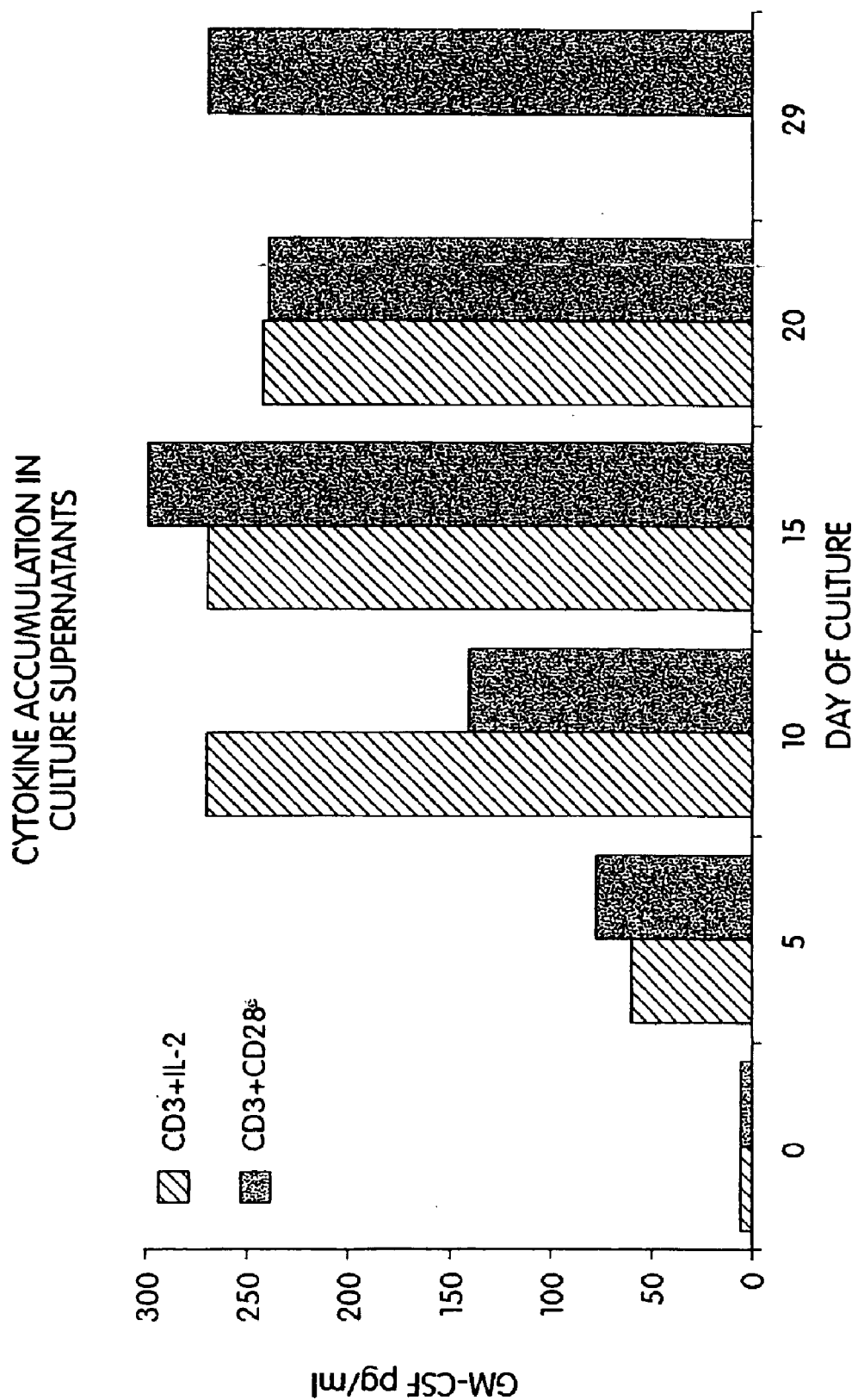
FIG. 12 is a bar graph depicting the amount of granulocyte-macrophage colony-stimulating factor (GM-CSF) produced by $CD4^+$ T cells following stimulation with an anti-CD3 monoclonal antibody and an anti-CD28 monoclonal antibody or IL-2 over days in culture.
Figure 13:
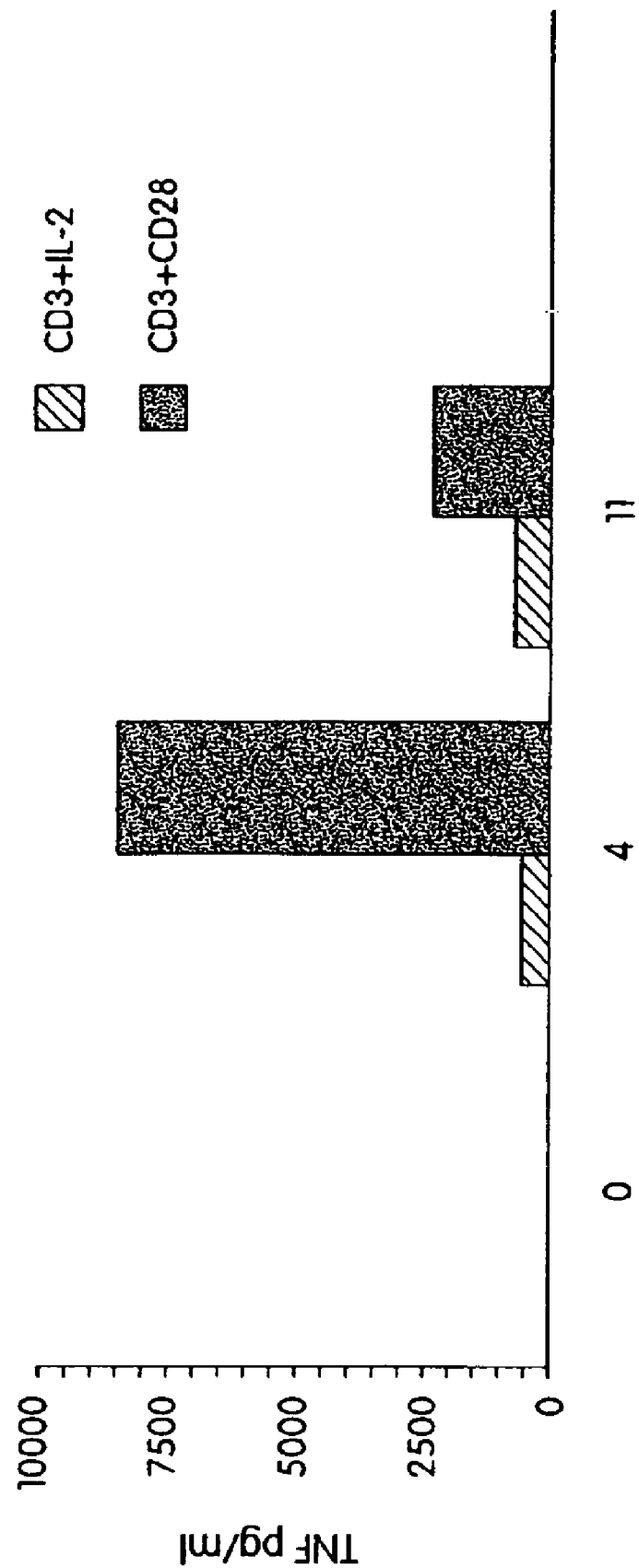
FIG. 13 is a bar graph depicting the amount of tumor necrosis factor (TNF) produced by $CD4^+$ T cells following stimulation with an anti-CD3 monoclonal antibody and an anti-CD28 monoclonal antibody or IL-2 over days in culture.

EXAMPLE 6
Production of Cytokines by T Cells Following Anti-CD28 Stimulation Experiments were conducted to analyze the cytokines produced by T cells following anti-CD28 stimulation. CD28$^+$/CD4$^+$ T cells were isolated as described in the previous examples. The cells were stimulated with plastic immobilized anti-CD3 mAb and IL-2 (200 U/ml), or anti-CD3 and anti-CD28 without added lymphokine. The cells were restimulated with anti-CD3 antibody as determined by changes in cell volume as described in Example 5. Cell culture supernatant was removed at the time points indicated and analyzed for IL-2 (FIG. 11), GM-CSF (FIG. 12), and TNF-α (FIG. 13). IL-2 was determined by bioassay on CTLL-2 cells while TNF-α and GM-CSF were measured by ELISA according to manufacturers instructions (TNFα, GMCSF:R&D Systems, Minneapolis, Minn.). The data shown for the various cytokines are from separate experiments. In other experiments (not shown) anti-CD3 plus anti-CD28 stimulation was shown to cause high levels of IL-4 and IL-5 in culture supernatants after approximately day 10 of culture, although only small amounts of these cytokines were present during the early period of culture.

The patterns of cytokine secretion with cells expanded by several restimulations according to the protocol described in the examples was compared to cells expanded with anti-CD3 plus IL-2 over three weeks in culture. Cells were changed to fresh medium at each restimulation with anti-CD3 antibody. Stimulations were spaced at ten day intervals. After 24 hours of further culture, an aliquot of cell culture supernatant was removed for assay. ELISA assays for individual cytokines were performed with kits from various suppliers (IL-2: T Cell Diagnostics, Cambridge, Mass.; IFN-γ Endogen, Inc., Boston, Mass.; IL-4, TNFα, GMCSF:R&D Systems, Minneapolis, Minn.) according to directions supplied with the kits. As can be seen from the results of a representative experiment shown in Table 2, the two protocols result in very similar levels of IL-2 and IL-4 secretion. The higher levels of GM-CSF and TNFα secretion with anti-CD3 and anti-CD28 costimulation suggests that the proliferative capacity of this combination of stimuli may be due in part to its ability to stimulate an autocrine loop.

TABLE 2

Comparison of cytokines secreted by T cells expanded with anti-CD3 and IL-2 versus T cells expanded with anti-CD3 and anti-CD28.

| Stimulation cycle | Costimulus | Concentration of lymphokine in pg/ml | | | | |
|---|---|---|---|---|---|---|
| | | IL-2 | IFN-γ | IL-4 | GM-CSF | TNFα |
| S1 | IL-2 | 20714 | 1458 | 16 | 2303 | 789 |
| | αCD28 | 13794 | 2211 | 14 | 3812 | 3387 |
| S2 | IL-2 | 20250 | 16600 | 964 | 51251 | 3221 |
| | αCD28 | 28411 | 56600 | 1030 | 138207 | 13448 |
| S3 | IL-2 | 21282 | 8617 | 1153 | 86418 | 2899 |
| | αCD28 | 14129 | 12583 | 1044 | 120418 | 5969 |

EXAMPLE 7
Polyclonality of T Cells Following Anti-CD28 Stimulation

Figure 14:
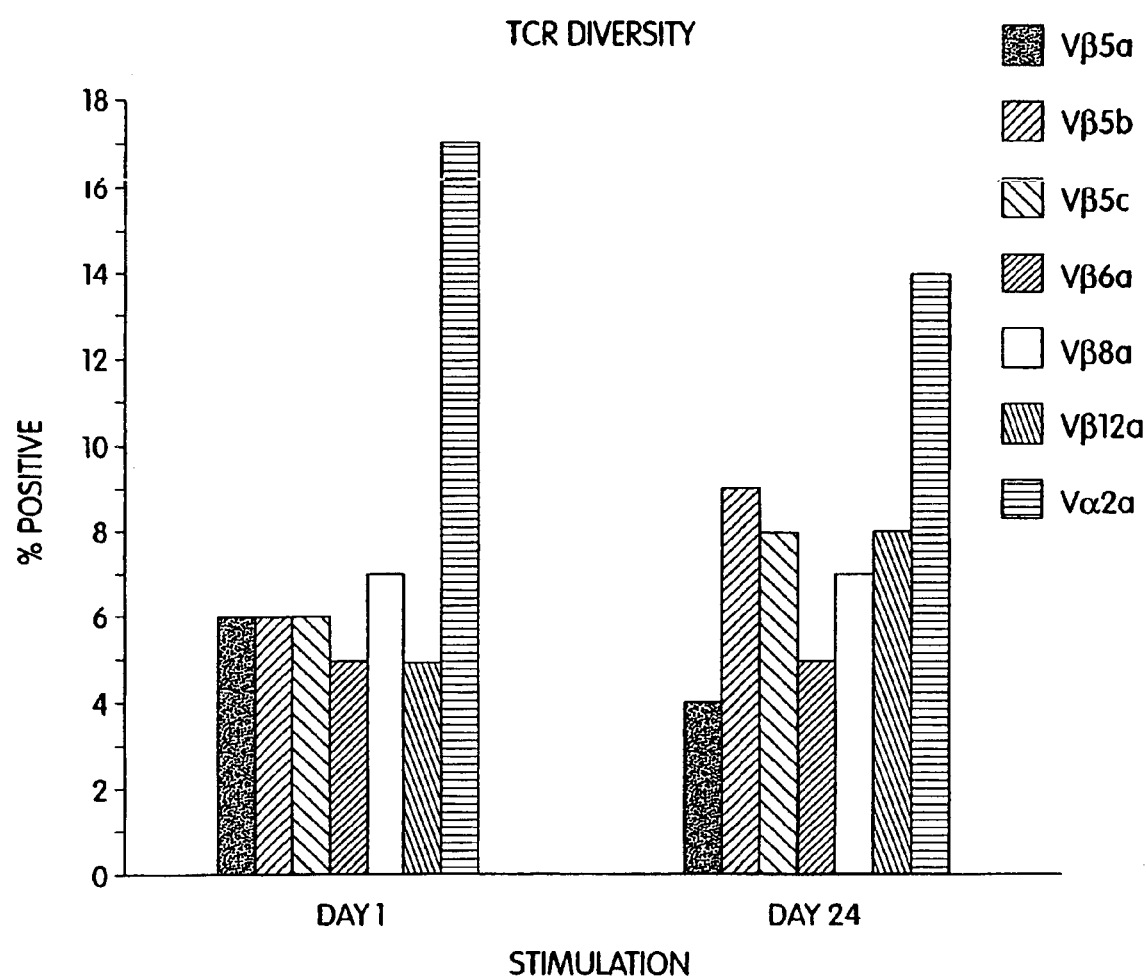
FIG. 14 is a bar graph depicting the T cell receptor (TCR) diversity in $CD4^+$ T cells following stimulation with an anti-CD3 monoclonal antibody and an anti-CD28 monoclonal antibody at day 1 and day 24 of culture.

The polyclonality of a population of T cells following stimulation with an anti-CD3 and an anti-CD28 antibody as described in the preceding examples was determined. CD28$^+$/CD4$^+$ T cells were isolated as described in the previous examples. The cells were stimulated with plastic immobilized anti-CD3 mAb and anti-CD28 mAb and FACS analysis conducted essentially as described in Example 4 using a panel of anti-TCR antibodies (Vβ5a, Vβ5b, Vβ5c, Vβ6a, Vβ8a, Vβ12a and Vα2a) obtained from Pharmingen. The polyclonality of the T cell population was determined before (Day 1) and after stimulation (Day 24). As shown in FIG. 14, the TCR diversity of a population of T cells stimulated through CD28 is maintained at day 24.

Figure 15:
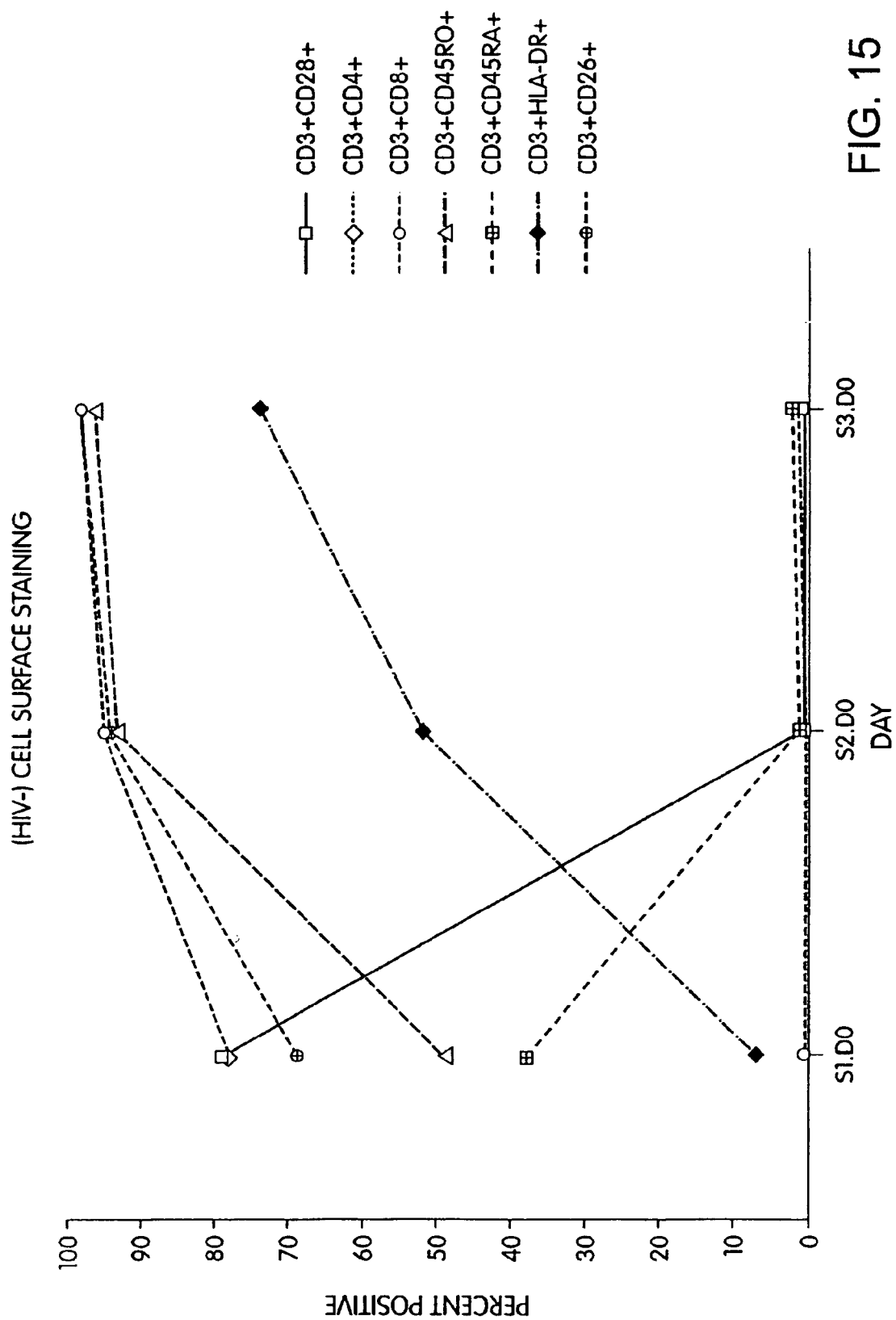
FIG. 15 depicts cell surface staining of $CD4^+$ T cells obtained from an HIV seronegative individual following stimulation (S1, S2 and S3) with an anti-CD3 monoclonal antibody and an anti-CD28 monoclonal antibody over days in culture.
Figure 16:
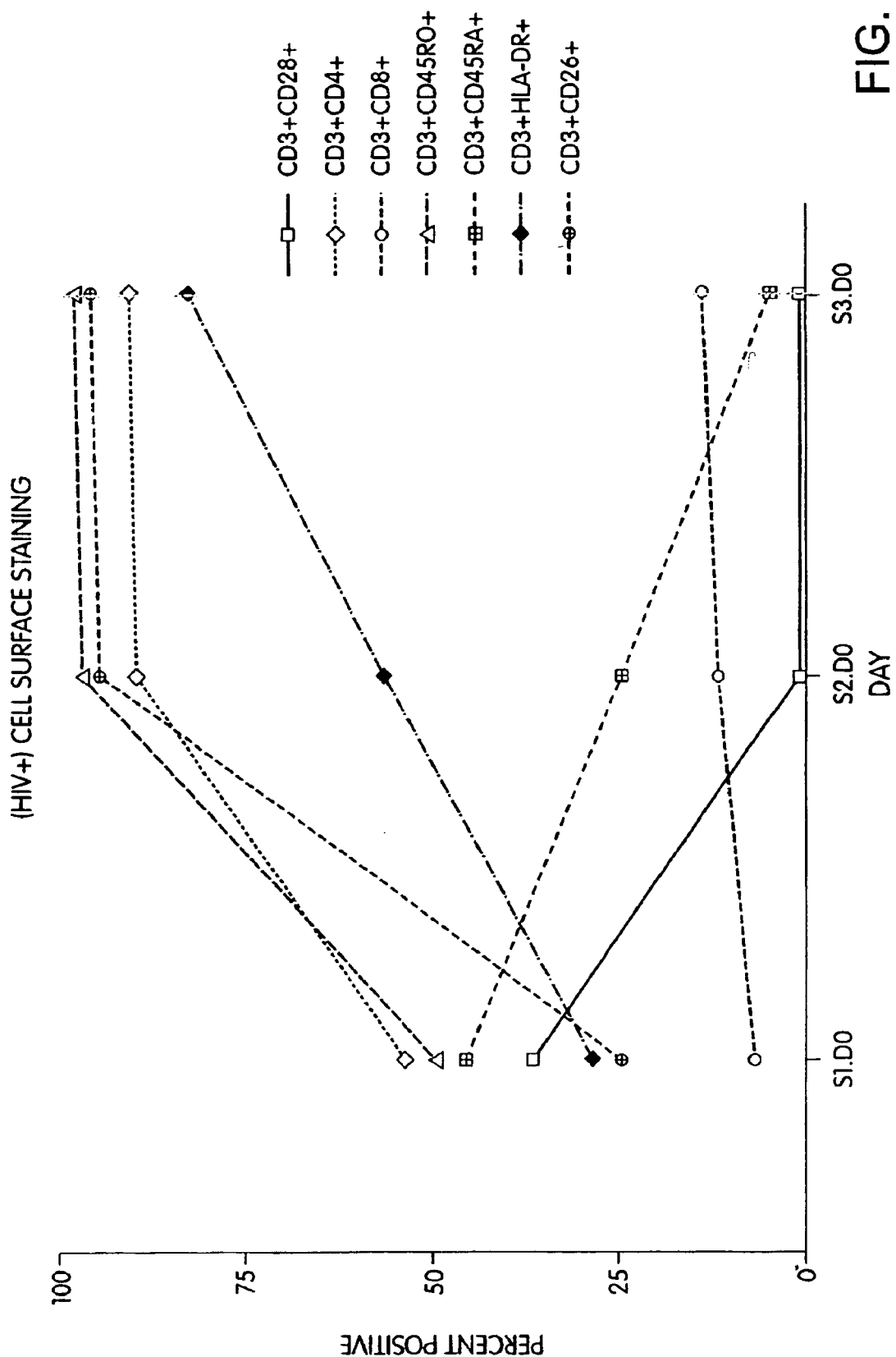
FIG. 16 depicts cell surface staining of $CD4^+$ T cells obtained from an HIV seropositive individual following stimulation (S1, S2 and S3) with an anti-CD3 monoclonal antibody and an anti-CD28 monoclonal antibody over days in culture.

EXAMPLE 8
Comparison of Cell Surface Staining of T Cells from HIV$^+$ and HIV-Individuals Following Anti-CD28 Stimulation Another series of experiments was conducted to determine the expression of various T cell surface markers on cells from HIV seropositive and seronegative individuals expanded according to the procedures described in the previous examples. CD28$^+$/CD4$^+$ T cells were obtained as described herein. In these experiments, the anti-CD3 mAb was labeled with a first label (e.g., rhodamine) and the appropriate second antibody (e.g., anti-CD28, anti-CD4, anti-CD8) was labeled with a second label (e.g., fluorescein). T cells were stimulated with plastic immobilized anti-CD3 mAb and anti-CD28 mAb as described herein and the percent of T cells expressing a variety of cell surface markers at different stimulations (i.e., S1, S2 and S3) determined by FACS analysis. As shown in FIGS. 15 and 16, the overall cell surface marker distribution on T cells obtained from HIV seropositive and seronegative individuals is approximately the same throughout the stimulation assay. It is noteworthy that the presence of one cell surface marker, CD45RA, which is a marker for naive T cells, declines over the course of CD28 stimulated T cell expansion. In contrast, the percent of T cells expressing the memory T cell surface marker, CD45RO, increases with CD28 stimulation. Thus, T cell expansion through CD28 stimulation preferentially expands memory T cells or converts naive T cells to memory T cells. It should be noted that the decline in the percent of T cells expressing CD28 is an artifact of the experiment due to the presence of anti-CD28 antibody in the T cell culture throughout the assay. The presence of anti-CD28 antibody prevents staining of the CD28 antigen.

EXAMPLE 9
Long Term Growth of CD8$^+$ T Cells with Anti-CD3 and Monoclonal Antibody ES5.2D8

Figure 17:
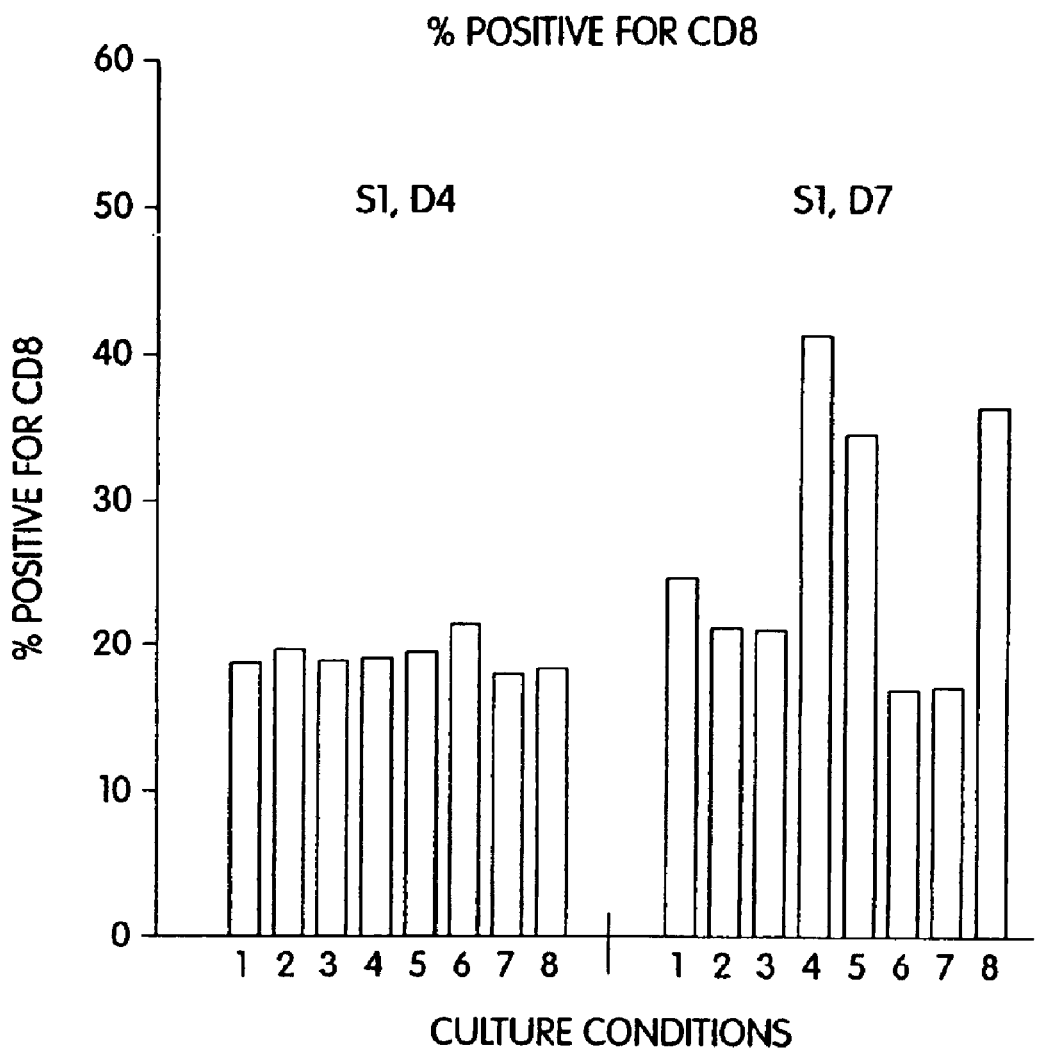
FIG. 17 depicts expansion of $CD8^+$ T cells following stimulation with an anti-CD3 monoclonal antibody and an monoclonal antibody ES5.2D8 at day 4 and day 7 of culture.
Figure 18A:
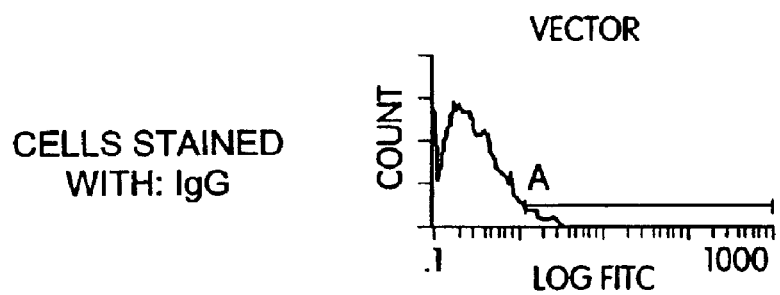
FIG. 18 depicts FACS analysis with the monoclonal antibody ES5.2D8 (panels C and D) or a control IgG (panels A and B) depicting the binding reactivity with MOP cells transfected with a plasmid encoding the CD9 antigen.
Figure 18B:
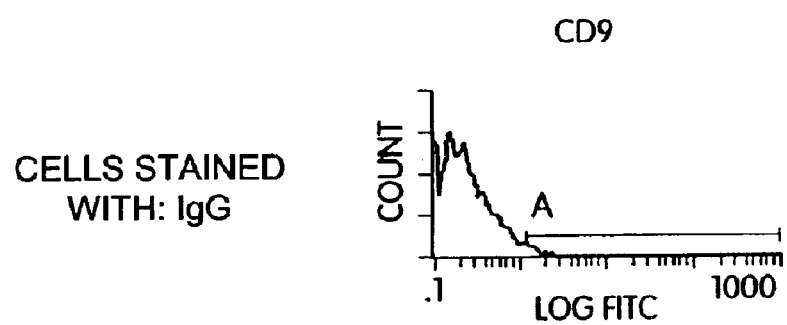
Figure 18C:
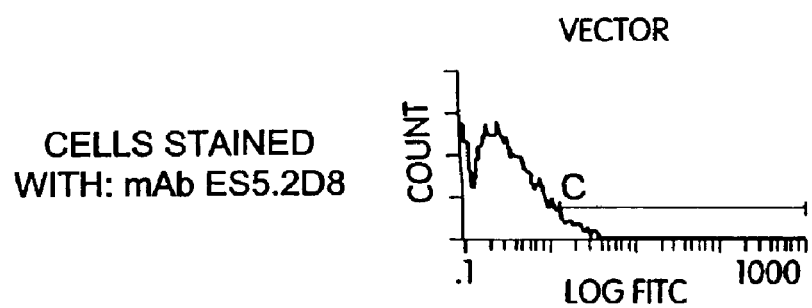
Figure 18D:
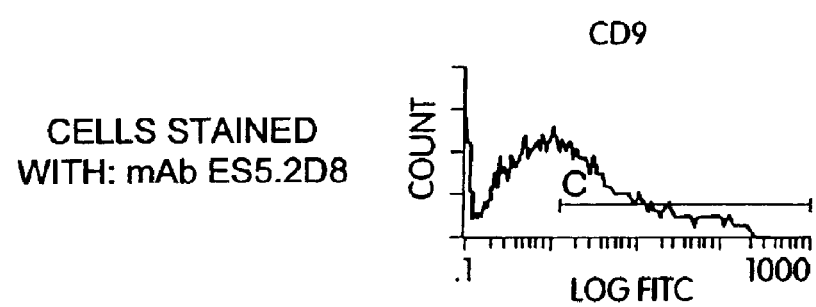

Experiments were conducted to determine whether a population of CD8$^+$ T cells could be preferentially expanded by stimulation with an anti-CD3 mAb and a monoclonal antibody ES5.2D8. CD28$^+$ T cells were obtained essentially as described in Example 1. To assay for CD8 expression, a primary anti-CD8 antibody and a labeled appropriate secondary antibody were used in FACS analysis to determine the percent positive cells. As shown in FIG. 17, at day 7 following stimulation of T cells with the anti-CD3 mAb G19-4sp and the mAb ES5.2D8 the CD8$^+$ fraction had increased from approximately 20% to over 40%. Another monoclonal antibody ER4.7G11 (referred to as 7G11) was also found to stimulate CD8$^+$ T cells. This antibody was raised against recombinant human CTLA4 and has been deposited with the ATCC on Jun. 3, 1994 at Accession No. HB 11642. This result indicates that binding of either a distinct region of CTLA4 or of a cross-reactive cell surface protein selectively activates CD8$^+$ T cells.

EXAMPLE 10
Defining the Epitope of the Monoclonal Antibody ES5.2D8 and Cloning the CD9 Antigen To determine the epitope of the monoclonal antibody ES5.2D8, epitope mapping was performed by phage display library (PDL) screening and was confirmed using synthetic peptides. A random 20 amino acid PDL was prepared by cloning a degenerate oligonucleotide into the fUSE5 vector (Scott, J. K. and Smith, G. P. (1990) Science 249:386–390) as described in Cwirla, S. E. et al. (1990) Proc. Natl. Acad. Sci. USA 87:6378–6382. The PDL was used to identify short peptides that specifically bound mAb ES5.2D8 by a micropanning technique described in Jellis, C. L. et al. (1993) Gene 137:63–68. Individual phage clones were purified from the library by virtue of their affinity for immobilized mAb and the random peptide was identified by DNA sequencing. Briefly, mAb ES5.2D8 was coated onto Nunc Maxisorp 96 well plates and incubated with 5×10$^{10}$ phage representing 8×10$^6$ different phage displaying random 20 amino acid peptides. Specifically bound phage were eluted, amplified, then incubated with the antibody a second time. After the third round, 7 phage were isolated, and DNA was prepared for sequencing.

Sequence analysis of these clones demonstrated that three of the seven sequences were identical and a fourth was similar:

```
                           2D8#2   (SEQ ID NO:5)
        H Q F C D H W G C W L L R E T H I F T P

2D8#4   (SEQ ID NO:6)
        H Q F C D H W G C W L L R E T H I F T P

2D8#10  (SEQ ID NO:7)
        H Q F C D H W G C W L L R E T H I F T P

2D8#6   (SEQ ID NO:8)
        L R L V L E D P G I W L R P D Y F F P A
```

Based on this data an epitope of G X W L X D/E (SEQ ID NO: 9) was proposed.

In addition to CTLA4, a second antigen for mAb ES5.2D8 was discovered using cDNA expression cloning.

A. Construction of a cDNA Expression Library

A cDNA library was constructed in the pCDM8 vector (Seed, (1987) Nature 329:840) using poly (A)$^+$ RNA isolated from activated T cells as described (Aruffo et al. (1987) Proc. Natl. Acad. Sci. USA 84:3365). To prepare total RNA, T cells were harvested from culture and the cell pellet homogenized in a solution of 4 M guanidine thiocyanate, 0.5% sarkosyl, 25 mM EDTA, pH 7.5, 0.13% Sigma antifoam A, and 0.7% mercaptoethanol. RNA was purified from the homogenate by centrifugation for 24 hour at 32,000 rpm through a solution of 5.7 M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 μg of poly(A)$^+$ RNA in a reaction containing 50 mM Tris, pH 8.3, 75 mM KCl, 3 mM MgCl$_2$, 10 mM dithiothreitol, 500 μM dATP, dCTP, dGTP, dTTP, 50 μg/ml oligo(dT)$_{12-18}$, 180 units/ml RNasin, and 10,000 units/ml Moloney-MLV reverse transcriptase in a total volume of 55 μl at 37° C. for 1 hr. Following reverse transcription, the cDNA was converted to double-stranded DNA by adjusting the solution to 25 mM Tris, pH 8.3, 100 mM KCl, 5 mM MgCl$_2$, 250 μM each dATP, dCTP, dGTP, dTTP, 5 mM dithiothreitol, 250 units/ml DNA polymerase I, 8.5 units/ml ribonuclease H and incubating at 16° C. for 2 hr. EDTA was added to 18 mM and the solution was extracted with an equal volume of 50% phenol, 49% chloroform, 1% isoamyl alcohol. DNA was precipitated with two volumes of ethanol in the presence of 2.5 M ammonium acetate and with 4 micrograms of linear polyacrylamide as carrier. In addition, cDNA was synthesized from 4μg of poly(A)$^+$ RNA in a reaction containing 50 mM Tris, pH 8.8, 50 μg/ml oligo(dT)$_{12-18}$, 327 units/ml RNasin, and 952 units/ml AMV reverse transcriptase in a total volume of 100 μl at 42° C. for 0.67 hr. Following reverse transcription, the reverse transcriptase was inactivated by heating at 70° C. for 10 min. The cDNA was converted to double-stranded DNA by adding 320 μl H$_2$O and 80 μl of a solution of 0.1 M Tris, pH 7.5, 25 mM MgCl$_2$, 0.5 M KCl, 250 μg/ml bovine serum albumin, and 50 mM dithiothreitol, and adjusting the solution to 200 μM each dATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5 M ammonium acetate and with 4 micrograms of linear polyacrylamide as carrier.

The DNA from 4 μg of AMV reverse transcription and 2.0 μg of Moloney MLV reverse transcription were combined. Non-self complementary BstXI adaptors were added to the DNA as follows: The double-stranded cDNA from 6μg of poly(A)$^+$ RNA was incubated with 3.6 μg of a kinased oligonucleotide of the sequence CTTTAGAGCACA (SEQ ID NO: 9) and 2.4 μg of a kinased oligonucleotide of the sequence CTCTAAAG in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 15° C. for 16 hours. EDTA was added to 34 mM and the solution was extracted with an equal volume of 50% phenol, 49% chloroform, 1% isoamyl alcohol. DNA was precipitated with two volumes of ethanol in the presence of 2.5 M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored cDNA from 6 μg of poly(A)$^+$RNA was ligated to 2.25 μg of BstXI cut pCDM8 in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° C. for 24 hr. The ligation reaction mixture was then transformed into competent E.coli DH10B/P3 by standard techniques.

Plasmid DNA was prepared from a 500 ml culture of the original transformation of the cDNA library. Plasmid DNA was purified by the alkaline lysis procedure followed by twice banding in CsCl equilibrium gradients (Maniatis et al, Molecular Cloning: A Laboratory Manual, Cold Spring Harbor, N.Y. (1987)).

B. Cloning Procedure

In the cloning procedure, the cDNA expression library was introduced into MOP8 cells (ATCC No. CRL1709) using lipofectamine and the cells screened with mAb ES5.2D8 to identify transfectants expressing a ES5.2D8 ligand on their surface. In the first round of screening, thirty 100 mm dishes of 50% confluent COS cells were transfected with 0.05 μg/ml activated T cell library DNA using the DEAE-Dextran method (Seed, B. et al. (1987) *Proc. Natl. Sci. USA* 84:3365). The cells were trypsinized and re-plated after 24 hours. After 47 hours, the cells were detached by incubation in PBS/0.5 mM EDTA, pH 7.4/0.02% Na azide at 37° C. for 30 mm.

Detached cells were treated with 10 μg/ml mAb ES5.2D8. Cells were incubated with the monoclonal antibody for 45 minutes at 4° C. Cells were washed and distributed into panning dishes coated with affinity-purified goat anti-mouse IgG antibody and allowed to attach at room temperature. After 3 hours, the plates were gently washed twice with PBS/0.5 mM EDTA, pH 7.4/0.02% Na azide, 5% FCS and once with 0.15M NaCl, 0.01M Hepes, pH 7.4,5% FCS. Unbound cells were thus removed and episomal DNA was recovered from the adherent panned cells by conventional techniques.

Episomal DNA was transformed into *E. coli* DH10B/P3. The plasmid DNA was re-introduced into MOP8 cells using lipofectamine and the cycle of expression and panning was repeated twice. Cells expressing a ES5.2D8 ligand were selected by panning on dishes coated with goat anti-mouse IgG antibody. After the third round of screening, plasmid DNA was prepared from individual colonies and transfected into MOP8 cells by the DEAE-Dextran method. Expression of a ES5.2D8 ligand on transfected MOP8 cells was analyzed by indirect immunofluorescence with mAb ES5.2D8 (See FIG. 18).

DNA from one clone (mp5) identified as positive by FACS analysis was sequenced using standard techniques. FASTA analysis of the amino acid sequence of mp5 identified a matching protein, CD9, in the GCG data banks. The full amino acid sequence of CD9 is shown below (SEQ ID NO: 6).

BESTFIT analysis of the phage epitopes of mAb ES5.2D8 to the amino acid sequence of CD9 revealed a close match:

G C W L L R E    (phage 2D8#2, 4, 10; SEQ ID NO:11)

G I W L R P D    (phage 2D8#6; SEQ ID NO:12)

G L W L R F D    (CD9 sequence; SEQ ID NO:13)

| FT | DOMAIN | 111 | 194 | EXTRACELLULAR (PROBABLE) |
|---|---|---|---|---|
| FT | TRANSMEM | 195 | 220 | POTENTIAL |
| FT | DOMAIN | 221 | 227 | CYTOPLASMIC (PROBABLE) |
| FT | CARBOHYD | 51 | 51 | POTENTIAL |
| FT | CARBOHYD | 52 | 52 | POTENTIAL |
| FT | CONFLICT | 8 | 8 | C→S (IN REF. 1) |
| FT | CONFLICT | 66 | 66 | G→A (IN REF. 1) |
| FT | CONFLICT | 193 | 193 | MISSING (IN REF. 1) |
| SQ | SEQUENCE | 227 AA; | 25285 MW; | 261251 CN; |

Cd9_Human Length: 227 May 25, 1994 14:10 Type: P Check: 1577

```
                                              (SEQ ID NO:10)
  1  PVKGGTKCIK YLLFGFNFIE WLAGIAVLAI GLWLRFDSQT
                                              KSIFEQETNN

51  NNSSFYTGVY ILIGAGALMM LVGFLGCCGA VQESQCMLGL
                                              FFGFLLVIFA

101  IEIAAAIWGY SHKDEVIKEV QEFYKDTYNK LKTKDEPQRE
                                              TLKAIHYALN
```

-continued

```
151  CCGLAGGVEQ FISDICPKKD VLETFTVKSC PDAIKEVFDN
                                              KFHIIGAVGI

201  GIAVVMIFGM IFSMILCCAI RRNREMV
```

EXAMPLE 11

Induction of T Cell Expansion by Costimulation with B7-1 or B7-2

In order to determine whether costimulation through CD28 can be provided by B7-1 and B7-2 molecules expressed on cells transfected with a nucleic acid encoding either of these molecules, Chinese Hamster Ovary (CHO) cells were transfected with human B7-1 (CD80) or B7-2 (CD 86) (Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 262:909–911; Azuma, M. et al. (1993) *Nature* 366:76–79; Freeman, G. J. et al. (1993) *J. Exp. Med.* 178:2185–2192). The cells were maintained in G418 as described in Gimmi et al.(1991) *PNAS* 88:6575 and Engel et al. (1994) *Blood* 84:1402. Briefly, a cDNA fragment of B7-1 containing nucleotides 86–1213 (comprising the coding region) was inserted into the eukaryotic expresssion vector pLEN (Metabolic Biosystem, Mountain View, Calif.) containing the human metallothionein IIA promoter, the simian virus 40 enhancer, and the human growth hormone 3' untranslanted region and polyadenylation site. A cDNA fragment of B7-2 containing the coding region was inserted into pLEN. Fifty micrograms of Pvu I linearized B7-pLEN construct was cotransfected with 5 micrograms of linearized SV2-Neo-SP65 into CHO cells by electroporation using the BRL electroporator at settings of 250 V and 1600 μF. Transfectants were selected by growth in medium containing the neomycin analogue G418 sulfate (400 μg/ml) and were cloned. Mock transfected CHO cells were made by transfection of linearized SV2-Neo-Sp65 alone.

To determine the relative expression of human B7-1 and B7-2 on the stably transfected CHO cells, the cells were stained with CTLA4Ig (obtained from Repligen Corporation) and FITC conjugated goat anti-human IgG Fc, or with anti-B7-1 monoclonal antibody 133 (Freeman et al. *J. Immunol.* 137:3260 (1987)) and FITC goat anti-mouse IgM, or with anti-B70 (B7-2) monoclonal antibody IT2 (obtained from Pharmingen Corporation) and FITC goat anti-mouse IgG, fixed in paraformaldehyde and fluorescence analyzed by flow cytometry. The B7-1-CHO cells expressed about twice as many binding sites than the B7-2-CHO cells for CTLA4Ig. Control CHO cells (CHO-neo) consisted of CHO cells transfected with the neomycin resistance vector, and did not stain specifically for CTLA4Ig. Specificity of ligand expression was confirmed by measurement with anti-CD80 mAb BBI (Yokochi, T. et al. (1982) *J. Immunol.* 128:823–827) and anti-CD86 mAb IT2. Mitomycin C treatment did not affect B7 expression.

Figure 19:
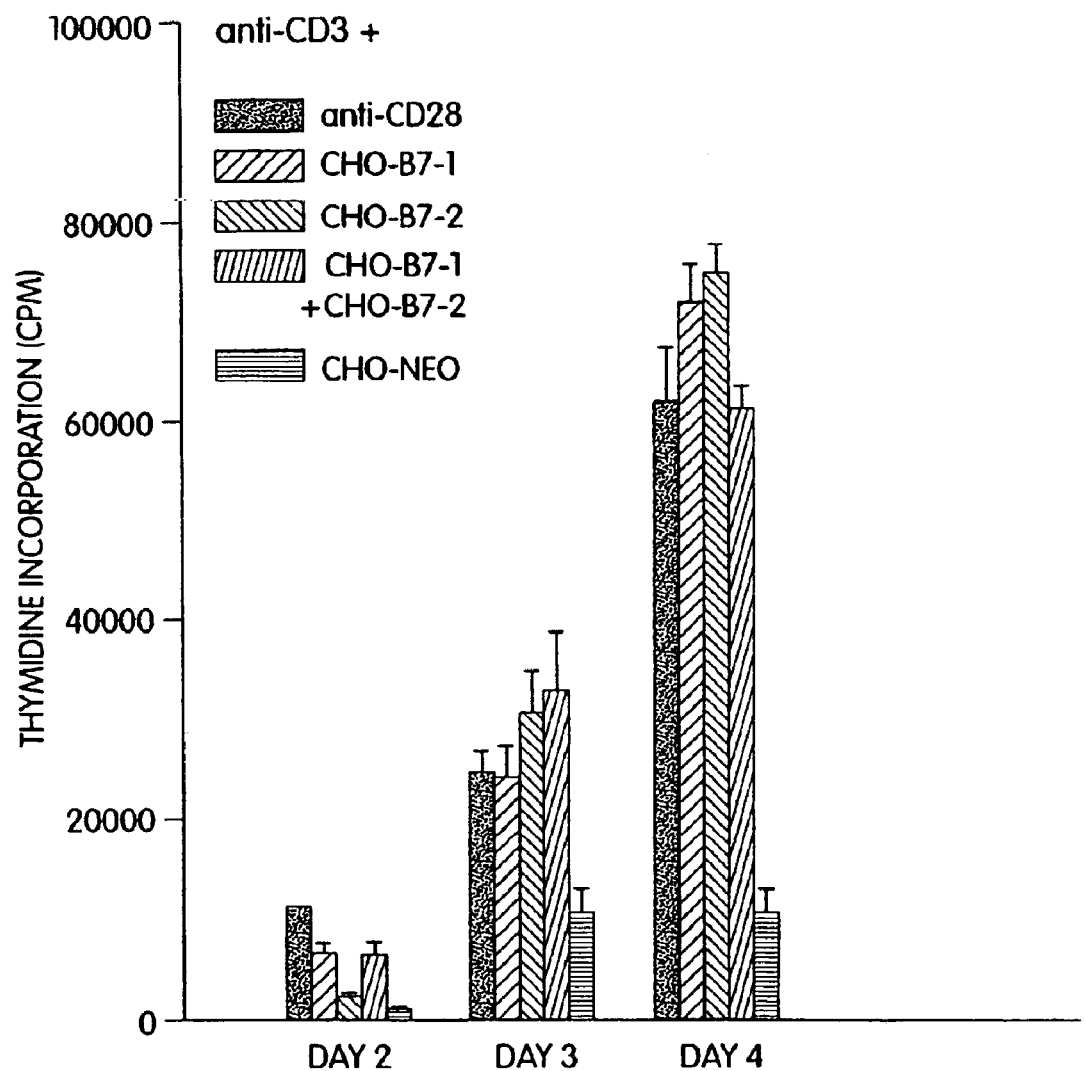
FIG. 19 depicts $CD28^+$ T cell expansion following stimulation with anti-CD3 monoclonal antibody coated beads and anti-CD28 antibody, B7-1, B7-2, B7-1 and B7-2, or control CHO-neo cells at different time points after stimulation.

In order to explore whether costimulation by the CD28 and CTLA4 ligands B7-1 and B7-2 is similar, CD28+ T cells were cultured with anti-CD3 in the presence of B7-1 or B7-2-transfected CHO cells, or control CHO-neo cells (FIG. 19). For this experiment, CD28+ T were isolated from peripheral blood lymphocytes by Percoll gradient centrifugation from leukopacks obtained by apheresis of healthy donors and purified by negative selection according to June et al. (1987) *Mol. Cell Biol.* 7:4472. Purified T cells were cultured in RPMI 1640 containing 10% heat-inactivated fetal calf serum (Hyclone, Logan Utah), 2 mM L-glutamine, and 20 mM Hepes in 96 well flat bottom microtiter plates at 37° C. in 5% $CO_2$. The $CD28^+$ T cells ($5 \times 10^4$ cells/well) were stimulated with anti-CD3 monoclonal antibody coated beads (3 beads per T cell) in the presence of mitomycin C-inactivated CHO cells expressing B7-1, B7-2, or neomycine resistance gene only ($2 \times 10^4$ cells/well). Cells were also stimulated with anti-CD3 monoclonal antibody OKT3 coated beads in the presence of anti-CD28 mAb 9.3 at 1 µg/ml. In preliminary experiments, the anti-CD28 mAb was titered to determine the optimal amounts for induction of IL-2 secretion. The anti-CD3 monoclonal antibody OKT3 (IgG2a), obtained from the ATCC, was bound to magnetic beads (M-450, Dynal Corp.) that were coated with goat anti-mouse IgG by adding 150 femtograms of antibody per bead, and the beads washed extensively. In all experiments, antigen presenting cells were first removed from the $CD28^+$ T cells by immunomagnetic bead depletion. CHO cells were inactivated by pretreatment with mitomycin C at 25 µg/ml for one hour. On days 2 to 4 of culture, thymidine incorporation experiments were performed by pulsing the cultures overnight with methyl-$^3$H-thymidine (New England Neclear) with 37 kBq/well and incorporation determined by liquid scintillation spectroscopy. Results were expressed as the mean±SEM cpm of triplicate determinations.

The results of the experiment are shown graphically in FIG. 19. On day 3 of culture, low level proliferation was observed in cells stimulated with anti-CD3 in the presence of control CHO cells, and levels of thymidine incorporation did not increase with further culture. In contrast, there was increasing thymidine incorporation in T cells that were co-cultured with CHO cells that express B7-1 or B7-2 that was detected after 2 to 4 days of culture, and this cellular proliferation continued until exhaustion of culture medium. Levels of thymidine incorporation in B7-1 and B7-2 stimulated cultures was similar to cultures stimulated with anti-CD3 plus anti-CD28 monoclonal antibody. Thus, B7-1 and B7-2 molecules expressed on CHO cells can costimulate T cells as efficiently as anti-CD28 monoclonal antibody.

Figure 20:
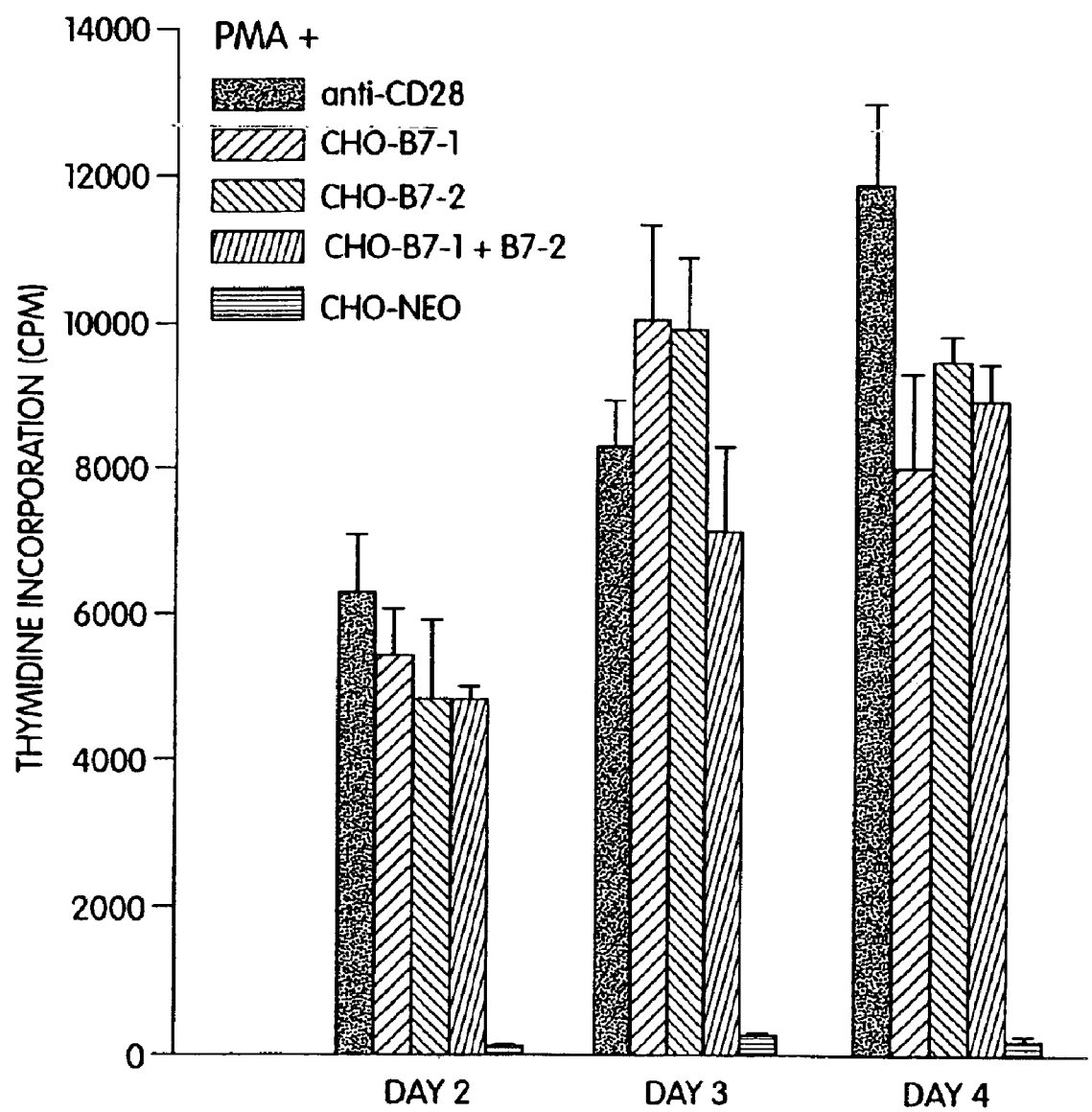
FIG. 20 depicts $CD28^+$ T cell expansion following stimulation with PMA and anti-CD28 antibody, B7-1, B7-2, B7-1 and B7-2, or control CHO-neo cells at different time points after stimulation.

In preliminary experiments, culture of T cells with B7-1 or B7-2 expressing CHO cells alone or in combination did not result in T cell proliferation, consistent with previous reports that B7-1 alone is not mitogenic (Liu et al. (1992) Eur. J. Immunol. 22:2855). Anti-CD28 stimulation in combination with PMA has previously been shown to be comitogenic. To determine whether B7-1 or B7-2 were comitogenic with PMA, purified $CD28^+$ T cells were cultured in PMA (10 nM) with mitomycin C-inactivated CHO cells expressing B7-1, B7-2, a 1:1 mixture of B7-1 plus B7-2 expressing CHO cells, or control CHO-neo cells only, or with anti-CD28 monoclonal antibody (1 µg/ml), and the time course of cellular proliferation determined. The results are shown graphically in FIG. 20. Proliferation was less vigorous in the presence of 10 nM PMA than when cells were cultured with anti-CD3 mAb (FIG. 20). The time course of proliferation was similar in cultures that contained B7-1, B7-2 or a mixture of cells expressing B7-1 plus B7-2. In contrast, cells cultured in PMA only or PMA plus CHO-neo cells incorporated low amounts of thymidine, consistent with the rigorous removal of antigen presenting cells. Thus, B7-1 or B7-2 molecules expressed on CHO cells can provide a costimulatory signal to T cells activated either by anti-CD3 mAb or PMA, but proliferation is stronger with anti-CD3 mAb.

Resting T cells do not express detectable amounts of CTLA-4, however activated T cells express both CD28 and CTLA-4 by day 2 of culture (Linsey et al.(1992) J. Exp. Med. 176:1595). Given that both B7-1 and B7-2 bind to CD28 and CTLA-4, it was possible that some component of cellular activation could be attributed to CTLA-4, compatible with previous studies indicating that CTLA-4 ligation can enhance comitogenic effects of suboptimal CD28 ligation (Damle et al. (1994) J. Immunol. 152:2686). For this experiment, anti-CD28 Fab fragments were produced by papain digestion of 9.3 mAb and two cycles of purification on a protein A column (Pierce, Rockford, Ill.). $CD28^+$ T cells were cultured in the presence of anti-CD3 coated beads and CHO (as described above) cells for three days in the presence of increasing amounts of CD28 Fab fragments. Cells were pulsed with tritiated thymidine and scintillation counting performed on the indicated day of culture. IL-2 concentration in culture supernatants was determined by ELISA using a commercially available kit from T Cell Diagnostics (Cambridge, Mass.) after 24 hours of culture. The values reported were assessed by using dilutions of culture supernatant that yielded read-outs within the linear portion of the standard curve.

Figure 21:
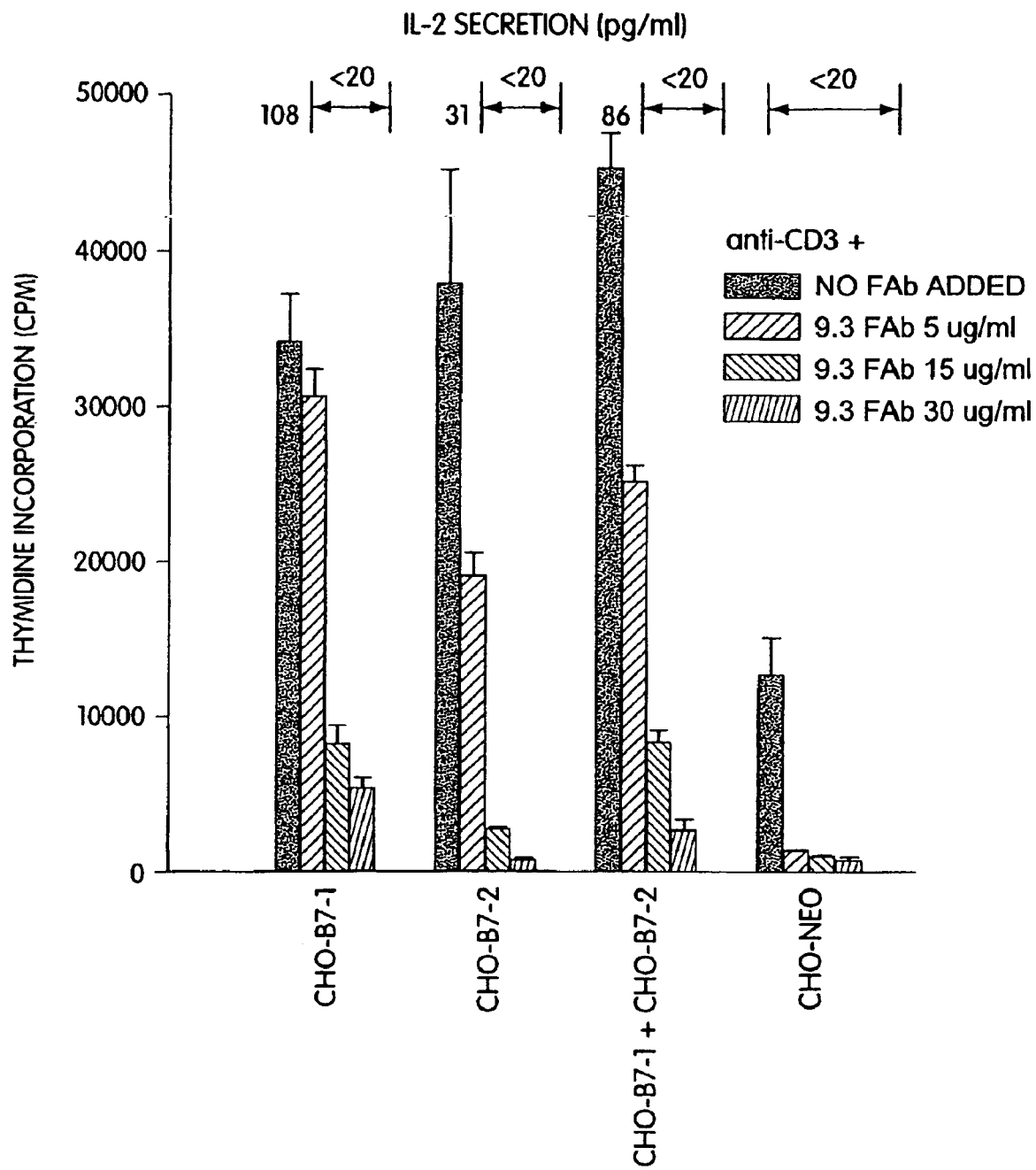
FIG. 21 depicts $CD28^+$ T cell expansion following stimulation with anti-CD3 monoclonal antibody coated beads, B7-1, B7-2, B7-1 and B7-2, or control CHO-neo cells in the presence of various amounts of antiCD28 Fab fragments and the amount of IL-2 secreted in the medium.

The results are shown graphically in FIG. 21. Proliferation induced by both B7-1 and B7-2 was inhibited >95% in a dose-dependent manner by CD28 Fab fragments, indicating that both forms of B7 costimulation are critically dependent on interaction with CD28. IL-2 accumulation in culture supernatants was also efficiently blocked by the Fab fragments. Together these results demonstrate that both B7-1 and B7-2 molecules expressed on CHO cells are capable of costimulating T cell proliferation similarly to costimulating T cell proliferation with CD28 mAbs.

EXAMPLE 12

Costimulation with B7-1 and B7-2 Induce Long Term Proliferation of $CD4^+$ T Cells The ability of the B7 ligands to sustain T cell proliferation in long term cultures was investigated. For these experiments, $CD4^+$ T cells were obtained from $CD28^+$ T cells by negative selection using magnetic beads (Dynal) coated with CD8 monoclonal antibodies as described in June et al. (1989) J. Immunol. 143:153. The phenotype of the cells was 99% $CD2^+$, 98% $CD28^+$, and 96% $CD4^+$. $5 \times 10^6$ purified $CD4^+$ T cells were stimulated with anti-CD3 monoclonal antibody coated beads ($1.5\ 10^7$ beads) and mitomycin C-inactivated CHO cells ($2.10^6$ cells) expressing B7-1, B7–2, or neomycin resistance only, or with anti-CD3 plus anti-CD28 coated "cis" beads, i.e. with both antibodies on the same bead. Beads were coated with anti-CD3 (OKT3) and anti-CD28 9.3 monoclonal antibody with each antibody added at 150 femtograms per bead. It is important to note that no cytokines were added to the culture medium so that cell growth was dependent on secretion of cytokines and lymphokines. Fresh medium was added at two to three days intervals with fresh medium to maintain cell concentrations between $0.5–1.5 \times 10^6$ T cells/ml; antibody-coated beads and CHO cells were not cleared from culture, but were diluted progressively until restimulation. The cell cultures were monitored by electronic cell sizing using a Coulter Counter model ZM and Channelyzer model 256 (Coulter, Hialeah, Fla.), and restimulated at approximately 7 to 10 day intervals (i.e. when the volume of the T cell blasts decreased to <400 fl) with additional beads and mitomycin C-treated CHO cells. Viable T cells were counted and the total number of cells that would be expected to accumulate displayed, taking into account discarded cells.

Figure 22:
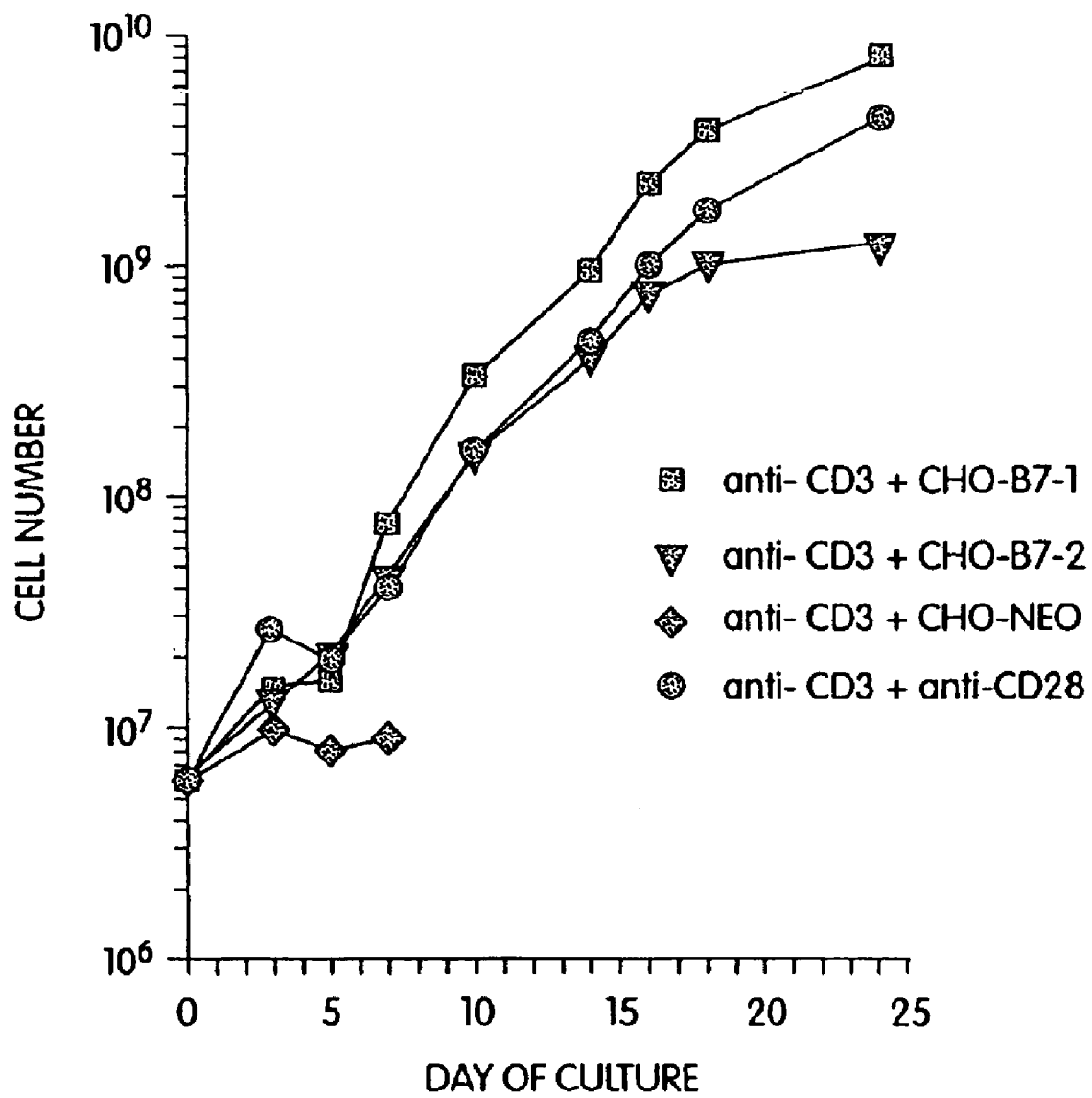
FIG. 22 depicts growth curves of $CD4^+$ peripheral blood T cells in long term cultures with either anti-CD3 monoclonal antibody, anti-CD28 antibody, B7-1, B7-2, or control CHO-neo cells.

The results are shown graphically in FIG. 22. Both B7-1 and B7-2 resulted in exponential T cell expansion, and during the first three weeks of culture both B7 receptors could consistently induce a $\geq 3\ \log_{10}$ of expansion that was polyclonal. Together, the above results indicate that either B7-1 or B7-2 can costimulate long-term proliferation in a CD28-dependent manner, independent of a requirement for simultaneous B7-1 plus B7-2 receptor coexpression. To date, no phenotypic differences have been detected in the cells that arise from B7-1 or B7-2 stimulated CD4+ T cell expansion. T cells cultured with anti-CD3 and control CHO cells did not undergo sustained proliferation, and the culture was terminated due to poor viability. Thus, B7-1 and B7-2 expressed on CHO cells induced long term T cell proliferation of activated CD4+ T cells similarly to costimulation with anti-CD28 mAbs.

EXAMPLE 13

Differences in Cytokines Secreted from B7 Versus Anti-CD28 Stimulated T Cells in Short Term T Cell Cultures The experiments described in Examples 11 and 12 did not reveal any notable differences between B7-1, B7-2, or anti-CD28 mAb in the ability to provide a costimulatory signal for the induction or maintenance of T cell proliferation. To further test whether anti-CD28 or B7-1 and B7-2 mediated distinct costimulatory effects, the accumulation of various cytokines was examined in T cell subsets. To first assess global effects of B7 costimulation on T cells, CD28+ T cells were stimulated with plastic immobilized anti-CD3 mAb and titered amounts of B7-1 or B7-2 CHO transfectants or anti-CD28 mAb 9.3 at 1 µg/ml. Anti-CD3 mAb (OKT3) was precoated on the culture wells by overnight incubation with a 10 µg/ml solution. Supernatants of the T cell cultures were collected after 24 h of culture and analyzed by ELISA using commercially available kits. The kits were obtained from the following sources: IL-2, T Cell Diagnostics, Cambridge, Mass.; TNF-alpha, GM-CSF, IL-4, and IL-5, R&D Systems, Minneapolis, Minn.; Interferon-gamma, Endogen, Boston, Mass. All values were assessed by using dilutions of culture supernatant that yielded readouts within the linear portion of the standard curve. The cytokine production data is summarized below in Table 3.

No cytokines were detected in supernatants from cells cultured in media alone, as would be expected with resting T cells. Similarly, anti-CD3 did not elicit detectable amounts of IL-2, although low levels of IFNγ, TNF-α and GM-CSF were present after anti-CD3 stimulation alone. Addition of either B7-1 or B7-2 CHO cells resulted in a dose dependent increase in cytokines. The costimulatory effect was most marked in the case of IL-2, as both B7-1 and B7-2 resulted in 100-fold or more augmentation of IL-2 secretion in comparison to CD3 plus control CHO cell cultures. There was also a dose-dependent increase in IFN-γ, IL-4, TNF-α and GM-CSF secretion induced by B7-1 and B7-2. Importantly, B7-1 and B7-2 costimulation elicited nearly equivalent amounts of all tested cytokines. There were however some differences between the amount of cytokines secreted by cells stimulated with anti-CD28 mAb as compared to B7-1 or B7-2; most notably, both B7-1 and B7-2 were associated with higher levels of IL-4 secretion (B7-1, 200; B7-2, 250; anti CD28, <20 pg/ml).

TABLE 3

Effects of B7-1 and B7-2 on Lymphokine Production by CD28+ T Cells.
(cytokine concentration in pg/ml)

| Culture Condition (CHO cell/T cell ratio) | IL-2 | IFN-γ | IL-4 | TNFα | GM-CSF |
| --- | --- | --- | --- | --- | --- |
| Medium | <60 | <10 | <20 | <30 | <100 |
| αCD3+CHO-B7-1(0.1) | 1790 | 2640 | 62 | 1250 | 2490 |
| αCD3+CHO-B7-1(0.2) | 2250 | 3880 | 110 | 1690 | 3110 |
| αCD3+CHO-B7-1(0.4) | 4040 | 4430 | 149 | 1910 | 3260 |
| αCD3+CHO-B7-1(0.8) | 5500 | 5930 | 200 | 2110 | 3670 |
| αCD3+CHO-B7-2(0.1) | 1620 | 3470 | 70 | 1310 | 2990 |
| αCD3+CHO-B7-2(0.2) | 3640 | 5490 | 145 | 2040 | 4040 |
| αCD3+CHO-B7-2(0.4) | 5826 | 7640 | 220 | 2440 | 4420 |
| αCD3+CHO-B7-2(0.8) | 6830 | 8610 | 250 | 2410 | 4260 |
| αCD3+CHO-neo(0.1) | <60 | 480 | <20 | 670 | 520 |
| αCD3+CHO-neo(0.2) | <60 | 650 | <20 | 690 | 570 |
| αCD3+CHO-neo(0.4) | <60 | 690 | <20 | 745 | 800 |
| αCD3+CHO-neo(0.8) | <60 | 690 | <20 | 605 | 725 |
| αCD3 only | <60 | 280 | <20 | 380 | 280 |
| αCD3+CD28 Mab 9.3 | 1630 | 860 | <20 | 1760 | 2090 |

As shown in Table 3, B7-1 and B7-2-induced cytokine accumulation appeared to plateau at similar ratios of CHO cells to T cells (about 0.4 CHO cells:T cell), suggesting that a failure to detect differences between B7 receptors was not due to a differential dose response between B7-1 and B7-2. Further, this indicates that neither B7 receptor had been tested under limiting conditions. However, it was possible that differential effects of B7-1 and B7-2 exist, and that this would be apparent only in T cell subsets. Alternatively, it was possible that intrinsic differences between B7-1 or B7-2 would only be revealed after repeated T cell costimulation, to permit possible cellular differentiation.

To assess whether distinct T cell subsets might differentially respond to B7-1 or B7-2, CD28+ T cells were divided into CD28+CD4+ and CD28+CD8+ cells and into CD4+CD45RO+ and CD4+CD45RA+ subsets. To obtain CD28+CD4+ or CD28+CD8+ T cells, the CD28+ T cells were subjected to a second round of negative selection using magnetic beads (Dynal) coated with CD8 or CD4 mAb as described in June et al. (1989) *J. Immunol.* 143:153. CD4+CD45RO+ and CD4+CD45RA+ subpopulations were isolated by subjecting CD28+ T cells to negative selection using magnetic beads and anti-CD45RO monoclonal antibody UCHL1 or anti-CD45RA monoclonal antibody ALB 11 (Immuntech).

To examine cytokine production, cells were stimulated with plastic-immobilized anti-CD3 Abs and CHO-B7-1 or CHO-B7-2 cells or with plastic beads expressing both anti-CD3 and anti-CD28 (as described above). The results are summarized below in Table 4. Table 4 shows that B7-1 and B7-2 elicited similar amounts of IL-2 secretion from CD4+ T cells. Both receptors stimulated CD8+ T cells with equal efficiency, however about 4-fold less IL-2 accumulated in the supernatants from CD8+ T cells. Anti-CD28 caused potent costimulation of IFNγ in both CD4+ and CD8+ T cell subsets. B7 receptors could also elicit high levels of IFN-γ from either subset, although the magnitude of the effect was two to four-fold less than anti-CD28 mAb stimulation.

TABLE 4

Effects of B7-1 and B7-2 on lymphokine production by
CD4+ and CD8+ T cells
(cytokine concentrations in pg/ml)

| Culture Condition | IL-2 | IFN-γ | GM-CSF |
|---|---|---|---|
| CD4+ Cells | | | |
| medium | <60 | <15 | <15 |
| αCD3 | 93 | 1270 | 9770 |
| αCD3+CD28 mAbs | 87500 | 44200 | 77300 |
| αCD3+CHO-neo | 60 | 1760 | 9380 |
| αCD3+CHO-B7-1 | 5320 | 14200 | 32400 |
| αCD3+CHO-B7-2 | 3940 | 18300 | 30100 |
| CD8+ Cells | | | |
| medium | <60 | <15 | <15 |
| αCD3 | 133 | 1620 | 8900 |
| αCD3+CD28 mAbs | 53600 | 26200 | 69600 |
| αCD3+CHO-neo | 100 | 3530 | 8830 |
| αCD3+CHO-B7-1 | 1360 | 10700 | 20600 |
| αCD3+CHO-B7-2 | 1320 | 14600 | 20700 |

It was surprising that CD8+CD28+ T cell cultures accumulated similar amounts of IL-2, IFN-γ and GM-CSF as did CD4+CD28+ cells. The CD8+ subpopulation contained <2% CD4+ cells, and thus contamination of the CD8+ cells by CD4+ cells can not explain the nearly equivalent levels of cytokine secreted by the CD4 and CD8 subsets. In the experiment shown in Table 4, cells were stimulated with beads expressing both anti-CD3 and anti-CD28 mAbs ("cis" stimulation), while in the experiment shown in Table 3, plastic-immobilized anti-CD3 plus fluid phase anti-CD28 ("trans") costimulation was used. "Cis" stimulation was consistently more efficient at eliciting cytokine accumulation (Table 4 vs. Table 3, and see FIGS. 25 and 26 below).

The costimulatory signals provided by anti-CD28, B7-1 and B7-2 were similarly potent in eliciting accumulation of GM-CSF (Tables 3 and 4). This is most apparent if the fold elevation above anti-CD3 mAb only, or control CHO cultures is examined when comparing cultures stimulated with anti-CD28 or B7-1 and B7-2. With regard to TNFα, both B7-1 and B7-2 had similar costimulatory effects on CD4+ T cells.

Figure 23F:
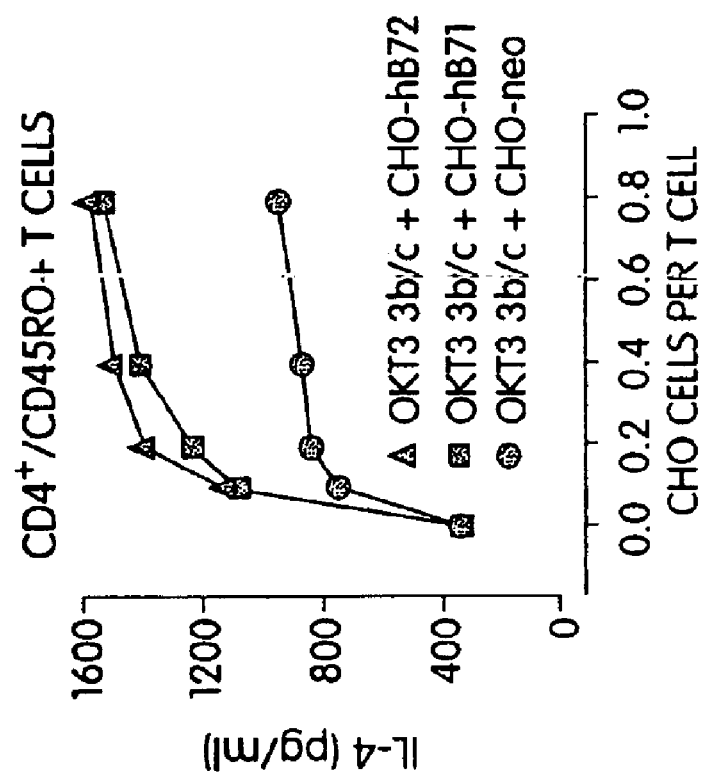
FIG. 23 shows the amounts of IL-2 and IL-4 produced from $CD4^+$ T cells (panels A and B), $CD4^+/CD45RA^+$ T cells (panels C and D) and $CD4^+/CD45RO^+$ cells (panels E and F) stimulated with anti-CD3 monoclonal antibody coated beads and B7-1, B7-2, or control CHO-neo cells at the indicated CHO cell to T cell ratio.
Figure 23E:
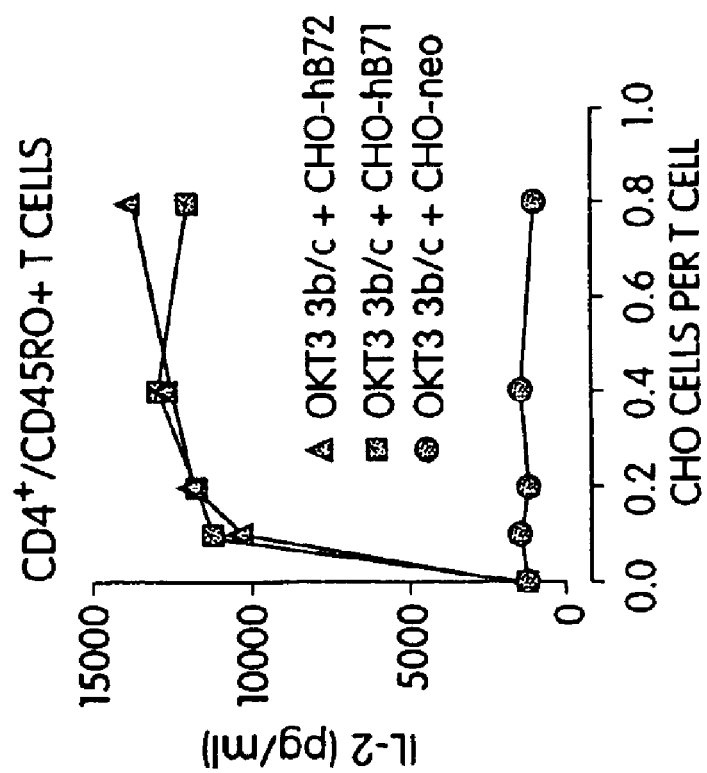
Figures 24A, 24B, 24C, 24D:
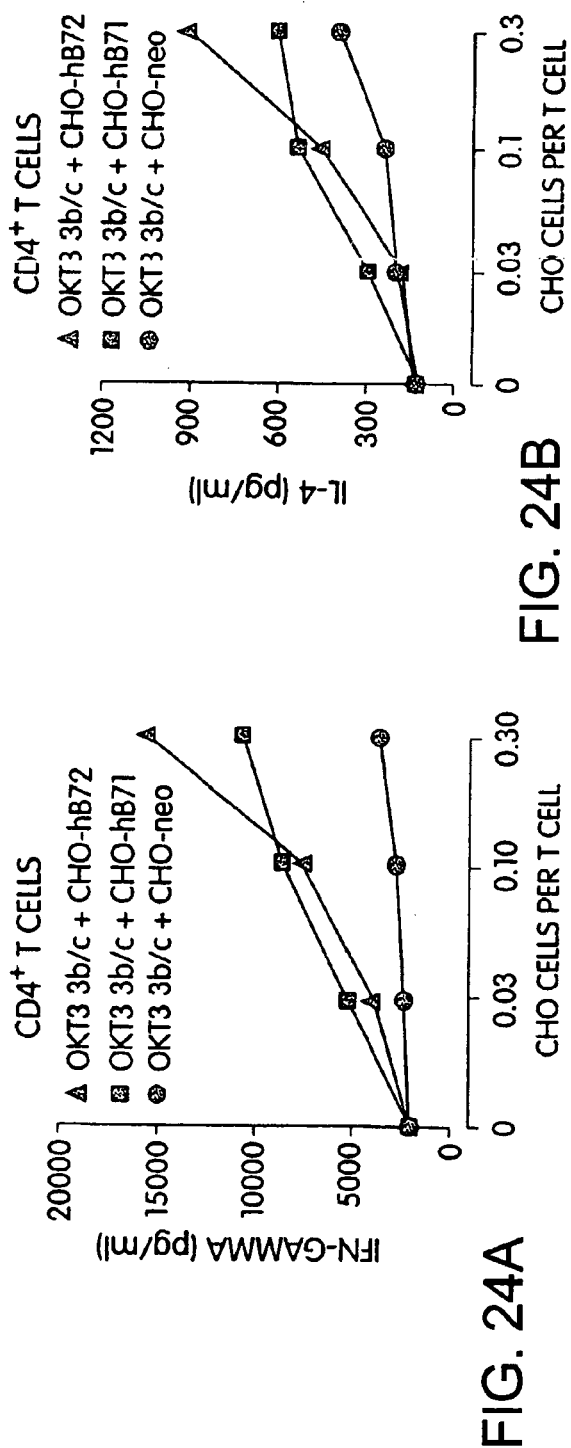
FIG. 24 shows the amounts of interferon-gamma and IL-4 produced from $CD4^+$ T cells (panels A and B), $CD4^+/CD45RA^+$ T cells (panels C and D) and $CD4^+/CD45RO^+$ T cells (panels E and F) stimulated with anti-CD3 monoclonal antibody coated beads and B7-1, B7-2, or control CHO-neo cells at the indicated CHO cell to T cell ratio.
Figure 24F:
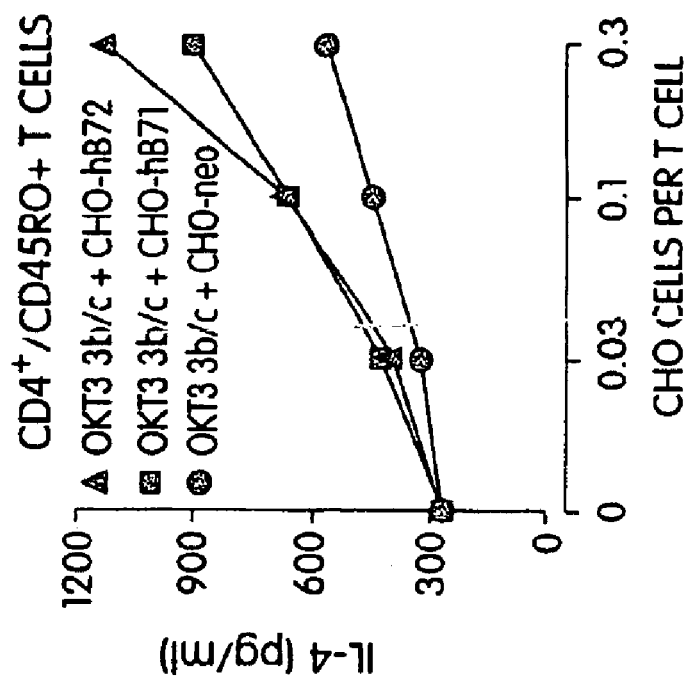
Figure 24E:
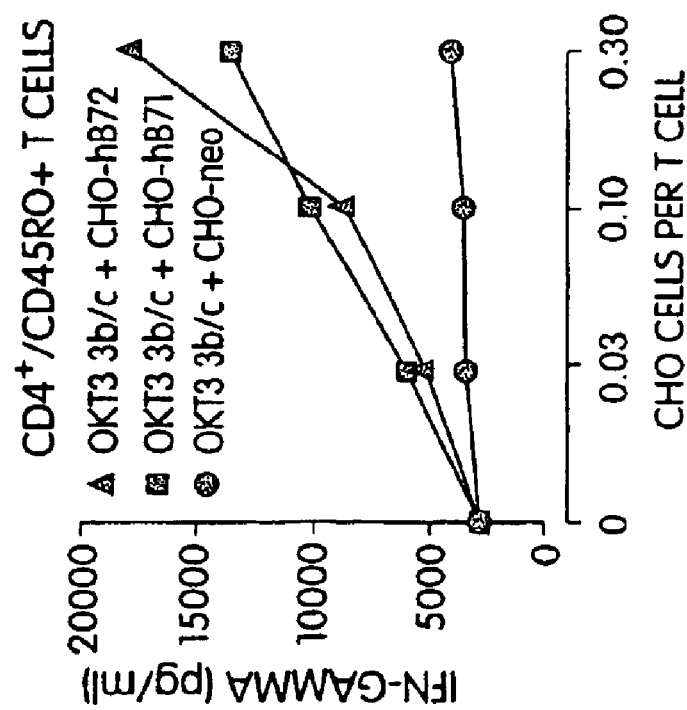

While the effects of B7-1 and B7-2 appeared quite similar on CD4+ and CD8+ T cell subsets, it remained possible that distinct functions might be revealed in CD4 subsets. Purified CD4+ T cells were magnetically sorted into "virgin" CD45RA+ and "memory" CD45RO+ populations as described above. The cells were then tested for their ability to secrete IL-2, IL-4 and IFNγ after stimulation with anti-CD3 mAb coated beads in the presence of B7-1 or B7-2-expressing CHO or control neo-CHO cells (see FIGS. 23 and 24). The experiment in FIG. 23 was carried out in R10 medium and the experiment of FIG. 24 was carried out in Aim V medium. Supernatants were harvested after 24 hours of culture, and cytokine concentrations were measured by ELISA as described above. Both B7-1 and B7-2 were able to costimulate both subsets to equivalent levels of proliferation. However, striking differences were uncovered in the induction of cytokine secretion by B7 from CD45RO+ and CD45RA+ subpopulations. B7-1 and B7-2 costimulation resulted in the secretion of large amounts of IL-2 from both subsets (FIG. 23, left hand panels). In contrast, neither B7-1 nor B7-2 could elicit IL-4 (FIGS. 23 and 24, right hand panels) or IFNγ (FIG. 24, left hand panels) from the CD45RA+ subpopulation. Since both B7-1 and B7-2 were tested at a variety of T cell to CHO cell ratios, ensuring that responses were assessed at plateau levels of costimulation, it is unlikely that either receptor has a differential costimulatory function on CD4+ T cells with naive and memory phenotypes. Furthermore, no differential sensitivity or priming of these cellular subsets to low levels of B7 stimulation was observed; B7-1 and B7-2 mediated lymphokine responses occurred at similar thresholds in both naive and memory subsets.

EXAMPLE 14

Differential Cytokine Secretion upon Costimulation with Anti-CD28 in "cis", in "Trans", or with B7 Molecules in Long Term Culture The experiments described in Examples 11, 12 and 13 indicate that B7 receptors have similar costimulatory effects on the cytokines produced during the first round of T cell activation and division, and indicate that CD4 subpopulations have differential capacity to secrete cytokines. In this example, differences in the ability of B7-1 or B7-2 to induce differentiation were investigated. CD4+ CD28+ T cells were stimulated with anti-CD3 in the presence of CHO cells expressing B7-1 or B7-2, or with anti-CD3 plus CD28 mAbs on beads in "cis" as described in Example 12. The cells were maintained in exponential growth during the experiment. Supernatants were collected after 24 hours of culture and on day 11, cells were washed and placed in fresh medium, restimulated with fresh anti-CD3 and CHO cells, and supernatants collected after a further 24 hours culture. Cytokine levels were measured as described above.

Figure 25A:
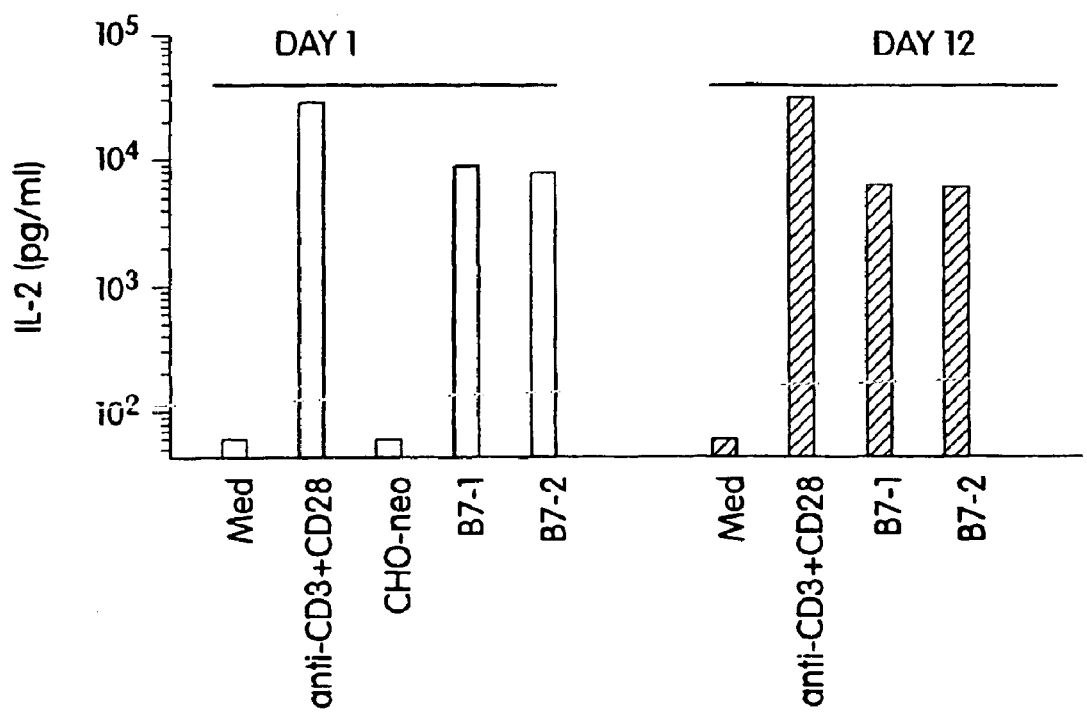
FIG. 25 shows the amounts of IL-2 (panel A) and IL-4 (panel B) produced from CD4+ T cells stimulated with medium alone, anti-CD3 monoclonal antibody and B7-1, B7-2, control CHO-neo cells after the first round of stimulation (day 1) or a second round of stimulation (day 12).
Figure 25B:
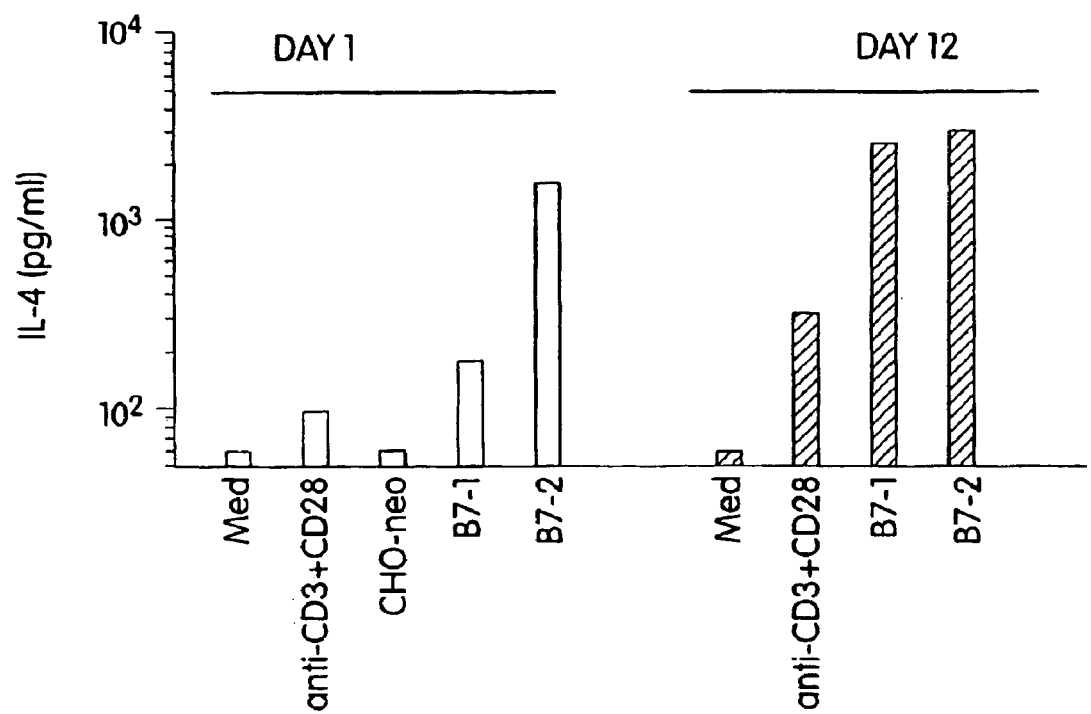
Figure 26A:
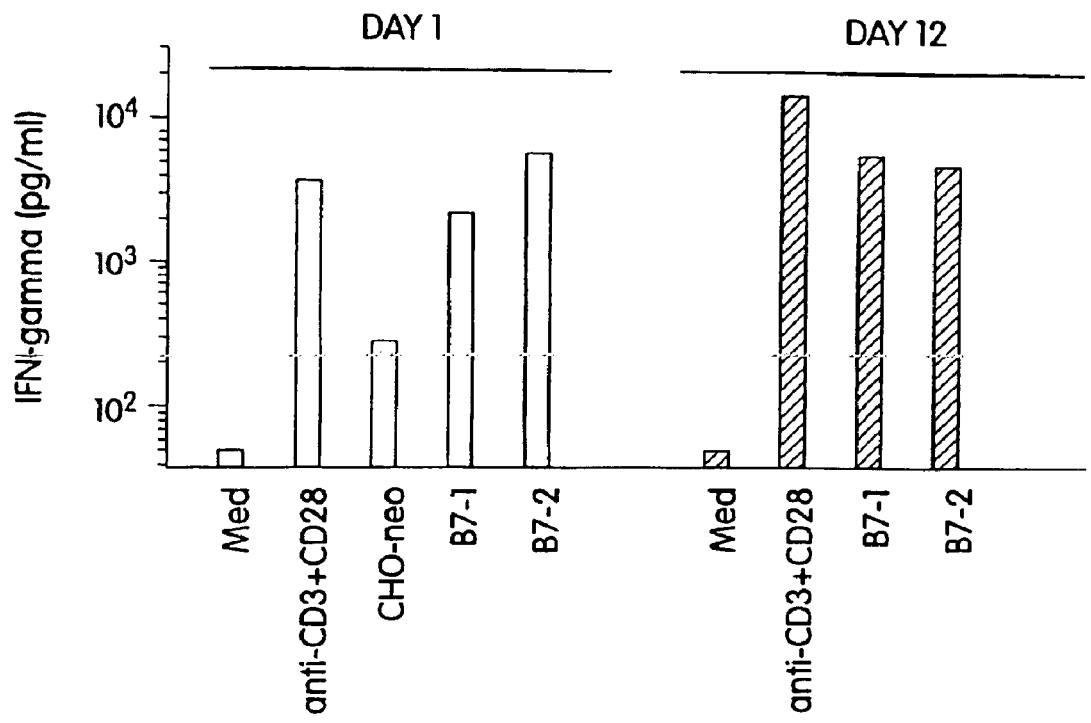
FIG. 26 shows amounts of interferon-gamma (panel A) and IL-5 (panel B) produced from CD4+ T cells stimulated with medium alone, anti-CD3 monoclonal antibody and B7-1, B7-2, control CHO-neo cells after the first round of stimulation (day 1) or a second round of stimulation (day 12).
Figure 26B:
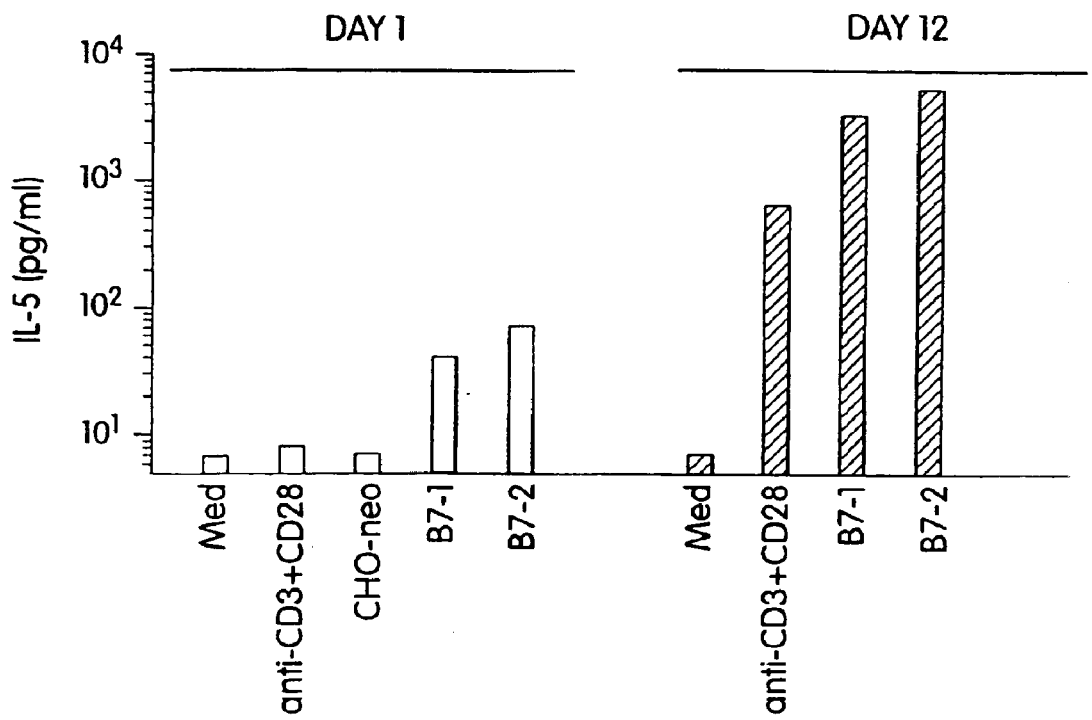
Figure 27A:
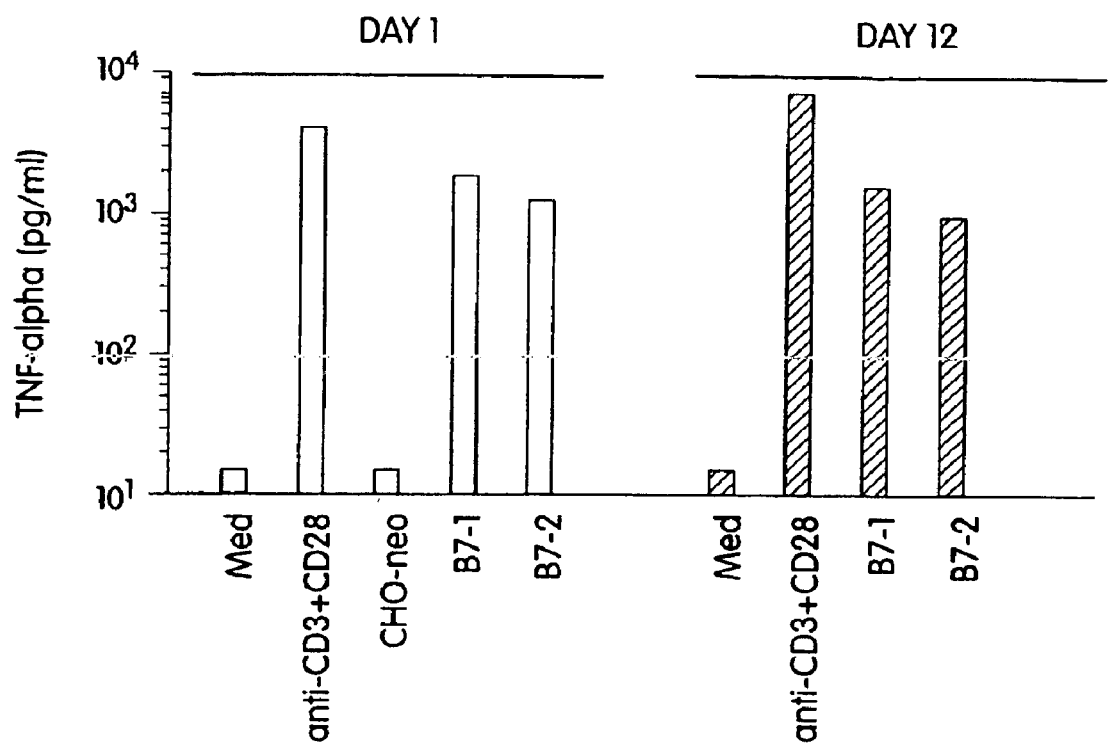
FIG. 27 shows amounts of TNF-alpha (panel A) and GM-CSF (panel B) produced from CD4+ T cells stimulated with medium alone, anti-CD3 monoclonal antibody and B7-1, B7-2, control CHO-neo cells after the first round of stimulation (day 1) or a second round of stimulation (day 12).
Figure 27B:
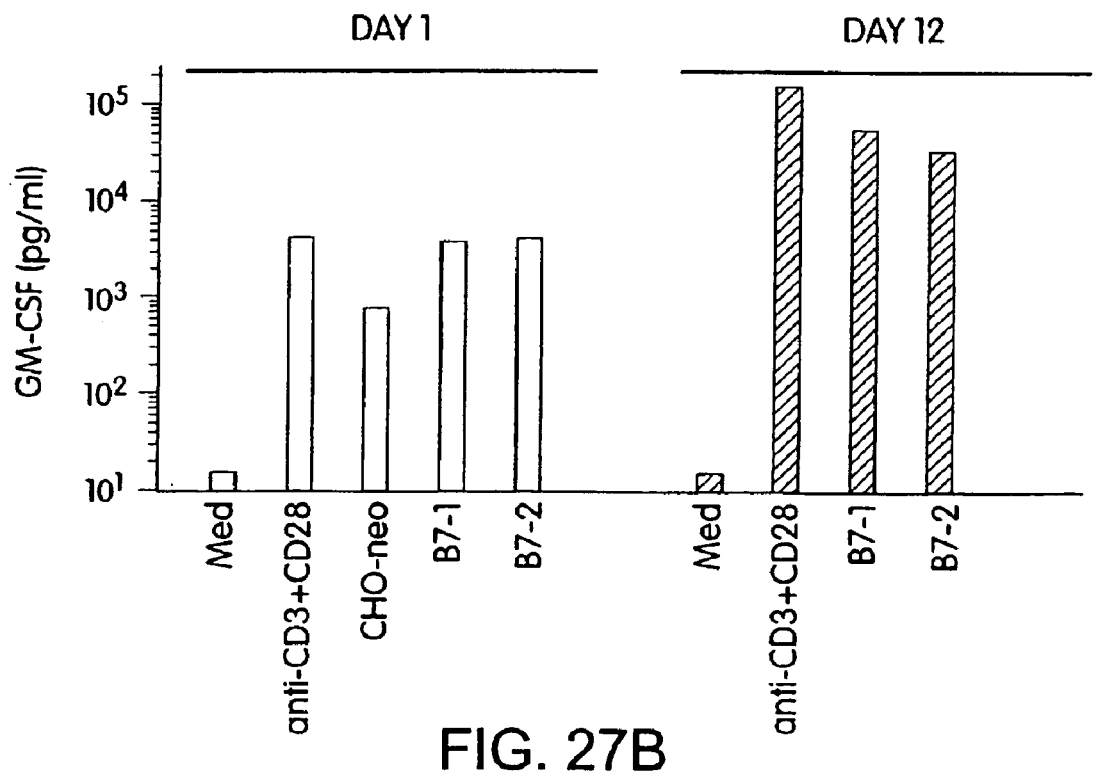

The results are shown graphically in FIGS. 25–27. During the initial 24 hours of activation, B7-1 and B7-2 induced nearly equivalent amounts of IL-4, and this was more than that induced by anti-CD28 (FIG. 25, bottom panels). In contrast, costimulation with B7-1 and B7-2 did not elicit as much IL-2 as anti-CD28 stimulation during the first 24 hours (FIG. 25, top). These results are consistent with Table 4, where anti-CD28 stimulation in "cis" was also employed. However, on restimulation of cells with B7 receptors on day 12 of culture, about 10-fold more IL-4 accumulated when compared to the initial stimulation of resting T cells. The anti-CD28 mAb mediated increase in IL-4 secretion on restimulation was not as striking as with B7 restimulation. In contrast, anti-CD28 was more efficient than B7 in the induction of IL-2 secretion during restimulation.

IL-5 secretion was not detectable after primary stimulation with anti-CD3 and anti-CD28, while both B7-1 and B7-2 resulted in low-level IL-5 secretion of similar magnitude during the first day of stimulation (FIG. 25, bottom). A notable increase in B7-1 and B7-2-mediated IL-5 secretion occurred on day 12 restimulation. IL-5 secretion also increased after anti-CD28 restimulation, however, the increase was about 8 to 10-fold less than that due to B7 restimulation. Thus, the pattern of IL-5 secretion is similar to that of IL-4 (FIG. 25 vs. 26, bottom panels).

The effects of restimulation on IFNγ were also examined. High level IFNγ secretion occurred within 24 hours after B7 and anti-CD28 primary stimulation (FIG. 26, top), consistent with Table 4. At restimulation, however, anti-CD28 was superior to both B7 receptors. Thus, the pattern of anti-CD28 and B7-mediated IFNγ secretion is similar to that of IL-2, and the pattern of IL-5 secretion is similar to that of IL-4 (FIGS. 25 vs. 26).

FIG. 27 shows the effects of anti-CD28 and B7 restimulation on GM-CSF and TNFα secretion by CD4+ T cells. With regards to GM-CSF, both anti-CD28 and B7-1 and B7-2 increased GM-CSF secretion, although the fold costimulation was more modest, at 4 to 8-fold over that induced by anti-CD3 plus control CHO cells (FIG. 27, bottom). On restimulation, there were no consistent differences between the various CD28 ligands in the ability to promote GM-CSF secretion. In contrast, anti-CD28 was more effective than B7 receptors at maintaining TNFα secretion on restimulation (FIG. 27, top). Thus, during the initial activation of T cells, and during reactivation of CD4+ T cell blasts in vitro, no consistent differences between B7-1 and B7-2 could be identified in any of the cytokines examined. Interestingly however, anti-CD28 mAb favored IL-2, IFNγ, and TNFα secretion, while B7-1 and B7-2 promoted IL-4 and IL-5 secretion. Thus, costimulation with B7-1 or B7-2 resulted in preferential secretion of TH2-specific cytokines, whereas costimulation with anti-CD28 resulted in preferential secretion of TH1-specific cytokines.

The above results did not reveal any consistent differences in the induction of cytokine secretion by B7-1 and B7-2 while differences between anti-CD28 and B7 were observed in FIGS. 25–26 and in Table 3. To determine a potential mechanism for these differences, CD28+ T cells were cultured in the presence of anti-CD3 plus anti-CD28 beads in "cis" (both antibodies on the same bead) or in "trans" (both antibodies on different beads). For "cis" stimulation, immunomagnetic beads were coated with OKT3 and 9.3 mAbs with each antibody added at 150 femtograms per bead and added at a ratio of 3 beads per T cell. For "trans" stimulation, an equal amount anti-CD3 and anti-CD28 coated beads were added at a ratio of 3 (of each type) beads per T cell. In addition, cells were cultured with anti-CD3 plus anti-CD28 beads in "cis" with mitomycin-inactivated CHO-neo cells added at a ratio of 2.5:1 T cell to CHO cell, as a control for factors intrinsic to CHO cells. Finally, T cells were cultured with anti-CD3 beads and CHO-B7-1 cells at a ratio of 2.5:1 T cell to CHO cell. The cells were cultured as indicated in Example 12.

Figure 28A:
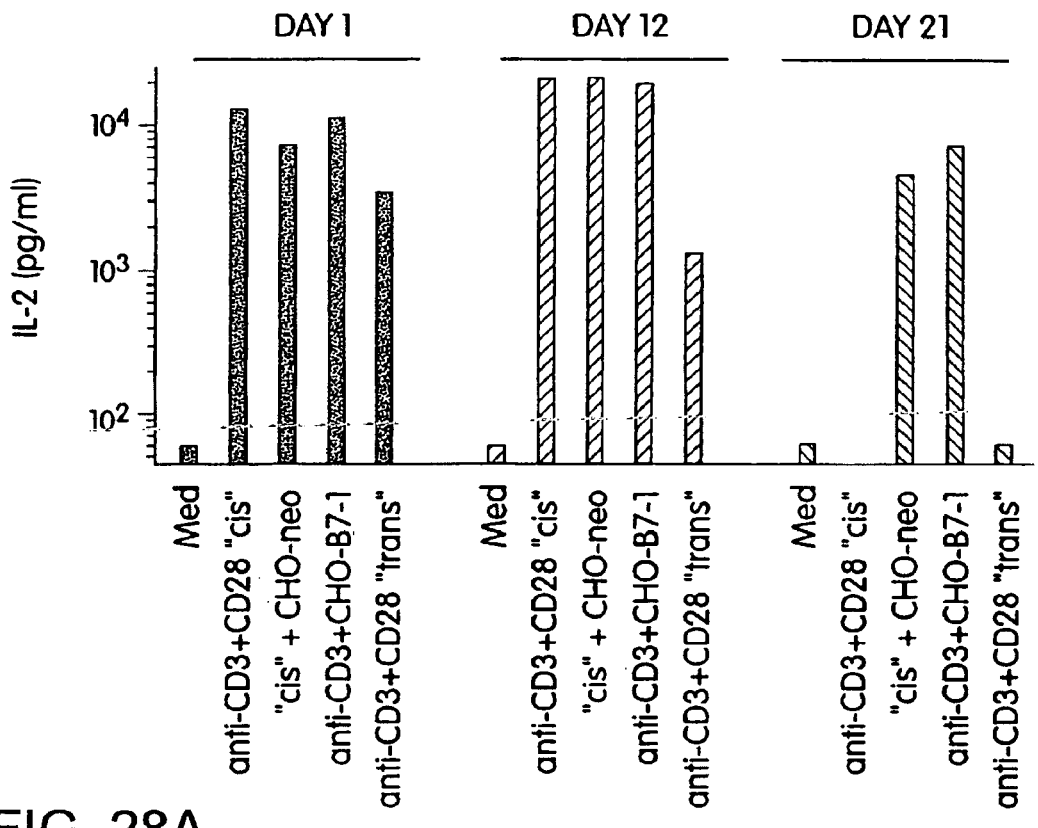
FIG. 28 shows the amounts of IL-2 (panel A) and IL-4 (panel B) secreted from CD28+ T cells stimulated with medium alone, anti-CD3 and anti-CD28 antibody coated beads ("cis"), anti-CD3 and anti-CD28 antibody coated beads and control CHO-neo cells ("cis"+ CHO-neo), anti-CD3 coated beads and B7-1 CHO cells (anti-CD3+CHO-B7-1), or anti-CD3 coated beads and anti-CD28 coated beads (anti-CD3+CD28 "trans") after initial stimulation (day 1), second stimulation (day 2), or third stimulation (day 3).
Figure 28B:
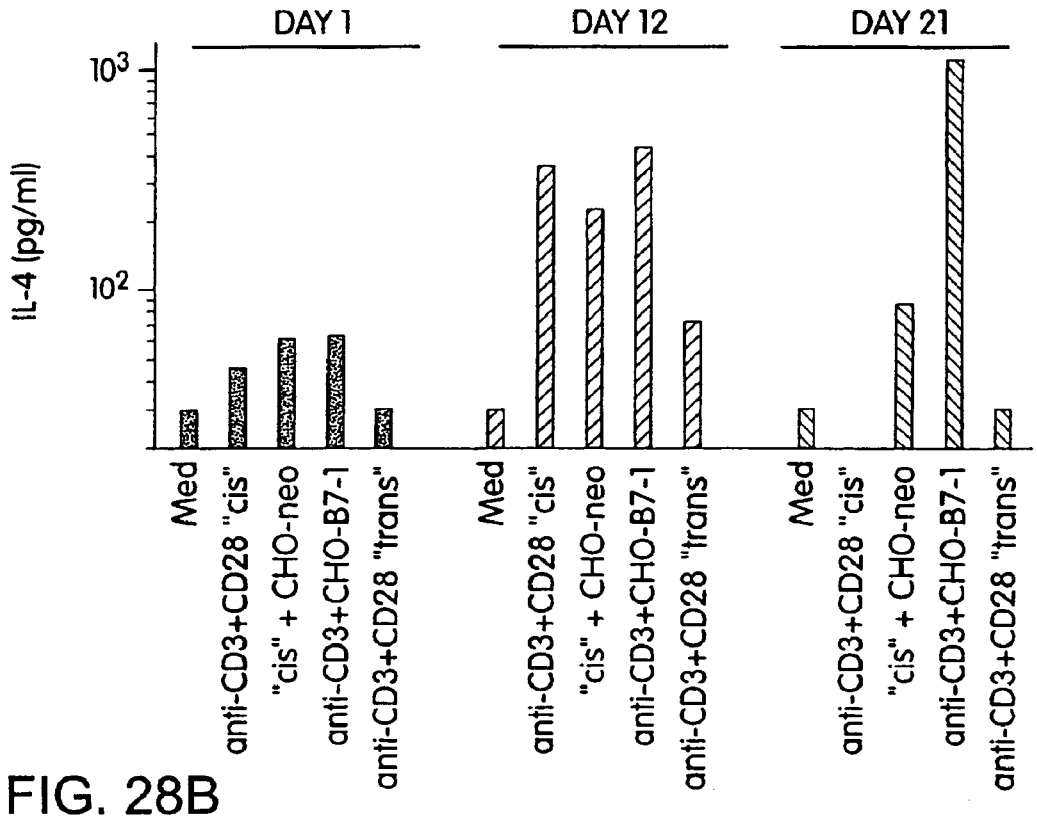
Figure 29:
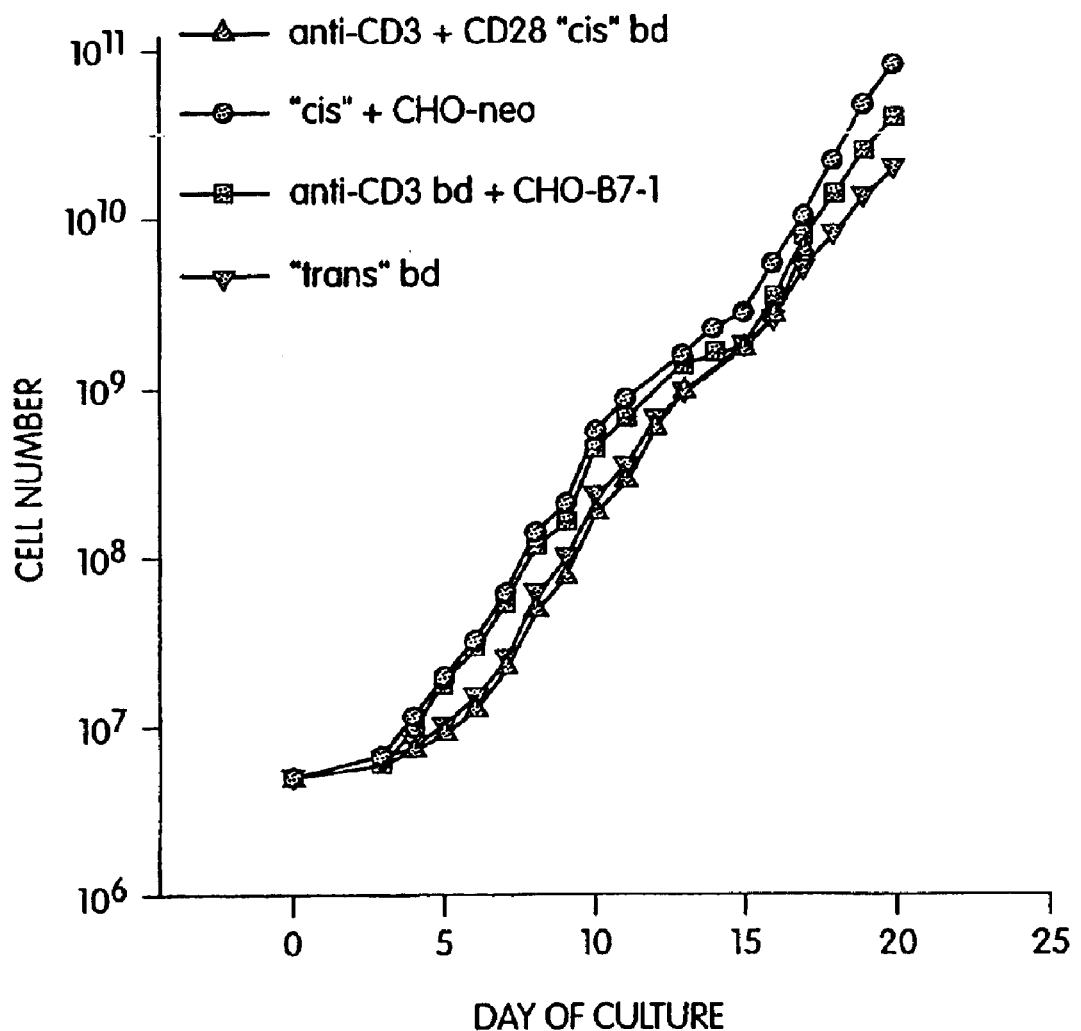
FIG. 29 depicts growth curves of the CD28+ T cells stimulated in the experiment shown in FIG. 28.

The results of these experiments are shown graphically in FIGS. 28–29. All conditions induced exponential expansion of CD4 T cells (FIG. 29). However, there were differences in the cytokines induced by these forms of costimulation (FIG. 28). Cells stimulated with anti-CD28 in "cis" or with anti-CD28 in "cis" plus CHO-neo cells maintained high levels of IL-2 secretion. In contrast, anti-CD28 stimulation in "trans" was less efficient at inducing IL-2 secretion, and this form of costimulation was progressively less efficient upon repetitive restimulation. The anti-CD3 plus CHO-B7-1 stimulation in "trans" was the only condition that resulted in progressively increasing amounts of IL-4 secretion, consistent with the results shown in FIG. 26 and Table 3. Together, the above results demonstrate that B7-1 and B7-2 both have the ability to stimulate T cell proliferation and cytokine secretion and that the manner of CD28 costimulation can have substantial effects on the patterns of cytokine secretion.

EXAMPLE 15
Cell Death by Apoptosis of CD8+ T Cells Costimulated with Anti-CD28

Previous information in this application shown in FIG. 4 has shown that CD28 costimulation can favor the growth of CD4+ T cells. To determine a mechanism for this effect, CD8+ T cells were isolated by negative immunomagnetic selection. The cells were stimulated with anti-CD3 antibody coupled to beads (b) or to a solid phase (SP) i.e., tissue culture dish plus anti-CD28 in "cis" or in "trans". The induction of apoptosis was assessed by detecting single strand DNA breaks using a flow cytometric TdT assay (Gorczyca, W., J. Gong, and Z. Darzynkiewicz 1993. Detection of DNA strand breaks in individual apoptotic cells by the in situ terminal deoxynucleotidyl transferase and nick translation assays. *Cancer Res.* 53:1945). During the first 48 hours of culture (S1), the cells became activated and <10% of cells underwent apoptosis (Table 5). The cells were restimulated twice with anti-CD3 and anti-CD28 when required and the induction of apoptosis again assesed 24 to 48 hours following each restimulation (S2 and S3). A dramatic increase in DNA breaks was uncovered. This was not prevented with the addition of recombinant IL-2 (rIL-2) at 100 U/ml.

TABLE 5

Apoptosis assays of CD8+ T cells costimulated with anti-CD28

| Stimulation | % TdT Positive by Flow Cytometry | | |
|---|---|---|---|
| | T0 | T24 hr | T48 hr |
| S1 | | | |
| OKT3/9.3 3b/c | 2 | 6 | 1 |
| OKT3 3b/c + 9.3 3b/c | 2 | 3 | 1 |
| OKT3 3b/c + soluble 9.3 | 2 | 3 | 1 |
| OKT3sp + soluble 9.3 | 2 | 1 | 2 |
| Medium | 2 | 2 | 2 |
| S2 | | | |
| OKT3/9.3 3b/c + rhIL2 | 40 | 15 | 39 |
| OKT3 3b/c + 9.3 3b/c | 22 | 47 | 63 |
| OKT3 3b/c 9.3 3 3b/c + rhIL2 | 22 | 55 | 34 |
| OKT3 3b/c + soluble 9.3 | 27 | 70 | 72 |
| OKT3 3b/c + soluble 9.3 + rhIL2 | 27 | 76 | 59 |
| S3 | | | |
| OKT3/9.3 3b/c | | 67 | |
| OKT3/9.3 3b/c + rhIL2 | 11 | 75 | |
| OKT3 3b/c + 9.3 3b/c + rhIL2 | 19 | 52 | |

It was next determined if the induction of apoptosis in CD8+ T cells was specific to the CD8+ T cell subset. CD4+ and CD8+ T cells were isolated and stimulated separately with anti-CD3 and anti-CD28 antibodies. During the first 48 hours of culture (S1), there was little evidence of programmed cell death in either the CD4 or the CD8+ T cell subsets. In contrast, on restimulation (S2), there was a marked induction of cell death in the CD8+ T cell subset (Table 6). Again, this was not prevented by addition of exogenous IL-2. Thus, the selective induction of CD8+ T cell death is one mechanism that permits CD28 stimulation to enhance CD4+ T cell expansion. The absence of programmed cell death in the CD4+ T cells is consistent with the observations shown elsewhere in this application that the CD4+ cells remain polyclonal for extended periods of culture.

TABLE 6

Apoptosis assays of CD4 and CD8+ T cells

| CD4 and CD8 T cells | % TdT Positive by Flow Cytometry | | |
|---|---|---|---|
| | T0 | T24 hr | T48 hr |
| S1 | | | |
| CD4 OKT3/9.3 3b/c (cis) | 5 | 10 | 9 |
| CD4 OKT3 3b/c + rhIL2 | 5 | 9 | 9 |
| CD4 OKT3 3b/c + 9.3 3b/c (trans) | 5 | 12 | 11 |
| CD8 OKT3/9.3 3b/c (cis) | 3 | 6 | 3 |
| CD8 OKT3 3b/c + rhIL2 | 3 | 6 | 12 |
| CD8 OKT3 3b/c + 9.3 3b/c (trans) | 3 | 7 | 9 |
| S2 | | | |
| CD4 OKT3/9.3 3b/c (cis) | 6 | 18 | 13 |
| CD4 OKT3 3b/c + rhIL2 | 4 | 27 | 9 |

TABLE 6-continued

Apoptosis assays of CD4 and CD8+ T cells

| CD4 and CD8 T cells | % TdT Positive by Flow Cytometry | | |
|---|---|---|---|
| | T0 | T24 hr | T48 hr |
| CD4 OKT3 3b/c + 9.3 3b/c (trans) | 6 | 13 | 15 |
| CD8 OKT3/9.3 3b/c (cis) | 8 | 63 | 47 |
| CD8 OKT3 3b/c + rhIL2 | 15 | 75 | 62 |
| CD8 OKT3 3b/c + 9.3 3b/c (trans) | 20 | 79 | 61 |

The selective cell death of CD8+ T cells and not CD4+ T cells will be useful in selectively enriching a population of T cells, for example CD28+ T cells in CD4+ T cells during expansion.

EXAMPLE 16
Expansion of CD4+ T Cells from HIV Infected Individuals

Figure 30:
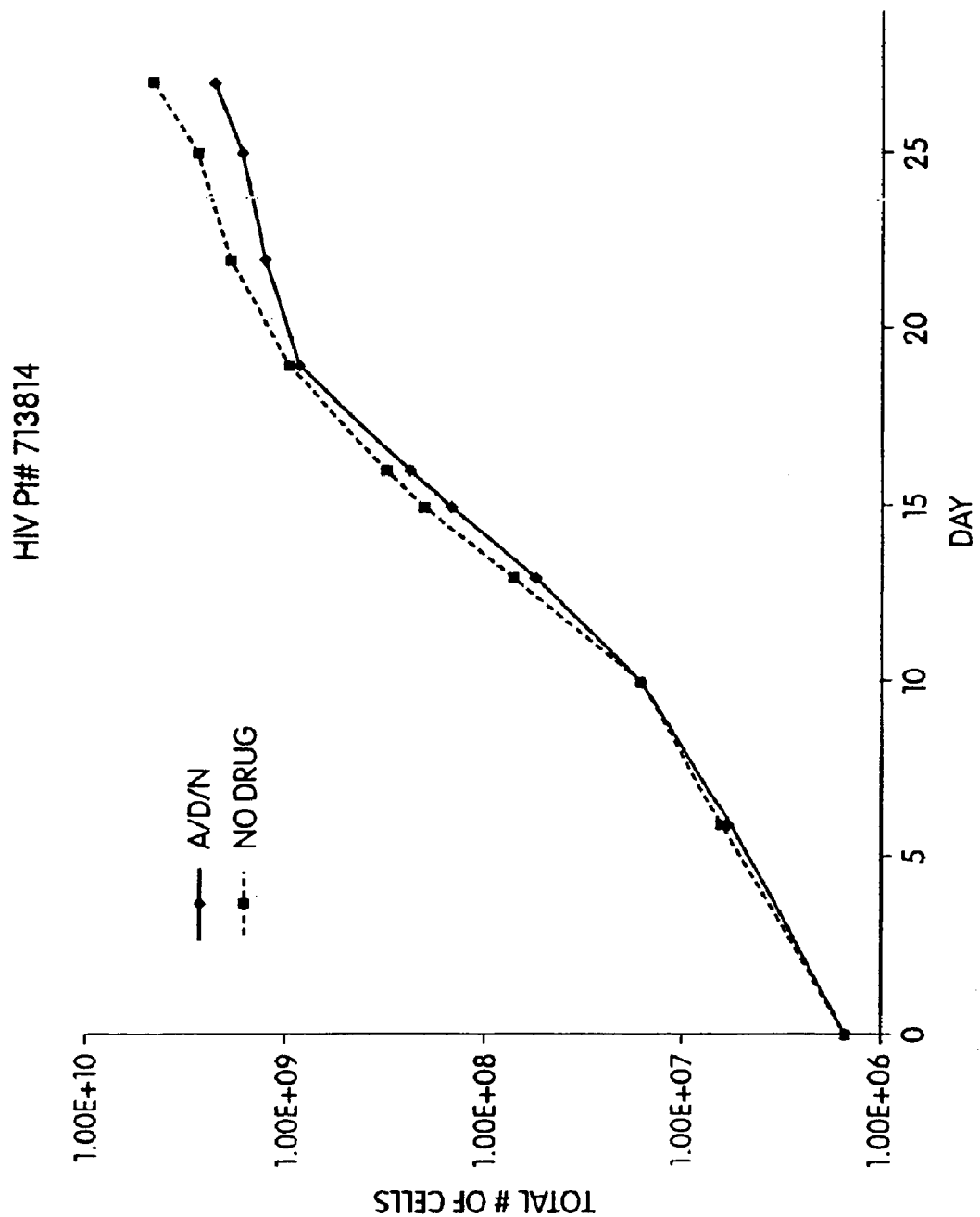
FIG. 30 depicts growth curves of CD4+ T cells from an HIV infected individual stimulated with anti-CD3 and anti-CD28 antibodies in the presence (A/D/N) or absence (No Drug) of anti-retroviral drugs.

In order to determine whether CD4+ T cells from individuals infected with HIV can similarly be expanded ex vivo, CD4+ T cells were obtained from HIV infected individuals and activated with anti-CD3 and anti-CD28 coated beads (3 beads containing an equimolar amount of each antibody, per T cell) in the presence or absence of anti-retroviral drugs. CD4+ T cells from a patient with 430 CD4+ T cells/µl were isolated by negative selection as described in Example 12 and incubated in standard RPMI 10% fetal calf serum either in the presence or absence of the following anti-retroviral drugs: AZT (available from Burroughs-Wellcome) at 1 µM, DDI (available from Bristol Myers Squibb) at 1 µM, and Nevirapine (available from Boehringer Mannheim) at 1 µM. The growth curves of the cells are represented in FIG. 30. The T cells expanded exponentially by a factor of more than 10,000 fold either in the presence or absence of added anti-retroviral drugs. Moreover, the CD4+ T cells expanded to higher numbers in the absence of the drug. In addition, no significant amounts of HIV-1 was detected in either culture, as the amount HIVp24 present in the supernatant of the cultures (determined by the Spearmen-Karber method) was <50 pg/ml. The Spearmen-Karber method is described in Richman D. B., Johnson V. A., Mayrs V. L. 1993, In vitro evaluation of experimental agents for anti-HIV activity. Current Protocols in Immunology ch. 12.9, Colligan J. E., Kruisback A. M., Margolis D. H., Shevach E. M., Strober W. Ed. Greene and Wiley. Interscience NY.

To further investigate the finding that the amount of HIV produced in the CD4+ T cell cultures stimulated in the presence of anti-CD3 and anti-CD28 was very low, the extent of replication of the virus was compared directly between CD4+ T cells isolated from HIV (US 1 isolate) infected cells (according to Richman D. B., Johnson V. A., Mayrs V. L. 1993, In vitro evaluation of experimental agents for anti-HIV activity. Current Protocols in Immunology ch. 12.9, Colligan J. E., Kruisback A. M., Margolis D. H., Shevach E. M., Strober W. Ed. Greene and Wiley. Interscience NY.), stimulated with PHA (5 µg/ml) and IL-2 (100 U/ml) or with anti-CD3 and anti-CD28. The TCID$_{50}$ was determined by the method of Spearmen-Karber at days 7, 14, and 21 of the cultures. As shown in Table 7, there was a marked difference between the titer of virus in the supernatants of T cells stimulated with anti-CD3 and anti-CD28 coated beads (3 beads per T cell) as compared to the conventional method of propagation using PHA and IL-2. The mechanism for this interesting effect is not yet known, but it suggests another potential mechanism for "rescuing" uninfected CD4 cells in cultures from HIV seropositive patients.

TABLE 7

CD4+ T Cells stimulated by anti-CD3 and anti-CD28
do not support replication of HIV-1.

| | TCID$_{50}$ | | |
|---|---|---|---|
| Cell Stimulation | Day 7 | Day 14 | Day 21 |
| anti-CD3 + anti-CD28 | <64 | <64 | <64 |
| PHA + IL-2 | 18820 | >65000 | >65000 |

It was possible that CD28 causes the proliferation of a particular subset of lymphocytes that are resistant to infection by HIV-1. Alternatively, it was possible that the mechanism of stimulation per se was able to confer resistance or sensitivity to HIV infection/expression. To test these possibilities, PBMC were obtained from a normal blood donor, and either the purified CD4+ T ($10^5$ cells/well) cells or whole PBMC ($10^5$ cells/well) activated with PHA (5 µg/ml) or with anti-CD3 and anti-CD28 coated beads (3 beads per T cell). The cells were infected with a T cell trophic variant of HIV-1(US1) or a monocyte trophic variant (BAL) on day 2 of culture as described in Richman D. B., Johnson V. A., Mayrs V. L. 1993, In vitro evaluation of experimental agents for anti-HIV activity. Current Protocols in Immunology ch. 12.9, Colligan J. E., Kruisback A. M., Margolis D. H., Shevach E. M., Strober W. Ed. Greene and Wiley. Interscience NY. The level of virus expression was quantitated in the culture supernatants on day 7 as shown in Table 8 by the Spearmen-Karber method. In PBMC, high levels of virus were expressed if the cells were stimulated with PHA whereas very low or no levels of virus were detected in cultures stimulated with anti-CD3 and anti-CD28 antibodies. This result was obtained whether or not plastic adherent monocytes/macrophages (M/M) were added to the culture ($10^4$ cells per well).

TABLE 8

Virus titrations in PHA and CD3/CD28-stimulated PBMCs
with or without addition of monocytes/macrophages.

| Cell Group | US1 TCID$_{50}$ Day 7 | BAL TCID$_{50}$ Day 7 |
|---|---|---|
| PBMC + PHA | 332555 | 241029 |
| PBMC + anti-CD3/CD28 | 279 | 77 |
| CD4 cells + M/M + PHA | >390625 | >390625 |
| CD4 cells + M/M + anti-CD3/CD28 | 386 | 279 |
| CD4 cells anti-CD3/CD28 | 1012 | 386 |

Thus, stimulation of CD4+ T cells infected with HIV with anti-CD3 and anti-CD28 results in much lower amounts of HIV particles produced as compared to the conventional method of T cell stimulation with PHA and IL-2. Moreover, since exponential growth of the cells was observed for at least 40 days, this method could therapeutically be useful for ex vivo and in vivo expansion of CD4+ T cells from an individual infected with HIV.

Figure 31:
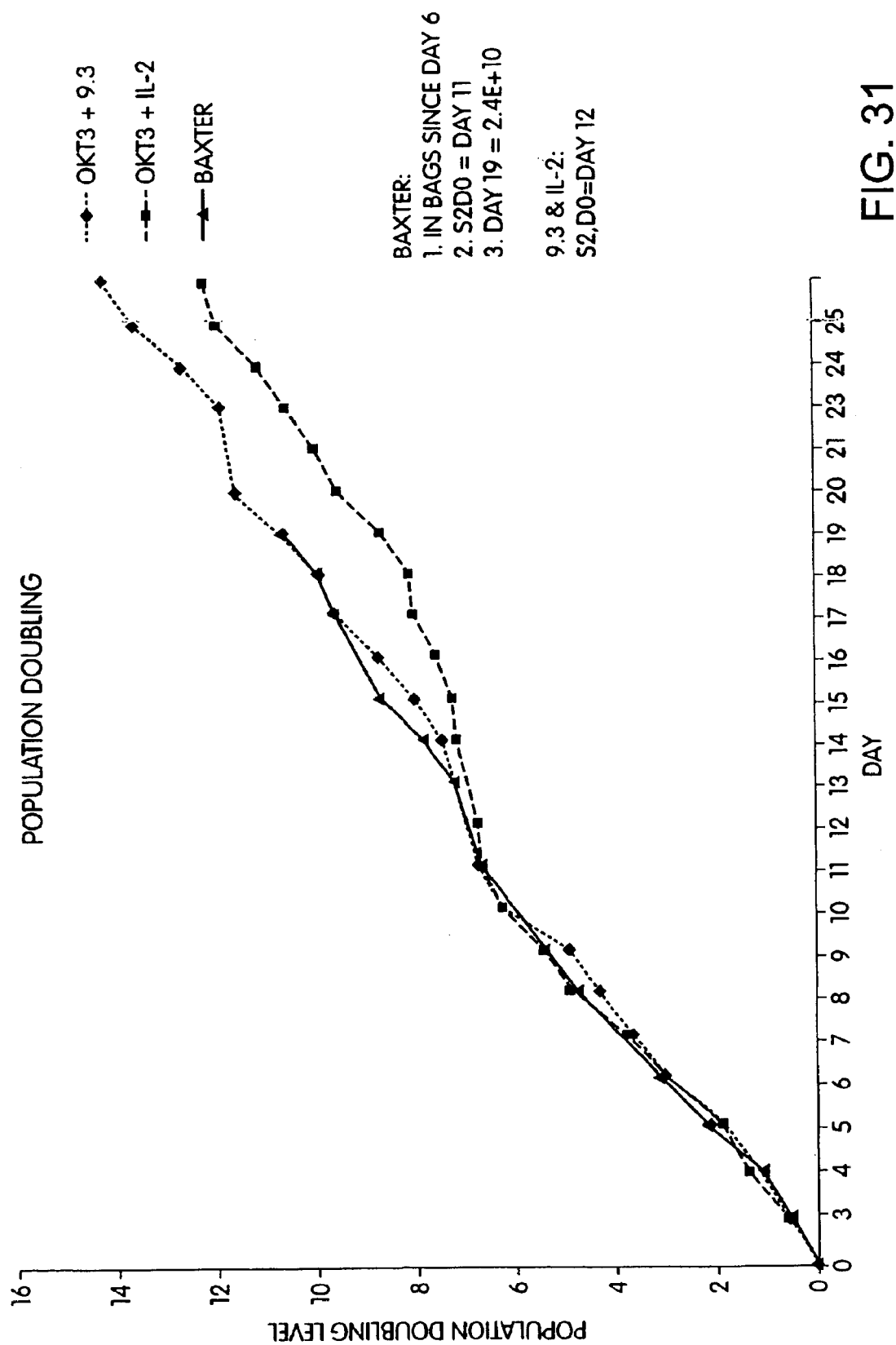
FIG. 31 depicts growth curves of CD4+ T cells stimulated with anti-CD3 and anti-CD28 coated beads in the presence of added IL-2 (OKT3+IL-2) or in the absence of added IL-2 (OKT3+9.3) in large scale cultures.

EXAMPLE 17
Large Scale Expansion of CD4+ T Cells Using Anti-CD3 and Anti-CD28 Antibodies To determine if the small scale expansion of T cells with anti-CD3 and anti-CD28 antibodies is also functional on a larger scale, required for clinical use, CD4+ T cells were obtained from a normal donor and cultured in either 3 liter gas-permeable bags (Baxter) or in T75 flasks (FIG. 31). The large scale culture system was seeded with 5×10⁷ cells. The cells were stimulated with a bead:cell ratio of 3:1 and the beads contained an equimolar amount of anti-CD3 (OKT3) and anti-CD28 (mAb 9.3) antibodies. The cells cultured in T75 were restimulated at day 12 (S2) wit anti-CD3 and anti-CD28 coated beads in the same conditions as for the first stimulation. The cells cultured in the gas-permeable bags were restimulated at day 11 (S2). No exogenous cytokines were added to the large scale culture system. The T75 flasks were carried out in duplicate, one containing exogenous IL-2 (100 $\mu$/ml) and the other with no added cytokine. The large scale culture grew equivalent to the small scale culture system, and was harvested on day 19 of culture and 2.4×10¹⁰ CD4⁺ T cells recovered. Viability was >95%. Thus, CD4⁺ T cells can be expanded to high cell numbers in large cultures by stimulating the T cells with anti-CD3 and anti-CD28 coated beads, and will thus be useful for clinical uses.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inducing ex vivo proliferation of a population of T cells to sufficient numbers for use in therapy, comprising contacting a population of T cells ex vivo with a surface having covalently attached thereto:
   (a) an anti-CD3 antibody or CD3-binding fragment thereof, which provides a primary activation signal to the T cells, thereby activating the T cells; and
   (b) an anti-CD28 antibody or CD28-binding fragment thereof, which stimulates a CD28 accessory molecule on the surface of the T cells, thereby stimulating the activated T cells,
   wherein the anti-CD3 antibody or CD3-binding fragment thereof, and the anti-CD28 antibody or CD28-binding fragment thereof, are covalently attached to the same surface,
   the anti-CD3 antibody or CD3-binding fragment thereof, and the anti-CD28 antibody or CD28-binding fragment thereof, thereby inducing the population of T cells to proliferate to sufficient numbers for use in therapy.

2. The method of claim 1, wherein the anti-CD3 antibody or CD3-binding fragment thereof is an anti-human CD3 monoclonal antibody or CD3-binding fragment thereof.

3. The method of claim 1, wherein the anti-CD28 antibody or CD28-binding fragment thereof is an anti-human CD28 monoclonal antibody or CD28-binding fragment thereof.

4. The method of claim 1, wherein the anti-CD3 antibody or CD3-binding fragment thereof, and the anti-CD28antibody or CD28-binding fragment thereof, are covalently attached to the same surface using tosyl linkage.

5. The method of claim 1, further comprising:
   monitoring the proliferation of the T cells; and
   reactivating and re-stimulating the T cells with the anti-CD3 antibody or CD3-binding fragment thereof, and the anti-CD28antibody or CD28-binding fragment thereof, when the rate of T cell proliferation has decreased to induce further proliferation of the T cells.

6. The method of claim 5, wherein the step of monitoring proliferation of the T cells is by examining cell size or determining the level of expression of a cell surface molecule selected from the group consisting of B7-1, B7-2, and any combination thereof, and the step of reactivating and restimulating is initiated when T cell size has decreased or when the level of the cell surface molecule has decreased.

7. The method of claim 1, wherein the T cells are induced to proliferate to about 100-fold the original T cell population.

8. The method of claim 1, wherein the T cells are induced to proliferate to about 100,000-fold the original T cell population.

9. The method of claim 1, wherein the T cells are induced to proliferate for at least 3 days.

10. The method of claim 1, wherein the T cells are induced to proliferate for at least 7 days.

11. The method of claim 1, wherein the surface is a bead.

12. The method of claim 1, wherein the bead is a magnetic bead.

13. The method of claim 1, wherein the bead is a polystyrene bead.

14. The method of claim 1, wherein the surface is a cell surface.

15. The method of claim 1, wherein the surface is a tissue culture dish.

16. The method of claim 1, wherein the population of T cells are induced to proliferate to sufficient numbers for use in treating cancer.

17. The method of claim 1, wherein the population of T cells are induced to proliferate to sufficient numbers for use in treating an infectious disease.

18. The anti-CD28 antibody of claim 3, wherein the antibody is 9.3, produced by the hybridoma assigned ATCC No. HB-10271.

19. The anti-CD28 antibody of claim 3, wherein the antibody is EX 5.3D10, produced by the hybridoma assigned ATCC No. HB-11373.

* * * * *

UNITED STATES PATENT AND TRADEMARK OFFICE
CERTIFICATE OF CORRECTION

PATENT NO. : 6,887,466 B2
DATED : May 3, 2005
INVENTOR(S) : Carl H. June et al.

It is certified that error appears in the above-identified patent and that said Letters Patent is hereby corrected as shown below:

Title page,
Item [73], Assignee, replace "Genetics Institute, Inc." with -- Genetics Institute, LLC --.
Item [63], Related U.S. Application Data, delete ", now Pat. No. 5,635,697".
Item [74], *Attorney, Agent, or Firm*, replace "Wilmer Cutler Pickering; Hale and Dorr LLP" with -- Wilmer Cutler Pickering Hale and Dorr LLP --.

Column 73,
Line 21, replace "The method of claim 1," with -- The method of claim 10, --.

Column 74,
Line 1, replace "The method of claim 1," with -- The method of claim 10, --.

Signed and Sealed this

Thirtieth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,887,466 B2
DATED : May 3, 2005
INVENTOR(S) : Carl H. June et al.

It is certified that error appears in the above-identified patent and that said Letters Patent is hereby corrected as shown below:

Column 72,
Line 61, replace "CD28antibody" with -- CD28 antibody --.
Line 67, replace "anti-CD28antibody" with -- anti-CD28 antibody --.

Column 73,
Line 21, replace "The method of claim 10," with -- The method of claim 11, --.

Column 74,
Line 1, replace "The method of claim 10," with -- The method of claim 11, --.

Signed and Sealed this

Twentieth Day of December, 2005

JON W. DUDAS
*Director of the United States Patent and Trademark Office*

```
                              SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Homo sapien
        (F) TISSUE TYPE: lymphoid
        (G) CELL TYPE: B cell
        (H) CELL LINE: Raji (vii) IMMEDIATE SOURCE:
        (A) LIBRARY: cDNA in pCDM8 vector
        (B) CLONE: B7, Raji clone #13

(viii) POSITION IN GENOME:
        (A) CHROMOSOME/SEGMENT: 3

(ix) FEATURE:
        (A) NAME/KEY:  Open reading frame (translated region)
        (B) LOCATION:  318 to 1181 bp
        (C) IDENTIFICATION METHOD: similarity to other pattern (ix) FEATURE:
        (A) NAME/KEY:  Alternate polyadenylation signal
        (B) LOCATION:  1474 to 1479 bp
        (C) IDENTIFICATION METHOD: similarity to other pattern (x) PUBLICATION INFORMATION:
        (A) AUTHORS: FREEMAN, GORDON J.
            FREEDMAN, ARNOLD S.
            SEGIL, JEFFREY M.
            LEE, GRACE
            WHITMAN, JAMES F.
            NADLER, LEE M.
        (B) TITLE:  B7, A New Member Of The Ig Superfamily With
            Unique Expression On Activated And Neoplastic B Cells
        (C) JOURNAL: The Journal of Immunology
        (D) VOLUME: 143
        (E) ISSUE: 8
        (F) PAGES: 2714-2722
        (G) DATE: 15-OCT-1989
        (H) RELEVANT RESIDUES IN SEQ ID NO:1: FROM 1 TO 1491

(xi) SEQUENCE DESCRIPTION: SEQ ID NO:1:
```

```
CCAAAGAAAA AGTGATTTGT CATTGCTTTA TAGACTGTAA GAAGAGAACA TCTCAGAAGT      60

GGAGTCTTAC CCTGAAATCA AAGGATTTAA AGAAAAAGTG GAATTTTTCT TCAGCAAGCT     120

GTGAAACTAA ATCCACAACC TTTGGAGACC CAGGAACACC CTCCAATCTC TGTGTGTTTT     180

GTAAACATCA CTGGAGGGTC TTCTACGTGA GCAATTGGAT TGTCATCAGC CCTGCCTGTT     240

TTGCACCTGG GAAGTGCCCT GGTCTTACTT GGGTCCAAAT TGTTGGCTTT CACTTTTGAC     300

CCTAAGCATC TGAAGCC ATG GGC CAC ACA CGG AGG CAG GGA ACA TCA CCA TCC    353
                   Met Gly His Thr Arg Arg Gln Gly Thr Ser Pro Ser
                                   -30                 -25
```

| | | | | | | | | | | | | | | |
|---|---|---|---|---|---|---|---|---|---|---|---|---|---|---|
| AAG | TGT | CCA | TAC | CTG | AAT | TTC | TTT | CAG | CTC | TTG | GTG | CTG | GCT | GGT | CTT | 401 |

```
AAG TGT CCA TAC CTG AAT TTC TTT CAG CTC TTG GTG CTG GCT GGT CTT       401
Lys Cys Pro Tyr Leu Asn Phe Phe Gln Leu Leu Val Leu Ala Gly Leu
        -20             -15             -10

TCT CAC TTC TGT TCA GGT GTT ATC CAC GTG ACC AAG GAA GTG AAA GAA       449
Ser His Phe Cys Ser Gly Val Ile His Val Thr Lys Glu Val Lys Glu
     -5              1               5                   10

GTG GCA ACG CTG TCC TGT GGT CAC AAT GTT TCT GTT GAA GAG CTG GCA       497
Val Ala Thr Leu Ser Cys Gly His Asn Val Ser Val Glu Glu Leu Ala
                 15              20              25

CAA ACT CGC ATC TAC TGG CAA AAG GAG AAG AAA ATG GTG CTG ACT ATG       545
Gln Thr Arg Ile Tyr Trp Gln Lys Glu Lys Lys Met Val Leu Thr Met
             30              35              40

ATG TCT GGG GAC ATG AAT ATA TGG CCC GAG TAC AAG AAC CGG ACC ATC       593
Met Ser Gly Asp Met Asn Ile Trp Pro Glu Tyr Lys Asn Arg Thr Ile
             45              50              55

TTT GAT ATC ACT AAT AAC CTC TCC ATT GTG ATC CTG GCT CTG CGC CCA       641
Phe Asp Ile Thr Asn Asn Leu Ser Ile Val Ile Leu Ala Leu Arg Pro
         60              65              70

TCT GAC GAG GGC ACA TAC GAG TGT GTT GTT CTG AAG TAT GAA AAA GAC       689
Ser Asp Glu Gly Thr Tyr Glu Cys Val Val Leu Lys Tyr Glu Lys Asp
 75              80              85              90

GCT TTC AAG CGG GAA CAC CTG GCT GAA GTG ACG TTA TCA GTC AAA GCT       737
Ala Phe Lys Arg Glu His Leu Ala Glu Val Thr Leu Ser Val Lys Ala
                 95              100             105

GAC TTC CCT ACA CCT AGT ATA TCT GAC TTT GAA ATT CCA ACT TCT AAT       785
Asp Phe Pro Thr Pro Ser Ile Ser Asp Phe Glu Ile Pro Thr Ser Asn
             110             115             120

ATT AGA AGG ATA ATT TGC TCA ACC TCT GGA GGT TTT CCA GAG CCT CAC       833
Ile Arg Arg Ile Ile Cys Ser Thr Ser Gly Gly Phe Pro Glu Pro His
             125             130             135

CTC TCC TGG TTG GAA AAT GGA GAA GAA TTA AAT GCC ATC AAC ACA ACA       881
Leu Ser Trp Leu Glu Asn Gly Glu Glu Leu Asn Ala Ile Asn Thr Thr
         140             145             150

GTT TCC CAA GAT CCT GAA ACT GAG CTC TAT GCT GTT AGC AGC AAA CTG       929
Val Ser Gln Asp Pro Glu Thr Glu Leu Tyr Ala Val Ser Ser Lys Leu
155             160             165             170

GAT TTC AAT ATG ACA ACC AAC CAC AGC TTC ATG TGT CTC ATC AAG TAT       977
Asp Phe Asn Met Thr Thr Asn His Ser Phe Met Cys Leu Ile Lys Tyr
                 175             180             185

GGA CAT TTA AGA GTG AAT CAG ACC TTC AAC TGG AAT ACA ACC AAG CAA      1025
Gly His Leu Arg Val Asn Gln Thr Phe Asn Trp Asn Thr Thr Lys Gln
             190             195             200

GAG CAT TTT CCT GAT AAC CTG CTC CCA TCC TGG GCC ATT ACC TTA ATC      1073
Glu His Phe Pro Asp Asn Leu Leu Pro Ser Trp Ala Ile Thr Leu Ile
         205             210             215

TCA GTA AAT GGA ATT TTT GTG ATA TGC TGC CTG ACC TAC TGC TTT GCC      1121
Ser Val Asn Gly Ile Phe Val Ile Cys Cys Leu Thr Tyr Cys Phe Ala
     220             225             230
```

-continued

```
CCA AGA TGC AGA GAG AGA AGG AGG AAT GAG AGA TTG AGA AGG GAA AGT      1169
Pro Arg Cys Arg Glu Arg Arg Arg Asn Glu Arg Leu Arg Arg Glu Ser
235                 240                 245                 250

GTA CGC CCT GTA   TAACAGTGTC CGCAGAAGCA AGGGGCTGAA AAGATCTGAA         1221
Val Arg Pro Val

GGTAGCCTCC GTCATCTCTT CTGGGATACA TGGATCGTGG GGATCATGAG GCATTCTTCC    1281
CTTAACAAAT TTAAGCTGTT TTACCCACTA CCTCACCTTC TTAAAAACCT CTTTCAGATT    1341

AAGCTGAACA GTTACAAGAT GGCTGGCATC CCTCTCCTTT CTCCCCATAT GCAATTTGCT    1401

TAATGTAACC TCTTCTTTTG CCATGTTTCC ATTCTGCCAT CTTGAATTGT CTTGTCAGCC    1461

AATTCATTAT CTATTAAACA CTAATTTGAG                                     1491
```

(2) INFORMATION FOR SEQ ID NO:2:

(i) SEQUENCE CHARACTERISTICS:
        (A) LENGTH: 288 amino acids
        (B) TYPE: amino acid
        (C) TOPOLOGY: linear (ii) MOLECULE TYPE: protein
        (A) DESCRIPTION: B cell activation antigen; natural ligand
            for CD28 T cell surface antigen; transmembrane protein (ix) FEATURE:
        (A) NAME/KEY: signal sequence
        (B) LOCATION: -34 to -1
        (C) IDENTIFICATION METHOD: amino terminal sequencing of
            soluble protein
        (D) OTHER INFORMATION: hydrophobic (ix) FEATURE:
        (A) NAME/KEY: extracellular domain
        (B) LOCATION: 1 to 208
        (C) IDENTIFICATION METHOD: similarity with known
            sequence (ix) FEATURE:
        (A) NAME/KEY: transmembrane domain
        (B) LOCATION: 209 to 235
        (C) IDENTIFICATION METHOD: similarity with known
            sequence (ix) FEATURE:
        (A) NAME/KEY: intracellular domain
        (B) LOCATION: 236 to 254
        (C) IDENTIFICATION METHOD: similarity with known
            sequence (ix) FEATURE:
        (A) NAME/KEY: N-linked glycosylation
        (B) LOCATION: 19 to 21
        (C) IDENTIFICATION METHOD: similarity with known
            sequence (ix) FEATURE:
        (A) NAME/KEY: N-linked glycosylation
        (B) LOCATION: 55 to 57
        (C) IDENTIFICATION METHOD: similarity with known
            sequence (ix) FEATURE:
        (A) NAME/KEY: N-linked glycosylation
        (B) LOCATION: 64 to 66
        (C) IDENTIFICATION METHOD: similarity with known
            sequence (ix) FEATURE:
        (A) NAME/KEY: N-linked glycosylation
        (B) LOCATION: 152 to 154
        (C) IDENTIFICATION METHOD: similarity with known
            sequence (ix) FEATURE:
        (A) NAME/KEY: N-linked glycosylation
        (B) LOCATION: 173 to 175

(C) IDENTIFICATION METHOD: similarity with known
                sequence (ix) FEATURE:
            (A) NAME/KEY: N-linked glycosylation
            (B) LOCATION: 177 to 179
            (C) IDENTIFICATION METHOD: similarity with known
                sequence (ix) FEATURE:
            (A) NAME/KEY: N-linked glycosylation
            (B) LOCATION: 192 to 194
            (C) IDENTIFICATION METHOD: similarity with known
                sequence (ix) FEATURE:
            (A) NAME/KEY: N-linked glycosylation
            (B) LOCATION: 198 to 200
            (C) IDENTIFICATION METHOD: similarity with known
                sequence (ix) FEATURE:
            (A) NAME/KEY: Ig V-set domain
            (B) LOCATION: 1 to 104
            (C) IDENTIFICATION METHOD: similarity with known
                sequence (ix) FEATURE:
            (A) NAME/KEY: Ig C-set domain
            (B) LOCATION:  105 to 202
            (C) IDENTIFICATION METHOD: similarity with known
                sequence (x) PUBLICATION INFORMATION:
            (A) AUTHORS: FREEMAN, GORDON J.
                  FREEDMAN, ARNOLD S.
                  SEGIL, JEFFREY M.
                  LEE, GRACE
                  WHITMAN, JAMES F.
                  NADLER, LEE M.
            (B) TITLE: B7, A New Member Of The Ig Superfamily With
                  Unique Expression On Activated And Neoplastic B Cells
            (C) JOURNAL: The Journal of Immunology
            (D) VOLUME: 143
            (E) ISSUE: 8
            (F) PAGES: 2714-2722
            (G) DATE:  15-OCT-1989
            (H) RELEVANT RESIDUES IN SEQ ID NO:2: From -26 to 262

(xi) SEQUENCE DESCRIPTION: SEQ ID NO:2:

Met Gly His Thr Arg Arg Gln Gly Thr Ser Pro Ser Lys Cys Pro Tyr
            -30                 -25                 -20

Leu Asn Phe Phe Gln Leu Leu Val Leu Ala Gly Leu Ser His Phe Cys
            -15                 -10                  -5

Ser Gly Val Ile His Val Thr Lys Glu Val Lys Glu Val Ala Thr Leu
     -1   1               5                  10

Ser Cys Gly His Asn Val Ser Val Glu Glu Leu Ala Gln Thr Arg Ile
 15                  20                  25                  30

Tyr Trp Gln Lys Glu Lys Lys Met Val Leu Thr Met Met Ser Gly Asp
                 35                  40                  45

Met Asn Ile Trp Pro Glu Tyr Lys Asn Arg Thr Ile Phe Asp Ile Thr
                 50                  55                  60

Asn Asn Leu Ser Ile Val Ile Leu Ala Leu Arg Pro Ser Asp Glu Gly
             65                  70                  75

Thr Tyr Glu Cys Val Val Leu Lys Tyr Glu Lys Asp Ala Phe Lys Arg
         80                  85                  90

Glu His Leu Ala Glu Val Thr Leu Ser Val Lys Ala Asp Phe Pro Thr
 95                 100                 105                 110

Pro Ser Ile Ser Asp Phe Glu Ile Pro Thr Ser Asn Ile Arg Arg Ile

```
                    115                 120                 125
Ile Cys Ser Thr Ser Gly Gly Phe Pro Glu Pro His Leu Ser Trp Leu
            130                 135                 140

Glu Asn Gly Glu Glu Leu Asn Ala Ile Asn Thr Thr Val Ser Gln Asp
            145                 150                 155

Pro Glu Thr Glu Leu Tyr Ala Val Ser Ser Lys Leu Asp Phe Asn Met
        160                 165                 170

Thr Thr Asn His Ser Phe Met Cys Leu Ile Lys Tyr Gly His Leu Arg
175                 180                 185                 190

Val Asn Gln Thr Phe Asn Trp Asn Thr Thr Lys Gln Glu His Phe Pro
            195                 200                 205

Asp Asn Leu Leu Pro Ser Trp Ala Ile Thr Leu Ile Ser Val Asn Gly
            210                 215                 220

Ile Phe Val Ile Cys Cys Leu Thr Tyr Cys Phe Ala Pro Arg Cys Arg
            225                 230                 235

Glu Arg Arg Arg Asn Glu Arg Leu Arg Arg Glu Ser Val Arg Pro Val
    240                 245                 250

(2) INFORMATION FOR SEQ ID NO:3:

(i) SEQUENCE CHARACTERISTICS:
        (A) LENGTH: 1120 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 107..1093

(xi) SEQUENCE DESCRIPTION: SEQ ID NO:3:

CACAGGGTGA AAGCTTTGCT TCTCTGCTGC TGTAACAGGG ACTAGCACAG ACACACGGAT      60

GAGTGGGGTC ATTTCCAGAT ATTAGGTCAC AGCAGAAGCA GCCAAA ATG GAT CCC        115
                                                Met Asp Pro
                                                  1

CAG TGC ACT ATG GGA CTG AGT AAC ATT CTC TTT GTG ATG GCC TTC CTG       163
Gln Cys Thr Met Gly Leu Ser Asn Ile Leu Phe Val Met Ala Phe Leu
    5                  10                  15

CTC TCT GGT GCT GCT CCT CTG AAG ATT CAA GCT TAT TTC AAT GAG ACT       211
Leu Ser Gly Ala Ala Pro Leu Lys Ile Gln Ala Tyr Phe Asn Glu Thr
 20                  25                  30                  35

GCA GAC CTG CCA TGC CAA TTT GCA AAC TCT CAA AAC CAA AGC CTG AGT       259
Ala Asp Leu Pro Cys Gln Phe Ala Asn Ser Gln Asn Gln Ser Leu Ser
             40                  45                  50

GAG CTA GTA GTA TTT TGG CAG GAC CAG GAA AAC TTG GTT CTG AAT GAG       307
Glu Leu Val Val Phe Trp Gln Asp Gln Glu Asn Leu Val Leu Asn Glu
         55                  60                  65

GTA TAC TTA GGC AAA GAG AAA TTT GAC AGT GTT CAT TCC AAG TAT ATG       355
Val Tyr Leu Gly Lys Glu Lys Phe Asp Ser Val His Ser Lys Tyr Met
     70                  75                  80

GGC CGC ACA AGT TTT GAT TCG GAC AGT TGG ACC CTG AGA CTT CAC AAT       403
Gly Arg Thr Ser Phe Asp Ser Asp Ser Trp Thr Leu Arg Leu His Asn
 85                  90                  95

CTT CAG ATC AAG GAC AAG GGC TTG TAT CAA TGT ATC ATC CAT CAC AAA       451
Leu Gln Ile Lys Asp Lys Gly Leu Tyr Gln Cys Ile Ile His His Lys
100                 105                 110                 115

AAG CCC ACA GGA ATG ATT CGC ATC CAC CAG ATG AAT TCT GAA CTG TCA       499
Lys Pro Thr Gly Met Ile Arg Ile His Gln Met Asn Ser Glu Leu Ser
```

```
                    120              125              130
GTG CTT GCT AAC TTC AGT CAA CCT GAA ATA GTA CCA ATT TCT AAT ATA        547
Val Leu Ala Asn Phe Ser Gln Pro Glu Ile Val Pro Ile Ser Asn Ile
                135              140              145

ACA GAA AAT GTG TAC ATA AAT TTG ACC TGC TCA TCT ATA CAC GGT TAC        595
Thr Glu Asn Val Tyr Ile Asn Leu Thr Cys Ser Ser Ile His Gly Tyr
                150              155              160

CCA GAA CCT AAG AAG ATG AGT GTT TTG CTA AGA ACC AAG AAT TCA ACT        643
Pro Glu Pro Lys Lys Met Ser Val Leu Leu Arg Thr Lys Asn Ser Thr
        165              170              175

ATC GAG TAT GAT GGT ATT ATG CAG AAA TCT CAA GAT AAT GTC ACA GAA        691
Ile Glu Tyr Asp Gly Ile Met Gln Lys Ser Gln Asp Asn Val Thr Glu
180              185              190              195

CTG TAC GAC GTT TCC ATC AGC TTG TCT GTT TCA TTC CCT GAT GTT ACG        739
Leu Tyr Asp Val Ser Ile Ser Leu Ser Val Ser Phe Pro Asp Val Thr
                    200              205              210

AGC AAT ATG ACC ATC TTC TGT ATT CTG GAA ACT GAC AAG ACG CGG CTT        787
Ser Asn Met Thr Ile Phe Cys Ile Leu Glu Thr Asp Lys Thr Arg Leu
                215              220              225

TTA TCT TCA CCT TTC TCT ATA GAG CTT GAG GAC CCT CAG CCT CCC CCA        835
Leu Ser Ser Pro Phe Ser Ile Glu Leu Glu Asp Pro Gln Pro Pro Pro
                230              235              240

GAC CAC ATT CCT TGG ATT ACA GCT GTA CTT CCA ACA GTT ATT ATA TGT        883
Asp His Ile Pro Trp Ile Thr Ala Val Leu Pro Thr Val Ile Ile Cys
        245              250              255

GTG ATG GTT TTC TGT CTA ATT CTA TGG AAA TGG AAG AAG AAG AAG CGG        931
Val Met Val Phe Cys Leu Ile Leu Trp Lys Trp Lys Lys Lys Lys Arg
260              265              270              275

CCT CGC AAC TCT TAT AAA TGT GGA ACC AAC ACA ATG GAG AGG GAA GAG        979
Pro Arg Asn Ser Tyr Lys Cys Gly Thr Asn Thr Met Glu Arg Glu Glu
                    280              285              290

AGT GAA CAG ACC AAG AAA AGA GAA AAA ATC CAT ATA CCT GAA AGA TCT       1027
Ser Glu Gln Thr Lys Lys Arg Glu Lys Ile His Ile Pro Glu Arg Ser
                295              300              305

GAT GAA GCC CAG CGT GTT TTT AAA AGT TCG AAG ACA TCT TCA TGC GAC       1075
Asp Glu Ala Gln Arg Val Phe Lys Ser Ser Lys Thr Ser Ser Cys Asp
                310              315              320

AAA AGT GAT ACA TGT TTT TAATTAAAGA GTAAAGCCCA AAAAAAA                 1120
Lys Ser Asp Thr Cys Phe
    325

(2) INFORMATION FOR SEQ ID NO:4:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Pro Gln Cys Thr Met Gly Leu Ser Asn Ile Leu Phe Val Met
  1               5                  10                  15

Ala Phe Leu Leu Ser Gly Ala Ala Pro Leu Lys Ile Gln Ala Tyr Phe
                 20                  25                  30

Asn Glu Thr Ala Asp Leu Pro Cys Gln Phe Ala Asn Ser Gln Asn Gln
             35                  40                  45

Ser Leu Ser Glu Leu Val Val Phe Trp Gln Asp Gln Glu Asn Leu Val
         50                  55                  60

Leu Asn Glu Val Tyr Leu Gly Lys Glu Lys Phe Asp Ser Val His Ser
```

```
            65                  70                  75                  80
        Lys Tyr Met Gly Arg Thr Ser Phe Asp Ser Asp Ser Trp Thr Leu Arg
                            85                  90                  95

Leu His Asn Leu Gln Ile Lys Asp Lys Gly Leu Tyr Gln Cys Ile Ile
                           100                 105                 110

His His Lys Lys Pro Thr Gly Met Ile Arg Ile His Gln Met Asn Ser
                           115                 120                 125

Glu Leu Ser Val Leu Ala Asn Phe Ser Gln Pro Glu Ile Val Pro Ile
                           130                 135                 140

Ser Asn Ile Thr Glu Asn Val Tyr Ile Asn Leu Thr Cys Ser Ser Ile
        145                 150                 155                 160

His Gly Tyr Pro Glu Pro Lys Lys Met Ser Val Leu Leu Arg Thr Lys
                           165                 170                 175

Asn Ser Thr Ile Glu Tyr Asp Gly Ile Met Gln Lys Ser Gln Asp Asn
                           180                 185                 190

Val Thr Glu Leu Tyr Asp Val Ser Ile Ser Leu Ser Val Ser Phe Pro
                           195                 200                 205

Asp Val Thr Ser Asn Met Thr Ile Phe Cys Ile Leu Glu Thr Asp Lys
                           210                 215                 220

Thr Arg Leu Leu Ser Ser Pro Phe Ser Ile Glu Leu Glu Asp Pro Gln
        225                 230                 235                 240

Pro Pro Pro Asp His Ile Pro Trp Ile Thr Ala Val Leu Pro Thr Val
                           245                 250                 255

Ile Ile Cys Val Met Val Phe Cys Leu Ile Leu Trp Lys Trp Lys Lys
                           260                 265                 270

Lys Lys Arg Pro Arg Asn Ser Tyr Lys Cys Gly Thr Asn Thr Met Glu
                           275                 280                 285

Arg Glu Glu Ser Glu Gln Thr Lys Lys Arg Glu Lys Ile His Ile Pro
                           290                 295                 300

Glu Arg Ser Asp Glu Ala Gln Arg Val Phe Lys Ser Ser Lys Thr Ser
        305                 310                 315                 320

Ser Cys Asp Lys Ser Asp Thr Cys Phe
                           325

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (B) LOCATION: 1
        (D) OTHER INFORMATION: /label=Xaa is any amino acid (ix) FEATURE:
        (A) NAME/KEY: misc_feature
        (B) LOCATION: 3
        (D) OTHER INFORMATION: /label=Xaa is any amino acid (ix) FEATURE:
        (A) NAME/KEY: misc_feature
        (B) LOCATION: 6
        (D) OTHER INFORMATION: /label=Xaa is any amino acid (ix) FEATURE:
        (A) NAME/KEY: misc_feature
        (B) LOCATION: 7
        (D) OTHER INFORMATION: /label=Xaa is any amino acid
```

```
        (ix) FEATURE:
              (A) NAME/KEY: misc_feature
              (B) LOCATION: 8
              (D) OTHER INFORMATION: /label=Xaa is Asp or Glu (ix) FEATURE:
              (A) NAME/KEY: misc_feature
              (B) LOCATION: 9
              (D) OTHER INFORMATION: /label=Xaa is any amino acid (xi) SEQUENCE DESCRIPTION: SEQ ID NO:5:

Xaa Gly Xaa Trp Leu Xaa Xaa Xaa Xaa
                  5

(2) INFORMATION FOR SEQ ID NO:6:

(i) SEQUENCE CHARACTERISTICS:
              (A) LENGTH: 227 amino acids
              (B) TYPE: amino acid
              (D) TOPOLOGY: linear (ii) MOLECULE TYPE: protein (xi) SEQUENCE DESCRIPTION: SEQ ID NO:6:

Pro Val Lys Gly Gly Thr Lys Cys Ile Lys Tyr Leu Leu Phe Gly Phe
                  5                  10                  15

Asn Phe Ile Phe Trp Leu Ala Gly Ile Ala Val Leu Ala Ile Gly Leu
                 20                  25                  30

Trp Leu Arg Phe Asp Ser Gln Thr Lys Ser Ile Phe Glu Gln Glu Thr
             35                  40                  45

Asn Asn Asn Asn Ser Ser Phe Tyr Thr Gly Val Tyr Ile Leu Ile Gly
 50                  55                  60

Ala Gly Ala Leu Met Met Leu Val Gly Phe Leu Gly Cys Cys Gly Ala
 65                  70                  75                  80

Val Gln Glu Ser Gln Cys Met Leu Gly Leu Phe Phe Gly Phe Leu Leu
                 85                  90                  95

Val Ile Phe Ala Ile Glu Ile Ala Ala Ala Ile Trp Gly Tyr Ser His
                100                 105                 110

Lys Asp Glu Val Ile Lys Glu Val Gln Glu Phe Tyr Lys Asp Thr Tyr
            115                 120                 125

Asn Lys Leu Lys Thr Lys Asp Glu Pro Gln Arg Glu Thr Leu Lys Ala
130                 135                 140

Ile His Tyr Ala Leu Asn Cys Cys Gly Leu Ala Gly Gly Val Glu Gln
145                 150                 155                 160

Phe Ile Ser Asp Ile Cys Pro Lys Lys Asp Val Leu Glu Thr Phe Thr
                165                 170                 175

Val Lys Ser Cys Pro Asp Ala Ile Lys Glu Val Phe Asp Asn Lys Phe
            180                 185                 190

His Ile Ile Gly Ala Val Gly Ile Gly Ile Ala Val Val Met Ile Phe
            195                 200                 205

Gly Met Ile Phe Ser Met Ile Leu Cys Cys Ala Ile Arg Arg Asn Arg
210                 215                 220

Glu Met Val
225

(2) INFORMATION FOR SEQ ID NO:7:

(i) SEQUENCE CHARACTERISTICS:
              (A) LENGTH: 7 amino acids
              (B) TYPE: amino acid
```

-continued (D) TOPOLOGY: linear (ii) MOLECULE TYPE: peptide (xi) SEQUENCE DESCRIPTION: SEQ ID NO:7:

Gly Leu Trp Leu Arg Phe Asp
1               5

(2) INFORMATION FOR SEQ ID NO:8:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO:8:

His Gln Phe Cys Asp His Trp Gly Cys Trp Leu Leu Arg Glu Thr His
1               5                   10                  15

Ile Phe Thr Pro
            20

(2) INFORMATION FOR SEQ ID NO:9:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO:9:

Leu Arg Leu Val Leu Glu Asp Pro Gly Ile Trp Leu Arg Pro Asp Tyr
1               5                   10                  15

Phe Phe Pro Ala
            20

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:10:

Gly Cys Trp Leu Leu Arg Glu
1               5

(2) INFORMATION FOR SEQ ID NO:11:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:11:

Gly Ile Trp Leu Arg Pro Asp
1               5

(2) INFORMATION FOR SEQ ID NO:12:

(i) SEQUENCE CHARACTERISTICS:

-continued

```
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (B) LOCATION: 2
        (D) OTHER INFORMATION: /label=Xaa is any amino acid (ix) FEATURE:
        (A) NAME/KEY: misc_feature
        (B) LOCATION: 5
        (D) OTHER INFORMATION: /label=Xaa is any amino acid (ix) FEATURE:
        (A) NAME/KEY: misc_feature
        (B) LOCATION: 6
        (D) OTHER INFORMATION: /label=Xaa is Asp or Glu (xi) SEQUENCE DESCRIPTION: SEQ ID NO:12:

Gly Xaa Trp Leu Xaa Xaa
1               5

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTTTAGAGCA CA                                                           12

(2) INFORMATION FOR SEQ ID NO:14:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CTCTAAAG                                                                 8
```